US010806802B2

(12) United States Patent
Wootton et al.

(10) Patent No.: US 10,806,802 B2
(45) Date of Patent: Oct. 20, 2020

(54) ADENO-ASSOCIATED VIRUS PARTICLE WITH MUTATED CAPSID AND METHODS OF USE THEREOF

(71) Applicants: University of Guelph, Guelph (CA); Ottawa Hospital Research Institute, Ottawa (CA)

(72) Inventors: Sarah Wootton, Guelph (CA); Laura van Lieshout, Guelph (CA); Bernard Claude Frank Thebaud, Ottawa (CA); Martin Hubert Kang, Ottawa (CA)

(73) Assignees: University of Guelph, Guelph (CA); Ottawa Hospital Research Institute, Ottawa (CA)

( * ) Notice: Subject to any disclaimer, the term of this patent is extended or adjusted under 35 U.S.C. 154(b) by 0 days.

(21) Appl. No.: 16/251,119

(22) Filed: Jan. 18, 2019

(65) Prior Publication Data
US 2019/0216949 A1 Jul. 18, 2019

Related U.S. Application Data

(60) Provisional application No. 62/618,810, filed on Jan. 18, 2018.

(30) Foreign Application Priority Data

Nov. 9, 2018 (CA) .................................. 3023706

(51) Int. Cl.
| | | |
|---|---|---|
| *C12N 15/00* | (2006.01) | |
| *C12N 15/86* | (2006.01) | |
| *A61K 48/00* | (2006.01) | |
| *A61K 9/12* | (2006.01) | |
| *A61P 31/14* | (2006.01) | |
| *A61K 9/00* | (2006.01) | |

(52) U.S. Cl.
CPC ............ *A61K 48/0058* (2013.01); *A61K 9/12* (2013.01); *A61K 48/0008* (2013.01); *A61K 48/0066* (2013.01); *A61K 48/0075* (2013.01); *A61K 48/0091* (2013.01); *A61P 31/14* (2018.01); *A61K 9/0019* (2013.01); *A61K 9/0043* (2013.01); *A61K 9/0073* (2013.01)

(58) Field of Classification Search
None
See application file for complete search history.

(56) References Cited

U.S. PATENT DOCUMENTS

| 8,445,267 | B2 | 5/2013 | Zhong et al. | |
| 10,301,648 | B2 | 5/2019 | Vandenberghe et al. | |
| 2014/0341852 | A1* | 11/2014 | Srivastava | C07K 14/005 424/93.2 |
| 2018/0030096 | A1 | 2/2018 | Aslanidi et al. | |
| 2018/0244727 | A1 | 8/2018 | Zhong et al. | |

FOREIGN PATENT DOCUMENTS

WO 2017201121 A1 11/2017

OTHER PUBLICATIONS

Ng et al. Structural Characterization of the Dual Glycan Binding Adeno-Associated Virus Serotype 6. J. Virol. 2010, 84: 12945-12957.*
Qiao et al. Adeno-Associated Virus Serotype 6 Capsid Tyrosine-to-Phenylalanine Mutations Improve Gene Transfer to Skeletal Muscle. Human Gene Therapy, 2010, 21:1343-1348.*
McClain et al. Vector serotype screening for use in ovine perinatal lung gene therapy. Journal of Pediatric Surgery 51 (2016) 879-884.*
Robert et al. Development of a Post-Exposure Treatment for Ebola Virus Infections Based on AAV Vectors and Zmapp Antibody Cocktail. Molecular Therapy vol. 24, Supplement 1, May 2016, S222.*
Fuchs, Sebastian P., et al., "Recombinant AAV Vectors for Enhanced Expression of Authentic IgG." Plos One, vol. 11, No. 6, 2016, doi:10.1371/journal.pone.0158009.
Limberis, Maria P, et al. "Transduction Efficiencies of Novel AAV Vectors in Mouse Airway Epithelium In Vivo and Human Ciliated Airway Epithelium In Vitro." Molecular Therapy, vol. 17, No. 2, 2009, pp. 294-301., doi:10.1038/mt.2008.261.
Markusic, David M, et al., "High-Efficiency Transduction and Correction of Murine Hemophilia B Using AAV2 Vectors Devoid of Multiple Surface-Exposed Tyrosines." Molecular Therapy, vol. 18, No. 12, 2010, pp. 2048-2056., doi:10.1038/mt.2010.172.
Kang, M., et al., "AAV—Sftpb Gene Therapy Rescues Respiratory Distress and Improves Survival in a Mouse Model of Surfactant Protein B Deficiency." poster, presented at OHRI Research Day, Ottawa, Canada, Nov. 9, 2017.
Kang, M., et al., "AAV—Sftpb Gene Therapy rescues Respiratory Distress and Improves Survival in a Mouse Model of Surfactant Protein B Deficiency." abstract, published online Nov. 9, 2017.
Kang, M., et al., "AAV—Sftpb Gene Therapy Rescues Respiratory Distress and Improves Survival in a Mouse Model of Surfactant Protein B Deficiency." poster, presented at CHEO for Research Day, Ottawa, Canada, Mar. 22, 2018.
Zhong, L., et al., "Next Generation of Adeno-Associated Virus 2 Vectors: Point Mutations in Tyrosines Lead to High-Efficiency Transduction at Lower Doses." Proceedings of the National Academy of Sciences, vol. 105, No. 22, 2008, pp. 7827-7832., doi:10. 1073/pnas.0802866105.
Van Lieshout, Laura P., et al., "Intramuscular Adeno-Associated Virus—Mediated Expression of Monoclonal Antibodies Provides 100% Protection Against Ebola Virus Infection in Mice." The Journal of Infectious Diseases, vol. 217, No. 6, 2018, pp. 916-925., doi:10.1093/infdis/jix644.

(Continued)

*Primary Examiner* — Nianxiang Zou
(74) *Attorney, Agent, or Firm* — Melanie Szweras; Herman Cheung; Bereskin & Parr LLP/S.E.N.C.R.L., s.r.l.

(57) ABSTRACT

A recombinant adeno-associated virus (rAAV) particle with a mutated capsid protein is provided. In particular, the present disclosure provides methods of delivering a therapeutic agent to a muscle, airway, liver, central nervous system, retina or lung cell in a subject, and methods of treating or preventing infectious, acquired or genetic disease, with said rAAV particle.

23 Claims, 43 Drawing Sheets

Specification includes a Sequence Listing.

(56) References Cited

OTHER PUBLICATIONS

Wu, Z. et al., "Single Amino Acid Changes Can Influence Titer, Heparin Binding, and Tissue Tropism in Different Adeno-Associated Virus Serotypes." Journal of Virology, 2006, 80(22), 11393-11397. doi:10.1128/jvi.01288-06.

Aneja, M. K et al., "Targeted gene delivery to the lung. Expert Opinion on Drug Delivery", 2009, 6(6), 567-583. doi:10.1517/17425240902927841.

Limberis et al. Transduction Efficiencies of Novel AAV Vectors in Mouse Airway Epithelium In Vivo and Human Ciliated Airway Epithelium In Vitro, Molecular Therapy, vol. 17, No. 2, Feb. 2009 [online], [retrieved on Jan. 30, 2020]. Retrieved from the Internet: <URL: https://www.cell.com/action/doSearch?searchType=quick&searchText=Transduction+Efficiencies+of+Novel+AAV+Vectors+in+Mouse+Airway+Epithelium+In +Vivo+and+Human+Ciliated+Airway+Epithelium+In+Vitro&searchScope=fullSite&occurrences=all&code=cell-site>.

Markusic et al. High-efficiency Transduction and Correction of Murine Hemophilia B Using AAV2 Vectors Devoid of Multiple Surface-exposed Tyrosines, Molecular Therapy, vol. 18, No. 12, Dec. 2010 [online], [retrieved on Jan. 30, 2020]. Retrieved from the Internet: <URL: https://www.cell.com/action/doSearch?searchType=quick&searchText=High-efficiency+Transduction+and+Correction+of+Murine+Hemophilia+B+Using +AAV2+Vectors+Devoid+of+Multiple+Surface-expose+Tyrosines&searchScope=fullSite&occurrences=all&code=cell-.

Yan et al. Distinct transduction difference between adeno-associated virus type 1 and type 6 vectors in human polarized airway epithelia, Gene Therapy, vol. 20, No. 3, Jun. 14, 2014 [online], [retrieved on Jan. 30, 2020]. Retrieved from the Internet: <URL: https://www.ncbi.nlm.nih.gov/pmc/articles/PMC3443503/> <DOI: 10.1038/gt.2012.46>.

\* cited by examiner

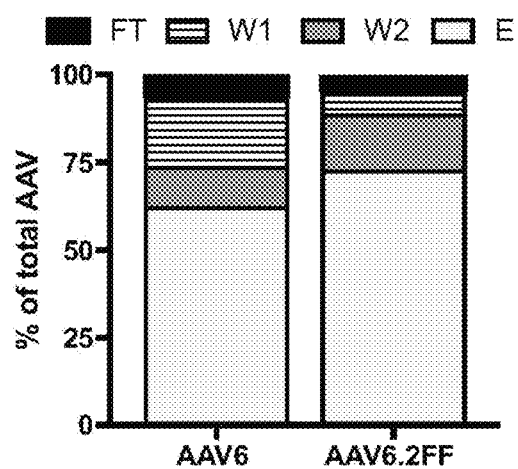
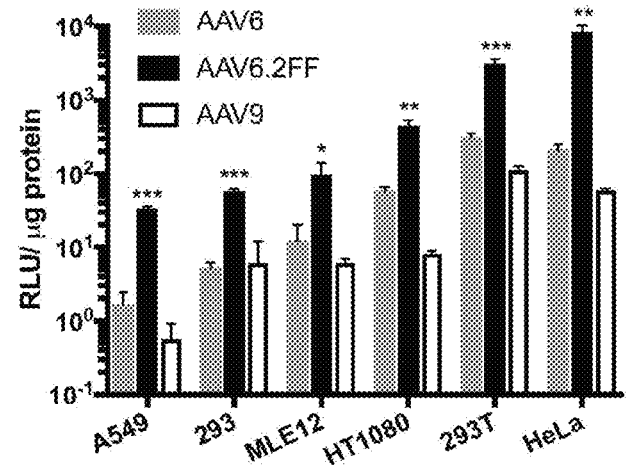
FIG. 1A
FIG. 1B
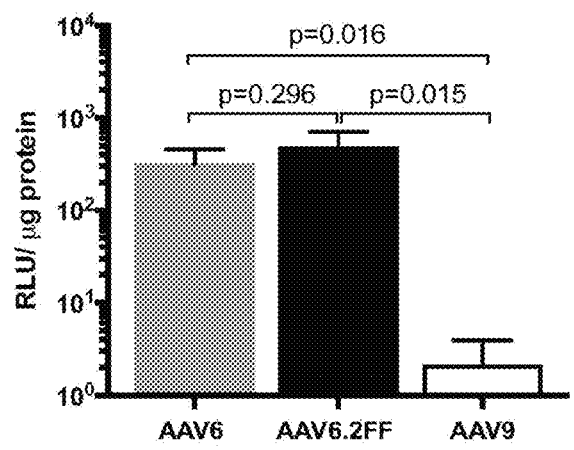
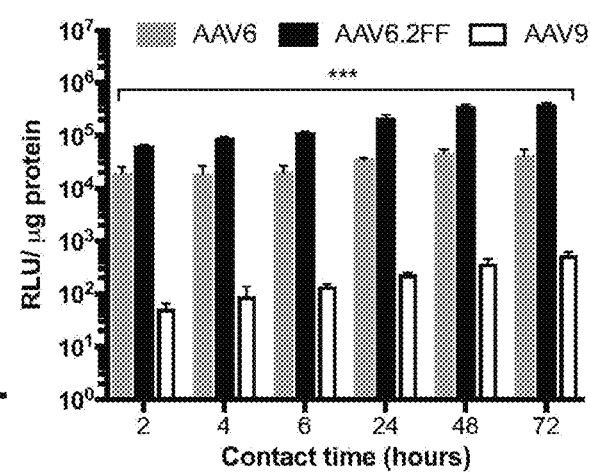
FIG. 1C
FIG. 1D

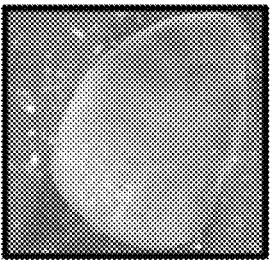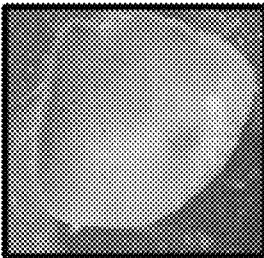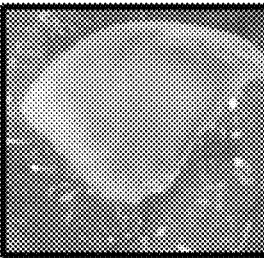
FIG. 5A  FIG. 5B  FIG. 5C  FIG. 5D
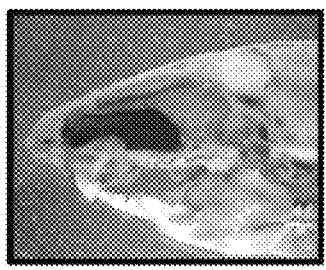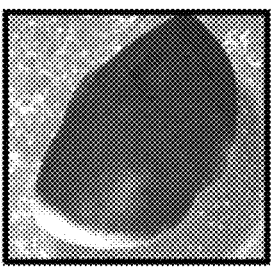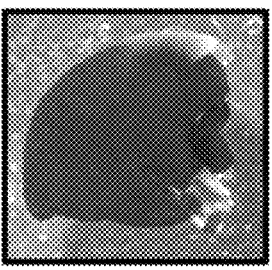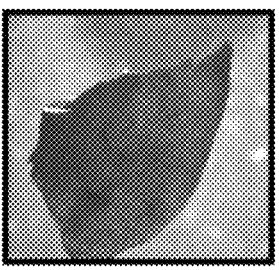
FIG. 5E  FIG. 5F  FIG. 5G  FIG. 5H

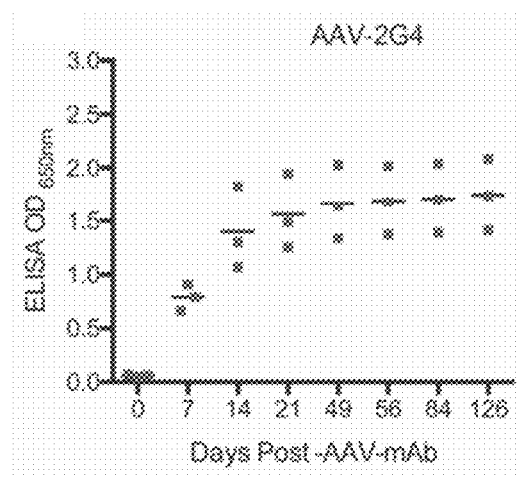 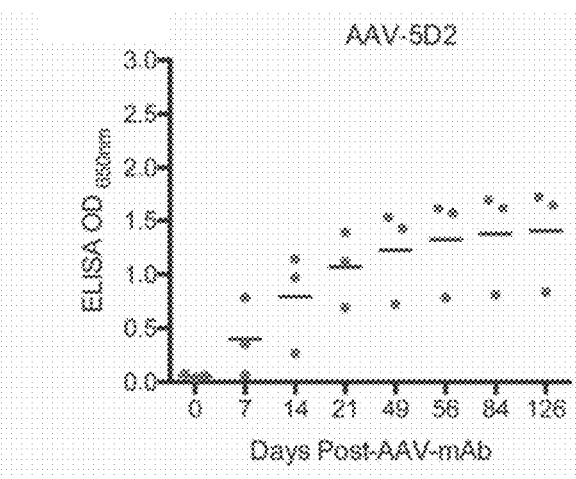
FIG. 13A          FIG. 13B

ADENO-ASSOCIATED VIRUS PARTICLE WITH MUTATED CAPSID AND METHODS OF USE THEREOF

RELATED APPLICATIONS

This application claims priority to U.S. Provisional Patent Application No. 62/618,810 filed on Jan. 18, 2018, and Canadian Patent Application No. 3,023,706 filed on Nov. 9, 2018, the content of which are hereby incorporated by reference in their entirety.

INCORPORATION OF SEQUENCE LISTING

A computer readable form of the Sequence Listing "6580-P55086US01_SequenceListing.txt" (40,096 bytes), submitted via EFS-WEB and created on Jan. 17, 2019, is herein incorporated by reference.

FIELD

The present disclosure provides a recombinant adeno-associated virus (rAAV) particle with mutated capsid protein, where the rAAV particle exhibits greater transduction of host cells compared to wild-type AAV. The present disclosure further provides methods of delivering a therapeutic agent to a muscle, airway, liver, central nervous system, retina or lung cell in a subject, and methods of treating or preventing an infectious, acquired or genetic disease, with said rAAV particle.

BACKGROUND

Adeno-associated virus (AAV) is widely regarded as a safe and effective method of gene transfer to a variety of tissues. The in vitro and in vivo transduction profiles have been well characterized for many AAV serotypes [1, 2]. Engineering of AAV capsids by rational design or directed evolution can produce capsid variants with desirable characteristics including altered tissue tropism, enhanced transgene expression in target cells or the introduction of binding domains to aid in purification to name a few. A prime example, AAV-DJ, is a product of AAV2 and AAV8 capsid shuffling, resulting in a hybrid capsid with beneficial properties of both capsids; heparin binding capacity and in vitro transduction capacities from AAV2 and potent in vivo liver transduction from AAV8 [3, 4].

Alternatively, single point mutations in an AAV capsid can also yield desirable modifications. AAV6.2, an AAV6 F129L point mutant, was demonstrated by Limberis et al. to be a 2-fold more efficient transducer of the mouse nose, airways and alveolar cells than AAV6 [5]. Similarly, when delivered intravenously to mice, AAV6.2 mediated 2-fold greater serum concentrations of human alpha-1 antitrypsin (hA1AT) than AAV6 [6]. Moreover, intramuscular administration of the same AAV6.2-hA1AT vector mediated higher serum levels of hA1AT than AAV6 or AAV9 [6]. Also, F129L is a naturally occurring singleton residue in the majority of over 100 known primate AAV capsid sequences, and AAV5 and AAV6 are the only serotypes that encode a phenylalanine instead of a leucine at this position [6].

AAV capsids are prone to phosphorylation of tyrosine residues by epidermal growth factor receptor protein tyrosine kinase (EGFR-PTK), leading to alternative cellular trafficking, ubiquitination and degradation [7, 8]. Mutation of various surface exposed tyrosine residues on AAV capsids has been shown to obstruct ubiquitin-mediated degradation of intracellular vector, thereby leading to more robust transgene expression [9]. Tyrosine to phenylalanine mutations introduced at positions 444 and 730 in the AAV2 capsid yielded 9- and 11-fold greater expression in vitro and 13- and 29-fold greater hepatocyte transduction in mice, respectively [9]. A double AAV2 Y444F+Y730F mutant generated significantly greater hepatocyte transduction in vivo than either of the singleton mutants [10]. Similar single tyrosine mutations have been introduced into corresponding positions in AAV6, AAV8 and AAV9 capsids with success in transducing various tissues.

SUMMARY

The present inventors engineered a triple mutant AAV6 capsid, termed AAV6.2FF, encoding F129L, Y445F and Y731F point mutations, which was demonstrated to be superior to the parental capsid in terms of muscle and airway transgene expression kinetics in a mouse model. Further, the present disclosure shows that AAV-mediated expression of non-neutralizing mAbs 5D2 or 7C9 encapsidated by AAV6.2FF confer 100% protection against Ebola virus infection when administered as monotherapies seven days prior to challenge, while neutralizing mAb 2G4 was 83% protective. In addition, the present disclosure shows a two-component cocktail of AAV-2G4 and AAV-5D2 provided complete protection when administered seven days prior to challenge and can protect a subject with as little as a three-day lead-time. Subjects were fully protected from Ebola challenge five months after receiving a single IM injection of AAV-2G4, AAV-5D2, or a double injection of the two. These findings demonstrate that AAV6.2FF-mediated expression of neutralizing or non-neutralizing mAbs when administered as early as seven days or as late as five months prior to exposure can prevent Ebola virus mortality in a mouse model.

Accordingly, the present disclosure provides a recombinant adeno-associated viral (rAAV) particle comprising a mutated capsid protein encapsidating a rAAV vector genome, wherein the mutated capsid protein comprises amino acid substitutions at amino acids 129, 445, and 731 of the AAV6 capsid protein sequence as set forth in SEQ ID NO:1.

In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding a therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding a therapeutic agent in muscle, airway, liver, central nervous system, retina or lung cells. In one embodiment, the therapeutic agent is a polypeptide, a therapeutic protein, an antigen, an antibody, or an antigen binding fragment, or a combination thereof. In another embodiment, the antibody comprises a monoclonal, polyclonal, chimeric, humanized antibody, a fragment thereof, or a combination thereof. In another embodiment, the antigen binding fragment is a Fab, Fabθ, F(ab')2, scFv, dsFv, ds-scFv, dimer, minibody, diabody, or multimer thereof or bispecific antibody fragment, or a combination thereof. In a further embodiment, the monoclonal antibody is 1H3, 2G4, 4G7, 5D2, 7C9, 100, 114, CA45, ADI-15878, FVM02p, FVM04, BDBV223, or a fragment thereof, or a combination cocktail thereof, against Ebola virus, or MR72, MR82, MR78, or MR191, or a combination thereof, against Marburg virus. In a further embodiment, the monoclonal antibody is 100 or a fragment thereof against Ebola virus, or MR191 or a fragment thereof against Marburg virus. In a further embodiment, the monoclonal antibody is 100 or a fragment thereof against Ebola virus. In a further embodiment, the monoclonal antibody is MR191 or a fragment thereof against Marburg virus.

In an embodiment, the particle further comprises a nucleotide sequence encoding a marker, optionally luciferase. The skilled person can readily recognize that many markers known in the art can be used, for example, fluorescent proteins such as GFP and RFP, or alkaline phosphatase. In another embodiment, the rAAV particle is comprised in a pharmaceutical composition that includes a pharmaceutically acceptable diluent, buffer, carrier, or excipient.

The present disclosure also provides a method of treating or preventing an infectious, acquired or genetic disease in a subject in need thereof, involving administering at least one rAAV particle, wherein the rAAV particle comprises a mutated capsid protein encapsidating a rAAV vector genome, wherein the rAAV vector genome comprises at least one heterologous nucleic acid segment flanked by AAV ITRs encoding a therapeutic agent operably linked to a promoter capable of expressing the segment in a host cell, wherein the mutated capsid protein comprises amino acid substitutions at amino acids 129, 445, and 731 of the AAV6 capsid protein sequence as set forth in SEQ ID NO:1, and wherein the therapeutic agent treats or prevents the infectious, acquired or genetic disease in the subject in need thereof. In one embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells.

Also provided is use of at least one rAAV particle for treating or preventing an infectious, acquired or genetic disease in a subject in need thereof, wherein the rAAV particle comprises a mutated capsid protein encapsidating a rAAV vector genome, wherein the rAAV vector genome comprises at least one heterologous nucleic acid segment flanked by AAV ITRs encoding a therapeutic agent operably linked to a promoter capable of expressing the segment in a host cell, and wherein the mutated capsid protein comprises amino acid substitutions at amino acids 129, 445, and 731 of the AAV6 capsid protein sequence as set forth in SEQ ID NO:1. In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells.

Further provided is use of at least one rAAV particle in the manufacture of a medicament for treating or preventing an infectious, acquired or genetic disease in a subject in need thereof, wherein the rAAV particle comprises a mutated capsid protein encapsidating a rAAV vector genome, wherein the rAAV vector genome comprises at least one heterologous nucleic acid segment flanked by AAV ITRs encoding a therapeutic agent operably linked to a promoter capable of expressing the segment in a host cell, and wherein the mutated capsid protein comprises amino acid substitutions at amino acids 129, 445, and 731 of the AAV6 capsid protein sequence as set forth in SEQ ID NO:1. In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells.

Even further provided is at least one rAAV particle for use in treating or preventing an infectious, acquired or genetic disease in a subject in need thereof, wherein the rAAV particle comprises a mutated capsid protein encapsidating a rAAV vector genome, wherein the rAAV vector genome comprises at least one heterologous nucleic acid segment flanked by AAV ITRs encoding a therapeutic agent operably linked to a promoter capable of expressing the segment in a host cell, and wherein the mutated capsid protein comprises amino acid substitutions at amino acids 129, 445, and 731 of the AAV6 capsid protein sequence as set forth in SEQ ID NO:1. In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells.

In an embodiment, the infectious disease is selected from the group consisting of viral diseases such as viral hemorrhagic fevers, Ebola, Marburg virus disease, gastroenteritis, dengue fever, West Nile fever, yellow fever, influenza, respiratory syncytial virus disease, Lassa fever, rabies, smallpox, cowpox, horsepox, monkeypox, Hentavirus pulmonary syndrome, Hendra virus disease, human immunodeficiency virus disease and acquired immunodeficiency disease syndrome, Hepatitis, Zika fever, optionally Ebola or Marburg virus disease, and bacterial diseases including drug resistant bacterial diseases such as tuberculosis and methicillin-resistant *Staphylococcus aureus* infection, and drug resistant parasitic diseases such as malaria. In another embodiment, the subject is human. In another embodiment, the at least one rAAV particle is administered or co-administered intravenously, intranasally, intratracheally, intramuscularly, or via aerosol. In an embodiment, the at least one rAAV particle is delivered to lung cells or tissues.

In one embodiment, the therapeutic agent remains in the serum of the subject for at least 2, 4, 8, 10, 12, 14, 16 or 18 weeks, optionally at least 18 weeks, up to 26, 28, 30, 32, or 34 weeks. In another embodiment, the therapeutic agent remains in the serum of the subject for up to 34 weeks. In another embodiment, the subject is protected from Ebola from 3, 7 or 14 days post administration to at least 3 weeks, or 1, 2, 3, 4, or 5 months, optionally at least 5 months.

The present disclosure also provides a nucleic acid molecule comprising a nucleotide sequence encoding a mutated AAV capsid protein, wherein the mutated AAV capsid protein comprises amino acid substitutions at amino acids 129, 445, and 731 of the AAV6 capsid protein sequence as set forth in SEQ ID NO:1.

Further provided is a method of producing a protein in vivo in a subject, comprising delivering or introducing into the subject a rAAV particle comprising a mutated capsid protein encapsidating a rAAV vector genome, wherein the rAAV vector genome comprises at least one heterologous nucleic acid segment flanked by AAV ITRs encoding the protein operably linked to a promoter capable of expressing the segment in vivo in the subject, and wherein the mutated capsid protein comprises amino acid substitutions at amino acids 129, 445, and 731 of the AAV6 capsid protein sequence as set forth in SEQ ID NO:1.

Other features and advantages of the present disclosure will become apparent from the following detailed description. It should be understood, however, that the detailed description and the specific Examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

Embodiments are described below in relation to the drawings in which:

FIGS. 1A-1D show heparin binding and transduction profiles of AAV6 and AAV6.2FF in vitro. FIG. 1A shows the distribution of AAV vector genomes following heparin binding assay (n=3). FT—flow though, W1—wash 1, W2—wash 2, E-elution. FIG. 1B shows AAV6, AAV6.2FF or AAV9 encoding luciferase were added at an MOI of 2000 and incubated for 72 hours prior to luciferase quantification to determine transduction efficiency. FIG. 1C shows the AAV binding and FIG. 1D shows the internalization of AAV vectors over various contact times in HeLa cells. Multiple t-tests compared AAV6.2FF mediated luciferase expression to AAV6 and AAV9. *p<0.05, p<0.01, *p<0.001.

FIG. 3A shows the quantification of luciferase expression in the muscle and lung 24 hours following intramuscular or intranasal delivery, respectively. Representative images demonstrating pattern and intensity of luciferase expression in (FIG. 3B) the muscle or (FIG. 3C) the lungs.

FIG. 4A and FIG. 4C show the quantification of luciferase signal on days 1, 3, 7, 14, 21, 28, 56 and 112 post AAV delivery. Paired t-tests were used to calculate significance, ***p<0.001. FIG. 4B shows images demonstrating luciferase expression on day 3 and 14 post AAV delivery to the gastrocnemius muscle.

FIGS. 5A-5H show gross AP staining of AAV6 and AAV6.2FF transduced nose and lungs. $1\times10^{11}$ vg of AAV6- or AAV6.2FF-Alkaline phosphatase (AP) was delivered intranasally to C57BL/6 mice (n=4/group) and tissues were harvested and stained after 3 weeks. Representative images of (FIG. 5A, FIG. 5E) the nose, and (FIGS. 5B-5D, FIGS. 5F-5H) lung lobes for both vectors are shown.

FIG. 6C and FIG. 6F show the demonstration of transduction of airway cells.

FIG. 7A shows the qPCR quantification of the AAV genome copy number per ng of total DNA extracted from paraffin embedded lung tissue. FIG. 7B shows the quantification of the AP transgene present in unfixed lung tissue. Dashed line indicates the threshold of detection for this assay.

FIG. 8A shows the in vivo luciferase images were obtained on 0, 1, 3, 7 and 14 days post AAV (dpa) administration. FIG. 8B shows the relative photon emission (p/s/cm²/sr) produced by luciferase from the muscle of each serotype of AAV was quantified at various time points from 1 to 56 dpi. Multiple t-tests were used to compare each time point. *Indicates AAV6.2FF is significant over all other capsids, p<0.05, and # indicates AAV6.2FF is significant over AAV8, AAV9 and AAV-DJ, p<0.05.

FIGS. 13A and 13B show AAV6.2FF-mediated mAb expression profiles in mice following intranasal administration. C57BL/6 mice (n=3/group) received $2 \times 10^{11}$ vg of (FIG. 13A) AAV-2G4 or (FIG. 13B) AAV-5D2 by a modified intranasal instillation as described in Limbris et al [5]. Serum was collected and analyzed at a dilution of 1:100 for EBOV GP binding activity by ELISA.

FIG. 16A shows Kaplan-Meyer survival plots of AAV6.2FF-2G4, AAV6.2FF-5D2, AAV6.2FF-7C9 monotherapies and FIG. 16B shows the averaged mouse group weights. Survival of treated groups was compared to the mock group using the Mantel-Cox log rank test (p=0.0009 for 2G4, 0.0005 for 5D2 and 7C9). FIG. 16C shows Kaplan-Meyer survival plots of AAV6.2FF-2G4/AAV6.2FF-5D2 cocktail survival plots at various lead-times between AAV administration and MA-EBOV challenge and FIG. 16D shows the averaged mouse group weights. Survival of treated groups was compared to the mock group using the Mantel-Cox log rank test (p=0.005 for 14 and 7 days, 0.2801 for 3 days and >0.9999 for 1 day and same day).

FIG. 17A shows Kaplan-Meyer survival plots of AAV6.2FF-2G4, AAV6.2FF-5D2, and AAV6.2FF-2G4/AAV6.2FF-5D2 cocktail and FIG. 17B shows the averaged mouse group weights.

FIG. 21C shows the fold change in pre to post challenge reciprocal anti-GP titers at each dose. FIG. 21D shows the serum samples from 28 days post challenge were analyzed at a 1:100 dilution by EBOV VP40 ELISA.

FIG. 22A shows the schematic of experimental design. BALB/c mice were administered $1 \times 10^{11}$ vg of AAV6.2FF-2G4/AAV6.2FF-5D2 IM 14 days prior to primary sub-lethal exposure to 600 HA units of influenza A virus (strain PR8) by IP injection. FIG. 22B shows the reciprocal EBOV GP titers from serum samples from AAV6.2FF-2G4/AAV6.2FF-5D2 or PBS treated groups. FIG. 22C shows the reciprocal HA titers following primary and secondary exposure to 600HA units of influenza A virus (strain PR8) in mice treated with AAV6.2FF-2G4/AAV6.2FF-5D2 or PBS. FIG. 22D shows the weight change in mice following primary influenza A virus (plotted as group averages).

FIGS. 23A-23D show AAV6.2FF-100 mediates complete protection from Ebola virus challenge. FIG. 23A shows the human IgG concentrations in the serum of BALB/c mice (n=4) that received $5 \times 10^9$ vg of AAV6.2FF-100 IM. FIG. 23B shows the BALB/c mice (n=8/group) were administered various doses of AAV6.2FF-100 IM. 28 days post-AAV administration mice were challenged with $1000 \times LD_{50}$ MA-EBOV and monitored for (FIG. 23B) survival and (FIG. 23C) weight loss (resulted from individual mice plotted). **p<0.0001, p<0.01, *p<0.05. FIG. 23D shows the serum concentrations of human IgG were quantified immediately prior to challenge for the groups treated with doses of $1 \times 10^{11}$ vg and $5 \times 10^{10}$ vg. Mice with human IgG concentrations below the dotted line succumbed to MA-EBOV challenge.

FIGS. 24A and 24B show post-challenge protection mediated by AAV6.2FF-2G4/AAV6.2FF-5D2 and AAV6.2FF-100. BALB/c mice (n=8/group) were challenged with a reduced dose of $100 \times LD_{50}$ MA-EBOV IP and were subsequently injected IM with $1 \times 10^{11}$ vg of the AAV6.2FF-2G4/AAV6.2FF-5D2 cocktail or $5 \times 10^{10}$ vg of AAV6.2FF-100 and monitored for 28 days for (FIG. 24A) survival and (FIG. 24B) weight loss (results from individual mice plotted). **p<0.01, *p<0.05.

FIG. 25A shows the serum human IgG concentrations in BALB/c mice (n=4) that received $6 \times 10^{10}$ vg of AAV6.2FF-MR191 IM. FIGS. 25B-25D show BALB/c mice (n=8/group) were administered a low ($1 \times 10^{10}$ vg) or a high ($1 \times 10^{11}$ vg) dose of AAV6.2FF-MR191 IM. 28 days post-AAV administration mice were challenged with $1000 \times LD_{50}$ MA-MARV and monitored for (FIG. 25B) survival and (FIG. 25C) weight loss (results from individual mice plotted). ****p<0.0001. FIG. 25D shows the serum concentrations of human IgG were quantified immediately prior to challenge.

FIG. 26A shows the schematic of experimental design. BALB/c mice (n=4/group) received an IM injection of $1 \times 10^{11}$ vg of AAV6.2FF-, AAV6-, AAV8-, AAV9- or AAV-DJ-Luciferase in the left flank and were monitored for luciferase expression for 205 days. All mice were then injected in the right flank with $1 \times 10^{11}$ vg of AAV6.2FF-Luciferase and transgene expression was quantified 28 days later. FIGS. 26B-26F show the quantification of luciferase expression in the left calf muscle 205 days post-primary vector injection as well as the transgene expression in both the left and right flank 28 day following secondary AAV6.2FF-Luciferase injection. Representative images of mice 28 days post-secondary AAV6.2FF-Luciferase administration demonstrate transgene expression in both flanks. Graphs show group means and error bars represent standard deviation. One-way ANOVA was used to determine statistical difference between the primary and secondary signal 28 days post-secondary AAV6.2FF-Luciferase injection; One-way ANOVA was used to determine statistical difference between the primary and secondary signal 28 days post-secondary AAV6.2FF-Luciferase injection; p<0.01, *p<0.001.

FIG. 27A shows the schematic of experimental design. BALB/c mice (n=4) were injected with $6 \times 10^{10}$ g of AAV6.2FF-MR191 IM (left flank) and serum human IgG concentrations were monitored for 70 days. On day 82, these mice were injected with $3 \times 10^{10}$ vg of AAV6.2FF-100 in the right calf muscle and human IgG concentrations were evaluated until day 154. FIG. 27B shows the human IgG concentrations in treated mice. FIG. 27C shows MARV GP and EBOV GP concentrations determined by ELISA in select pre- and post-boost serum samples. FIG. 27D shows endogenous antibody response against the AAV6.2FF capsid and the mAb 100 antibody evaluated by ELISA. Graphs show group means, as well as individual data points for each mouse and error bars represent standard deviation.

FIG. 28A shows the schematic of AAV6.2FF vectors expressing Luciferase or mCherry reporter genes. FIG. 28B shows the study design to determine lung tissue targeting by AAV6.2FF-Luciferase. FIG. 28C shows IVIS imaging of transgenic SPB mice either untreated or intratracheally injected with AAV6.2FF-Luciferase. FIG. 28D shows the quantification of IVIS images. FIG. 28E shows the mean weight measurements from all mice from (FIG. 28C). FIG. 28F shows the study design to determine whether AT2 cells were targeted by AAV6.2FF-mCherry. FIG. 28G shows epifluorescence image of Pro-SPC, mCherry and DAPI from lung sections of SPB deficient mice 5 weeks after intratracheal injection of AAV6.2FF-mCherry+Bovine Lipid Extract Surfactant (BLES). Arrows point to lung cells expressing Pro-SPC which indicated that they were AT2 cells which also expressed mCherry produced from AAV6.2FF. FIG. 28H shows the schematic of codon optimized murine SPB cDNA in expression plasmid. FIG. 28I shows the Western blot of HEK293 cells transduced with AAV6.2FF-SPB (MOI=20,000; lane 2, AAV-SPB; i.e. AAV-SPB-myc vector) or transiently transfected with the SPB expression plasmid (lane 3, SPB-myc; i.e. plasmid genome used to generate the AAV-SPB-myc vector). "Pre-SPB" denotes the non-processed form of myc-SPB (myc tag on the 3' end), prior to SPB being cleaved by multiple proteases into its mature form.

FIG. 29A shows the study design to determine whether AAV6.2FF-SPB improved lung structure and function. "On Dox" denotes doxycycline feed was not removed during the course of the study. FIG. 29B shows the percentage change in body weight over 4 weeks following AAV injection. FIG. 29C shows the percentage change in body weight over 3 to 4 days following doxycycline removal. FIG. 29D shows the representative macroscopic lung images 3 to 4 days following doxycycline removal. FIG. 29E shows the representative Hematoxylin and Eosin (H&E; 20×) and Wright-Giemsa Jenner (WGJ; 40×) staining of paraffin embedded whole left lungs following doxycycline removal. FIG. 29F shows the representative epi-fluorescence images of Pro-SPC, SPB, and DAPI from OCT frozen right lung sections following doxycycline removal. Arrows indicate SPB staining. FIG. 29G shows the representative TEM images of two different fields of view of AT2 cells following doxycycline removal. White arrows indicate lamellar bodies and black arrows indicate mitochondria. Scale bars represent 2 μm in 10,000× images and 500 nm in 20,000× image. N, nucleus. FIG. 29H shows the pressure volume curve following doxycycline removal corrected for body weight (in mug). FIG. 29I shows % V10 corrected for body weight. FIG. 29J shows the total lung capacity corrected for body weight (in mug). FIG. 29K shows the residual Volume corrected for body weight (in mUg). FIG. 29L shows the compliance corrected for body weight (in mL/cmH$_2$O*g). All P values=ordinary one-way ANOVA with Tukey's multiple comparisons post hoc test; ns=not significant.

DETAILED DESCRIPTION

Figure 2:
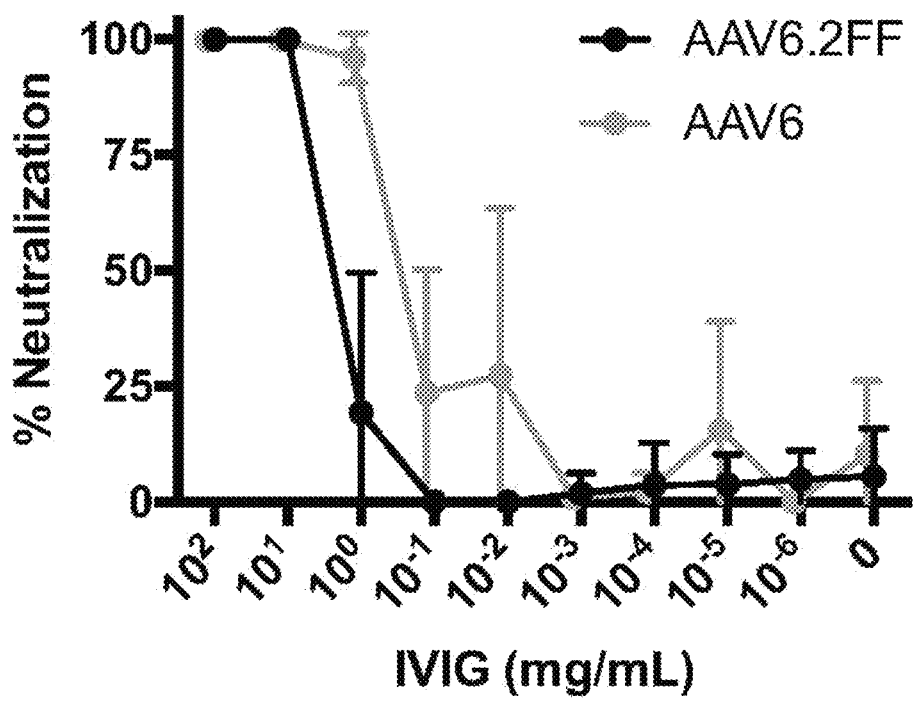
FIG. 2 shows intravenous immunoglobulin (IVIG) neutralization of AAV in vitro. AAV vector was incubated with 10-fold dilutions of IVIG for 1 hour at 37° C. prior to adding to HeLa cells. 72 hours later luciferase expression was quantified and the data is expressed as the percent AAV neutralization as compared to control virus incubated with PBS only (n=6).

Unless otherwise indicated, the definitions and embodiments described in this and other sections are intended to be applicable to all embodiments and aspects of the present disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

As used herein, the singular forms "a", "an" and "the" include plural references unless the content clearly dictates otherwise.

Compositions

The term "adeno-associated virus" (AAV), as used herein, includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV.

The genomic sequences of various AAV as well as the sequences of the ITRs, rep proteins, and capsid proteins are known in the art. Such sequences may be found in the literature or in public databases such as the GenBank database. See, e.g., GenBank Accession Numbers NC_002077, NC_001401, NC_001729, NC_001863, NC_001829, NC_001862, NC_000883, NC_001701, NC_001510, AF063497, U89790, AF043303, AF028705, AF028704, J02275, J01901, J02275, X01457, AF288061, AH009962, AY028226, AY028223, NC_001358, NC_001540, AF513851, AF513852, AY530579, AY631965, AY631966; the disclosures of which are incorporated herein in their entirety. For instance, the GenBank Accession Number for AAV6 is AF028704.1.

The present inventors have provided a rAAV particle with mutated capsid protein, where the AAV particle exhibits greater transduction of muscle, airway, liver, central nervous system, retina or lung cells compared to wild-type AAV. The present inventors have further provided methods of delivering a therapeutic agent to a muscle, airway, liver, central nervous system, retina or lung cell in a subject, and methods of treating or preventing an infectious, acquired or genetic disease, with said AAV particle.

Accordingly, herein provided is a recombinant adeno-associated viral (rAAV) particle comprising a mutated capsid protein encapsidating a rAAV vector genome, wherein the mutated capsid protein comprises amino acid substitutions at amino acids 129, 445, and 731 of the AAV6 capsid protein sequence as set forth in SEQ ID NO:1. In a specific embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2.

Amino acid sequences described herein are set out in Table 1.

TABLE 1

| Sequences | |
|---|---|
| SEQ ID NO: 1: amino acid sequence of parental AAV6 capsid protein | MAADGYLPDWLEDNLSEGIREWWDLKPGAPKPKA NQQKQDDGRGLVLPGYKYLGPFNGLDKGEPVNAA DAAALEHDKAYDQQLKAGDNPYLRYNHADAEFQE RLQEDTSFGGNLGRAVFQAKKRVLEPFGLVEEGA KTAPGKKRPVEQSPQEPDSSSGIGKTGQQPAKKR LNFGQTGDSESVPDPQPLGEPPATPAAVGPTTMA SGGGAPMADNNEGADGVGNASGNWHCDSTWLG DRVITTSTRTWALPTYNNHLYKQISSASTGASNDN HYFGYSTPWGYFDFNRFHCHFSPRDWQRLINNN WGFRPKRLNFKLFNIQVKEVTTNDGVTTIANNLTST VQVFSDSEYQLPYVLGSAHQGCLPPFPADVFMIPQ YGYLTLNNGSQAVGRSSFYCLEYFPSQMLRTGNN FTFSYTFEDVPFHSSYAHSQSLDRLMNPLIDQYLYY LNRTQNQSGSAQNKDLLFSRGSPAGMSVQPKNW LPGPCYRQQRVSKTKTDNNNSNFTWTGASKYNLN GRESIINPGTAMASHKDDKDKFFPMSGVMIFGKES AGASNTALDNVMITDEEEIKATNPVATERFGTVAVN LQSSSTDPATGDVHVMGALPGMVWQDRDVYLQG |

TABLE 1-continued

| | Sequences |
|---|---|
| | PIWAKIPHTDGHFHPSPLMGGFGLKHPPPQILIKNT PVPANPPAEFSATKFASFITQYSTGQVSVEIEWELQ KENSKRWNPEVQYTSNYAKSANVDFTVDNNGLYT EPRPIGTRYLTRPL |
| SEQ ID NO: 2: amino acid sequence of the mutated AAV6 capsid protein (AAV6.2FF) | MAADGYLPDWLEDNLSEGIREWWDLKPGAPKPKA NQQKQDDGRGLVLPGYKYLGPFNGLDKGEPVNAA DAAALEHDKAYDQQLKAGDNPYLRYNHADAEFQE RLQEDTSFGGNLGRAVFQAKKRVLEPLGLVEEGA KTAPGKKRPVEQSPQEPDSSSGIGKTGQQPAKKR LNFGQTGDSESVPDPQPLGEPPATPAAVGPTTMA SGGGAPMADNNEGADGVGNASGNWHCDSTWLG DRVITTSTRTWALPTYNNHLYKQISSASTGASNDN HYFGYSTPWGYFDFNRFHCHFSPRDWQRLINNN WGFRPKRLNFKLFNIQVKEVTTNDGVTTIANNLTST VQVFSDSEYQLPYVLGSAHQGCLPPFPADVFMIPQ YGYLTLNNGSQAVGRSSFYCLEYFPSQMLRTGNN FTFSYTPEDVPFHSSYAHSQSLDRLMNPLIDQYLYF LNRTQNQSGSAQNKDLLFSRGSPAGMSVQPKNW LPGPCYRQQRVSKTKTDNNNSNFTWTGASKYNLN GRESIINPGTAMASHKDDKDKFFPMSGVMIFGKES AGASNTALDNVMITDEEEIKATNPVATERFGTVAVN LQSSSTDPATGDVHVMGALPGMVWQDRDVYLQG PIWAKIPHTDGHFHPSPLMGGFGLKHPPPQILIKNT PVPANPPAEFSATKFASFITQYSTGQVSVEIEWELQ KENSKRWNPEVQYTSNYAKSANVDFTVDNNGLYT EPRPIGTRFLTRPL |
| SEQ ID NO: 3: nucleotide sequence of monoclonal antibody 1H3 heavy chain | TGGGGCAGAGCTTGTGAAGCCAGGGGCCTCAGT CAAGTTGTCCTGCACAGCTTCTGGCTTCAACATT AAAGACACCTATATACATTGGGTGAAACAGGGGC CTGAACAGGGCCTGGAGTGGATTGGAAGGATTG ATCCTGCGAATGGTAATACTAAATATGACCCGAA GTTCCAGGGCAAGGCCACTATCACAGCAGACAC ATCCTCCAATACAGCCTACCTGCAGCTCAGCGG CCTGACATCTGAGGACACTGCCGTCTATTACTGT GCTAGGGAGTCGAGGATATCTACTATGCTTACGA CGGGGTACTTTGACTACTGGGGCCAAGGCACCA CTCTCACAGTCTCCTCAGCCAAAACAACAGCCCC ATCG |
| SEQ ID NO: 4: nucleotide sequence of monoclonal antibody 1H3 light chain | GCAATCATGTCTGCATCTCCAGGGGAGAAGGTC ACCATGACCTGCAGTGCCAGCTCAAGTGTAAGTT ACATGTACTGGTACCAGCAGAAGCCAGGATCCT CCCCCAGACTCCTGATTTATGACACATCCAACCT GGCTTCTGGAGTCCCTGTTCGCTTCAGTGGCAG TGGGTCTGGGACCTCTTACTCTCTCACAATCAGC CGAATGGAGGCTGAAGATGCTGCCACTTATTACT GCCAGCAGTGGAGTAGTTACCCGTACACGTTCG GAGGGGGGACCAAGCTGGAAATAAAACGGGCTGAT |
| SEQ ID NO: 5: nucleotide sequence of monoclonal antibody 2G4 heavy chain | TGGAGGAGGCTTGATGCAACCTGGAGGATCCAT GAAACTCTCCTGTGTTGCCTCAGGATTCACTTTC AGTAACTACTGGATGAACTGGGTCCGCCAGTCT CCAGAGAAGGGGCTTGAGTGGGTTGCTGAAATT AGATTGAAATCTAATAATTATGCAACACATTATGC GGAGTCTGTGAAAGGGAGGTTCACCATTTCAAG AGATGATTCCAAAAGGAGTGTCTACCTGCAAATG AATACCTTAAGAGCTGAAGACACTGGCATTTATT ACTGTACCCGGGGGAATGGTAACTACAGGGCTA TGGACTACTGGGGTCAAGGAACCTCAGTCACCG TCTCCTCAGCCAAAACAACACCCCCATCA |
| SEQ ID NO: 6: nucleotide sequence of monoclonal antibody 2G4 light chain | GCCTCCCTATCTGTATCTGTGGGAGAAACTGTCT CCATCACATGTCGAGCAAGTGAGAATATTTACAG TAGTTTAGCATGGTATCAGCAGAAACAGGGAAAA TCTCCTCAGCTCCTGGTCTATTCTGCAACAATCT TAGCAGATGGTGTGCCATCAAGGTTCAGTGGCA GTGGATCAGGCACTCAGTATTCCCTCAAGATCAA CAGCCTGCAGTCTGAAGATTTTGGGACTTATTAC TGTCAACATTTTTGGGGTACTCCGTACACGTTCG GAGGGGGGACCAAGCTGGAAATAAAACGGGCTG T |

TABLE 1-continued

| | Sequences |
|---|---|
| SEQ ID NO: 7:<br>nucleotide sequence<br>of monoclonal<br>antibody 4G7 heavy<br>chain | TGGACCTGAGCTGGAGATGCCTGGCGCTTCAGT<br>GAAGATATCCTGCAAGGCTTCTGGTTCCTCATTC<br>ACTGGCTTCAGTATGAACTGGGTGAAGCAGAGC<br>AATGGAAAGAGCCTTGAGTGGATTGGAAATATTG<br>ATACTTATTATGGTGGTACTACCTACAACCAGAA<br>ATTCAAGGGCAAGGCCACATTGACTGTGGACAA<br>ATCCTCCAGCACAGCCTACATGCAGCTCAAGAG<br>CCTGACATCTGAGGACTCTGCAGTCTATTACTGT<br>GCAAGATCGGCCTACTACGGTAGTACTTTTGCTT<br>ACTGGGGCCAAGGGACTCTGGTCACTGTCTCTG<br>CAGCCAAAACAACAGCCCCATCG |
| SEQ ID NO: 8:<br>nucleotide sequence<br>of monoclonal<br>antibody 4G7 light<br>chain | GCCTCCCTATCTGCATCTGTGGGAGAAACTGTCA<br>CCATCACATGTCGAGCAAGTGAGAATATTTACAG<br>TTATTTAGCATGGTATCAGCAGAAACAGGGAAAA<br>TCTCCTCAGCTCCTGGTCTATAATGCCAAAACCT<br>TAATAGAGGGTGTGCCATCAAGGTTCAGTGGCA<br>GTGGATCAGGCACACAGTTTTCTCTGAAGATCAA<br>CAGCCTGCAGCCTGAAGATTTTGGGAGTTATTTC<br>TGTCAACATCATTTTGGTACTCCATTCACATTCGG<br>CTCGGGGACAGAGTTGGAAATAAAACGGGCTGA<br>T |
| SEQ ID NO: 9:<br>nucleotide sequence<br>of monoclonal<br>antibody 5D2 heavy<br>chain | GGGACCTGGCCTGGTGAGACCTTCTCAGTCTCT<br>GTCCCTCACCTGCACTGTCACTGGCTACTCAATC<br>ACCAGTGATTATGCCTGGAACTGGATCCGGCAG<br>TTTCCAGGAAACAAACTGGAGTGGCTGGGCTATA<br>TAACCAACACTGGTAGCACTGGCTTCAACCCATC<br>TCTCAAAAGTCGAATCTCTATCACTCGAGACACA<br>TCCAAGAACCAGTTCTTCCTGCAGTTGATTTCTG<br>TGACTACTGAGGACACAGCCACATATCACTGTGC<br>AAGGGGCCTTGCTTACTGGGGCCAAGGGACTCT<br>GGTCACTGTCTCTGCAGCCAAAACAACAGCCCC<br>ATCG |
| SEQ ID NO: 10:<br>nucleotide sequence<br>of monoclonal<br>antibody 5D2 light<br>chain | CTCACTTTGTCGGTTACCATTGGACAACCAGCCT<br>CCATCTCTTGCAAGTCAAGTCAGAGCCTCTTAGA<br>TAGTGATGGAAAGACATATCTGAATTGGTTGTTA<br>CAGAGGCCAGGCCAGTCTCCAAAGCGCCTAATC<br>TATCTGGTGTCTAAACTGGACTCTGGAGTCACTG<br>ACAGGTTCACTGGCAGTGGATCAGGGACAGATT<br>TCACACTGAAAATCAGCAGAGTGGAGGCTGAGG<br>ATTTGGGAGTTTATTATTGTTGGCAAGGTACACA<br>CTCTCCATTCACGTTCGGCTCGGGGACAAAGTT<br>GGAAATAAAACGGGCTGAT |
| SEQ ID NO: 11:<br>nucleotide sequence<br>of monoclonal<br>antibody 7C9 heavy<br>chain | TGGGGCAGAGCTTGTGAAGCCAGGGGCCTCAGT<br>CAAGTTGTCCTGCACAGCTTCTGGCTTCAACATT<br>AAAGACACCTATATGCACTGGGTGAAGGAGAGG<br>CCTGACAAGGGCCTGGAGTGGATTGGAAGGATT<br>GATCCAGCGAATGGTAATACTAAATGACTCGA<br>GGTTTCAGGGCAAGGCCACTATAACAGCAGACA<br>CATCCTCCAACACAGCCTACCTGCAGCTCAGCA<br>GCCTGACATCTGAGGACACTGCCGTCTATTACTG<br>TGCTAGAAGGATCTACTTTGGTAAGGGCTTTGAC<br>TTTTGGGGCCAAGGCACCACTCTCACAGTCTCCT<br>CAGCCAAAACAACAGCCCCATCG |
| SEQ ID NO: 12:<br>nucleotide sequence<br>of monoclonal<br>antibody 7C9 light<br>chain | TCCTCCCTGAGTGTGTCAGCAGGAGAGAAGGTC<br>ACTATGAGCTGCAAGTCCAGTCAGAGTCTGTTTA<br>ACAGTGGAGATCAAAAGAACTACTTGGCCTGGTA<br>CCAGCAGAAACCAGGGCAGCCTCCTAAACTGTT<br>GATCTACGGGGCATCCACTAGGGAATCTGGGGT<br>CCCTGATCGCTTCACAGGCAGTGGATCTGGAAC<br>CGATTTCACTCTTACCATCAGCAGTGTGCAGGCT<br>GAAGACCTGGCAGTTTATTACTGTCAGAATGATC<br>AATTTTATCCTCCCACGTTCGGTGATGGGACCAA<br>GCTGGACCTGAAACGGGCTGAT |
| SEQ ID NO: 13:<br>nucleotide sequence<br>of monoclonal<br>antibody 100 heavy<br>chain | CAGGTGCAACTTCAGGAGTCAGGGCCTGGCCTC<br>GTCAAACCAAGCGATACACTGAGTTTGACTTGCA<br>CAGTGAGTGGGGGTAGTTTGTCTAGTTTCTATTG<br>GTCTTGGATTCGGCAACCCCCCGGCAAAGGTCT<br>TGAGTGGATAGGATACATCTACTACTCAGGGTCC<br>CCCAATTACTCACCTTCCCTGGAATCTAGGGTTA<br>CTATGTCCGTGGACACAACCCGAAATCAAATATC<br>CTTGAAGCTTGACTCCGTGACAGCCGCAGACAC<br>CGCCGTTTACTACTGCGTCCGAGCATCCCGCTC |

TABLE 1-continued

| | Sequences |
|---|---|
| | CTATTATTGGGGTAGCTATCGACCAACTGCTTTT<br>GATTCTTGGGGACAGGGGACACTTGTAACTGTCT<br>CAAGC |
| SEQ ID NO: 14:<br>nucleotide sequence<br>of monoclonal<br>antibody 100 light<br>chain | TCTTATGAACTCACTCAGCCACTTTCTGTCAGTG<br>TCAGCCCAGGTCAGACCGCCATATTTACCTGCA<br>GTGGCGATAACTTGGGCGACAAATACGTGTGTT<br>GGTTTCAGCAACGGCCCGGCCAGTCACCCATGC<br>TCCTTATCTATCAAGACAACAAGCGACCTTCAGG<br>CATCCCCGAGCGGTTTAGTGGGTCTAACTCTGG<br>GAACACCGCTACATTGACTATTAGTGGAACTCAG<br>TCAACCGATGAAGCCGACTATTACTGCCAAACTT<br>GGGATTCCACCGTAGTTTTCGGCGGCGGAACTA<br>AGTTGACAGTGTTG |
| SEQ ID NO: 15:<br>nucleotide sequence<br>of monoclonal<br>antibody 114 heavy<br>chain | GAGGTGCAACTGGTCGAATCTGGTGGAGGACTT<br>ATCCAGCCTGGTGGCAGCCTGAGACTTTCTTGC<br>GCAGCTAGTGGATTTGCTTTGAGGATGTATGACA<br>TGCATTGGGTACGACAGACAATAGACAAACGGTT<br>GGAATGGGTTTCTGCTGTAGGCCCTAGCGGAGA<br>CACCTACTACGCAGACAGCGTGAAGGGTAGGTT<br>TGCAGTTTCACGGGAGAACGCTAAGAACAGCCT<br>CTCACTTCAAATGAATAGCCTCACCGCTGGCGAC<br>ACAGCAATCTACTACTGTGTAAGAAGTGATAGGG<br>GTGTTGCCGGGCTGTTTGACAGTTGGGGACAGG<br>GTATTTTGGTAACCGTGAGCAGT |
| SEQ ID NO: 16:<br>nucleotide sequence<br>of monoclonal<br>antibody 114 light<br>chain | GACATACAGATGACCCAAAGCCCTTCATCCCTCT<br>CTGCTTCTGTAGGTGACAGGATTACAATCACCTG<br>CCGCGCAAGTCAGGCTTTTGACAACTATGTGGC<br>ATGGTATCAGCAACGACCAGGGAAGGTCCCAAA<br>ATTGCTGATCTCCGCTGCCTCCGCTCTTCACGCA<br>GGAGTCCCTTCTAGGTTTTCTGGATCAGGGTCC<br>GGTACTCACTTCACCCTCACTATATCAAGTCTCC<br>AACCTGAAGACGTGGCCACCTACTACTGCCAGA<br>ATTATAACAGTGCTCCACTTACTTTTGGTGGAGG<br>AACAAAGGTAGAGATAAAA |
| SEQ ID NO: 17:<br>nucleotide sequence<br>of monoclonal<br>antibody CA45 heavy<br>chain | CAAGTTCAATTGCAAGAGTGGGGGAGGGCCTG<br>GTTAAGCCCAGCGAAACTTTGAGCTTGACATGTG<br>CTGTGTATGGCGGCTCTATCAGTGGTTACTACCA<br>CTGGAATTGGATAAGGCTCCCCCCCGGCAAAGG<br>GCTCGAGTGGATCGGGAATATAGATGGTAACAG<br>CGCAAGTACAAATTACAATCCTTCTCTGAAGACC<br>CGAGTGACCATTAGCAAGGATACCAGCAAAAATC<br>AAATTAGTTTGAAAGTACGATCCTTGACTGCCGC<br>CGACACCGCCGTCTACTATTGCGCTAGGGACCC<br>TGGATTCACTATATTTGGAGTAGTTATCACATCAT<br>GGTCCGGCCTCGACTCTTGGGGTCAGGGGGCA<br>GTGGTGACAGTTTCATCT |
| SEQ ID NO: 18:<br>nucleotide sequence<br>of monoclonal<br>antibody CA45 light<br>chain | GATATACAGATGACACAAAGTCCCTCATCTTTGT<br>CAGCTTCTGTGGGGATACCGTTACTATTACTTG<br>TAGGGCATCCCAATCAATTTCTAATAATCTGGCA<br>TGGTATCAACAGCGCCCTAGAAGAGCCCCACAA<br>CTGCTGATCTACGCCGCCTCTAACCTTGCTTCAG<br>GTGTGCCCTCCCGATTTTCAGGATCAGGTTCAG<br>GGACAGATTTTACTCTCACAATTTCCTCTCTTCAA<br>GCAGAGGACTTTGCTGCTTACTACTGCCAGCAG<br>CATAATACTCTCCCTCTCACCTTTGGTGGTGGAA<br>CAAAAGTTGAGATTAAG |
| SEQ ID NO: 19:<br>nucleotide sequence<br>of monoclonal<br>antibody ADI-15878<br>heavy chain | CAAGTCCAACTGGTCCAATCAGGAGTGACCCTT<br>GTTCAACCTGGTGGGAGCCTTAGAGTTAGTTGTG<br>CAGCCAGCGGTTTTACCTTTAGTAGCTATGCTAT<br>GAGCTGGGTACGCCAAGCTCCTGGCAAGGGCCT<br>GGAGTGGGTAAGCGCTATCTCCGGTTTGGGGGG<br>TTCTACATACTACGCAGATTCAGTTAAGGGAAGG<br>TTCACTATTTCTCGGGATAACTCCAAAAACACACT<br>TTATCTTCAGATGAACTCTCTTCGCGCAGAAGAC<br>ACTGCTGTT |
| SEQ ID NO: 20:<br>nucleotide sequence<br>of monoclonal<br>antibody ADI-15878<br>light chain | GACATAGTGCTGACTCAGAGTCCTTCCACTCTTT<br>CAGCTAGTGTAGGGGACCGCGTCACAATAACAT<br>GCAGAGCTTCACAATCCATAAGCTCCTGGTTGGC<br>TTGGTACCAACAGAAGCCTGGGGAAGCTCCCAA<br>ACTCTTGATTAGCGACGCTTCAAGTTTGGAGTCA<br>GGGGTACCCTCAAGGTTCTCTGGCAGTGGGTCC |

TABLE 1-continued

Sequences

GGTACAGAATTTACCCTCACAATAAGCAGCTTGC
AACCTGACGACTTCGCTACATACTATTGTCAGCA
GTATTATAGTTCTCCAACCTTCGGAGGGGGTACC
AAAGTGGAAATTAAA

SEQ ID NO: 21:
nucleotide sequence
of monoclonal
antibody FVM02p
heavy chain

GAAGTTCAGTTGGTAGAGTCAGGCGGCGGATTG
GTGCAACCTGGTGGGTCCCTCAGATTGAGTTGT
GCCGCTTCCGGGTTTACAGGATTTACTTTTTCTG
ACTACGCATTCTATTGGGTGAGACAGGCACCTG
GAAAAGGTTTGGAATGGGTAGGATTCATTAGGG
GCAAGGCATACGGAGGTACAGCAGACTACGCCG
CTTCTGTTAAAGGAAGGTTCACCATTTCTCGAGA
TAATTCCAAAAACACTGCCTATTTGCAGATGAGC
TCTTTGAAGACA

SEQ ID NO: 22:
nucleotide sequence
of monoclonal
antibody FVM02p light
chain

GACATCGTTCTCACACAATCACCCCTCAGCTTGC
CCGTCACACCCGGCGAGCCAGCTAGTATCAGTT
GTAGGTCCTCTCAGAGTTTGCTGCACTCTGGGG
GTAAAACTTACCTCTATTGGTATCTTCAAAAGCCT
GGTCAGTCCCCCCAGCTTCTTATTCATGAAGTAT
CCAACAGAGCATCTGGAGTGCCTGATAGATTTTC
TGGTAGTGGTTCTGGAACTGATTTCACCTTGAAG
ATCAGCCGAGTGGAGGCCGAGGACGTGGGAGT
ATATTACTGCATGCAGGGAATACAGTTGCCTCTG
ACCTTTGGGGGAGGAACAAAAGTTGAGATAAAAC
GAACTGTA

SEQ ID NO: 23:
nucleotide sequence
of monoclonal
antibody FVM04
heavy chain

GAAGTGCAACTTGTCCAATCTGGGGGCGGCCTG
GTACAACCAGGCGGATCTATGCGGCTCTCATGC
GAGGCATCAGGACTGTCTCTCAGTGATTATTTTA
TGCATTGGGTCCGGCAGGCCCAGGGAAAAGGTT
TGGAGTGGATCGGTTTGATACAGACAAAGGCTTT
CACCTATAAAACCGAATACCCTGCTGCTGTTAAG
GGTCGCTTTACCATCTCACGGGACGATAGTAAGA
ACACTCTGTATTTGCAAATGTCTTCACTTAAGCCA
GAGGATACAGCATTGTACTACTGCATTGCCGTGA
CCCCCGACTTTTATTACTGGGGTCAGGGAGTGTT
GGTCACCGTATCTTCC

SEQ ID NO: 24:
nucleotide sequence
of monoclonal
antibody FVM04 light
chain

GACGTTGTTATGACCCAGTCCCCAAGTTTCCTGT
CTGCTAGTGTTGGCGATAGAGTAACTATCACCTG
TAGGGCTAGTCAAGACATAACCATAAATCTCAAT
TGGTTTCAGCATAAGCCTGGAAAGGCCCCAAAG
CGGCTGATCTACGTTGCATCCCGCTTGGAACGA
GGGGTGCCCAGTCGGTTCTCAGGAAGCGGCAG
CGGGACAGAATTTACTCTTACTATTTCAAGCCTT
CAGCCTGAAGATTTTGCCACATATTACTGTCAAC
AGTATAATAACTATCCCCTGACCTTTGGTCCTGG
GACAAAACTCGATATAAAGCGAACCGTA

SEQ ID NO: 25:
nucleotide sequence
of monoclonal
antibody BDBV223
heavy chain

GAAATTGTGATGACCCAGTCTCCAGCCATCATGT
CTGTGTCTCCAGGGAAAAGAGCCACCCTCTCCT
GCAGGGCCAGTCAGAGTGTCAGTAGCAACTTAG
CCTGGTACCAGCGGAAACCTGGCCAGGCTCCCA
GGCTCCTCATCTATGGTTCTTCCACCAGGGCCAC
TGGTATCCCAGCCAGGTTCAGTGGCAGTGGGTC
TGGGACAGAGTTCACTCTCACCATCAGCAGCCT
GCAGTCTGAGGATTTTGCAGTTTATTACTGTCTG
CAATATTATAACTGGCCTCGGACGTTCGGCCAAG
GGACCAAGGTGGAAATCAAA

SEQ ID NO: 26:
nucleotide sequence
of monoclonal
antibody BDBV223
light chain

CAGGTGCAGCTACAGCAGTGGGGCGCAGGACT
GTTGAAGCCTTCGGAGACCCTGTCCCTCACCTG
CGCTGTCTATGGTGGGTCCTTCACGACTACCTAC
TGGAATTGGATCCGCCAGCCCCCAGGGAAGGG
GCTGGAATGGATAGGGGAAGTCAATTATAGTGG
AAACGCCAACTACAACCCGTCCCTCAAGGGTCG
AGTCGCCATATCAGTGGACACATCCAAGAACCA
GTTCTCCCTGAGGTTGAACTCTGTGACCGCCGC
GGACACGGCTATATATTACTGTACGAGTCGCATA
CGTTCGCACATTGCCTACTCGTGGAAGGGGGAC
GTCTGGGGCAAAGGGACCACGGTCACCGTCTCC
TCA

TABLE 1-continued

| | Sequences |
|---|---|
| SEQ ID NO: 27:<br>nucleotide sequence<br>of monoclonal<br>antibody MR72 heavy<br>chain | CAGTTGCAACTTCAAGAGTCTGGTCCTGGCTTGG<br>TCAAACCAAGCGAGACTCTCAGCCTGACTTGTAC<br>TGTATCCGGTGACAGCATAAACAACACAAATTAT<br>TACTGGGCTTGGATCAGGCAGCCACCAGGGAAG<br>GGCCTTGAGTATATTGGTTCAATCTATTACTCTG<br>GTAGTACATACTATAACCCTAGCTTGAAGAGTAG<br>GGTAACTATGTCAGTGGATGCTAGTAAGAACCAG<br>TTCTCACTGAGACTGTCCTCTGTCACTGCTGCTG<br>ACACTGCTGTGTACTACTGTGCTACCCACCCCAC<br>ACTCGGCGCTTTTGTATTGCTGTGGTTTGGTGCC<br>AACTTCGATCACTGGGGTCAGGGTACTTTGGTGA<br>CAGTGTCTAGC |
| SEQ ID NO: 28:<br>nucleotide sequence<br>of monoclonal<br>antibody MR72 light<br>chain | CAAGCCGTCGTCACACAACCCCCCTCAGTCAGC<br>GGAGCACCTGGTCAGCGGGTCACTATTAGCTGT<br>ACCGGCAGCAGTTCCAATATAGGCGCTAACTATG<br>ATGTGCATTGGTATCAACAGCTCCCTGGGACTGC<br>TCCTAAATTGCTGATGTATTCCAATACCAACAGA<br>CCATCCGGAGTTCCCGATAGGTTTAGTGGGTCC<br>AAGAGCGGAACCTCAGCTTCACTGGCAATTACC<br>GGGCTGCAAGCAGAAGACGAAGCTGACTATTAC<br>TGCCAAAGTTACGACAATAGTCTTAATAGCTGGG<br>TTTTTGGAGGGGGAACAACAACTGACCGTT |
| SEQ ID NO: 29:<br>nucleotide sequence<br>of monoclonal<br>antibody MR82 heavy<br>chain | CAGGTGCAACTTGTCCAGTCCGGAGCTGAAGTT<br>AAGAAGCCTGGTGCCAGCGTCAAGGTGAGTTGC<br>AAAGCATCCGGACATACATTTACAACATACGCCA<br>TACATTGGGTTCGCCAAGCACCTGGACAAGGTC<br>TTGAGTGGATGGGATGGATAAACCCAGATAATGA<br>CAACACTGAATACTCCCAAAAATTTCAGGGAAGG<br>GTAACCATAACACGGGACACATCAGCCTCTACTG<br>CCTACATGGAGCTGTCAAGTCTGATCTCTGAAGA<br>TACAGCAGTATTTTACTGTGCAAGTGCATCCTAT<br>ACCTTTTGGTCCGGATATTATAGTGGGCTCGATT<br>ATTGGGGACAGGGGACTCTGGTAACCGTAAGCT<br>CC |
| SEQ ID NO: 30:<br>nucleotide sequence<br>of monoclonal<br>antibody MR82 light<br>chain | GAGATAGTATTGACTCAGTCTCCCGGTACATTGT<br>CTCTCTCCCCAGGAGAAAGAGCTACACTCTCATG<br>TCGAGCCTCTCAAAGCGTCTCCATCAATTATCTG<br>GCCTGGTATCAACAGAAGCCTGGTCAAGCACCT<br>AGGCTCCTTATCTACGGAGCAAGCTCACGGGCT<br>ACTGGTATTCCCGATAGGTTCTCTGGCTCAGGTT<br>CCGGCACCGATTTCACTCTCACAATTAGCCGATT<br>GGAACCAGAAGATTTCGCCGTCTATTATTGTCAA<br>CAATATGGTAGCTCTCCACCCTGGACATTCGGAC<br>CTGGGACCAAGGTGGACATAAAA |
| SEQ ID NO: 31:<br>nucleotide sequence<br>of monoclonal<br>antibody MR78 heavy<br>chain | CAGCTCCAGCTGCAAGAATCTGGTCCCGGTCTT<br>GTTAAACCTAGTGAAACACTTAGCCTGACTTGCA<br>CTGTCTCAGGCGGGTCAATATCATCTTCCAGTTA<br>TTACTGGGGCTGGATCAGGCAACCCCCTGGGAA<br>AGGTCTCGAATGGATTGGCTCTGTTTATTATAGC<br>GGAGGTGCCAGTTACAATCCTAGTCTCAAGTCAC<br>GAGCCACTATTAGCGTTGATACCAGCAAAAACCA<br>ATTCAGTTTGAATCTGGATTCAGTAAGCGCAGCC<br>GACACAGCCATTTATTACTGTGCTTCCATTTATG<br>GAAGTGGGACTTTCTATTATTACTTTTACATGGAC<br>GTGTGGGGAAGGGTTCAACAGTTACTGTAAGC<br>TCC |
| SEQ ID NO: 32:<br>nucleotide sequence<br>of monoclonal<br>antibody MR78 light<br>chain | GACATTCAGATGACTCAATCTCCCAGTTCCCTGT<br>CAGCTAGTGTTGGGGACCGGGTAACCATCACCT<br>GTCAAGCAAGCCAGGTCATCAGTAACTACCTTAA<br>TTGGTATCAGCAGAAACCTGGCAAGGCCCCAAA<br>GCTGCTTATATATGATACAAGTAACCTCAAGACA<br>GGGGTTCCTAGTCGGTTCTCTGGTAGCGGTAGC<br>GGAACCGATTTCACCTTTACAATAAGTAGTCTGC<br>AACCAGAGGATATAGCCACATACTATTGTCAACA<br>GTACGAAAATCTTCAATTCACTTTCGGGCCTGGC<br>ACCAAAGTAGATATCAAA |
| SEQ ID NO: 33:<br>nucleotide sequence<br>of monoclonal<br>antibody MR191<br>heavy chain | CAACTCCAACTGCAAGAGAGCGGACCAGGGCTC<br>GTAAAACCATCAGAAACACTGTCACTCTCCTGTA<br>CCGTATCAGGTGTAAGCATCTCCGATAATTCTTA<br>TTACTGGGGTTGGATAAGACAGCCACCTGGGAA<br>GGGTTTGGAGTGGATTGGACCATCTCATACTCA<br>GGCAATACCTATTACAATCCTTCTCTTAAATCTAG |

TABLE 1-continued

| | Sequences |
|---|---|
| | GGTCAGTATATCTGGAGATACTTCCAAACACCAA<br>CTTAGCTTGAAAGTTTCATCAGTTACAGCCGCTG<br>ACACCGCAGTGTATTACTGTGCTCGCCAGCGGA<br>TCGTAAGTGGGTTTGTAGAGTGGCTTAGCAAATT<br>TGACTATTGGGGCCAGGGGACCCTTGTAACCGT<br>ATCTAGT |
| SEQ ID NO: 34:<br>nucleotide sequence<br>of monoclonal<br>antibody MR191 light<br>chain | CAGTCAGTTTTGACTCAGCCCCCCTCAGTGAGTG<br>GCGCTCCAGGTCAACGAGTCACCATCAGTTGCA<br>CTGGATCATCTTCTAATATAGGCGCTGGGTTTGA<br>CGTACACTGGTATCAGCAGTTGCCCGGCACTGC<br>TCCTAAATTGCTGATTTATGACAATAATAACCGAC<br>CTTCCGGGGTGCCTGATCGCTTTAGTGGTAGTAA<br>GTCAGGTACATCCGCTAGCTTGGCTATCACTGG<br>GCTTCAAGCAGAAGACGAGGCCGATTATTATTGC<br>CAATCCTACGATACCAGCTTGTCCGGCCCCGTC<br>GTATTTGGCGGCGGAACTAAACTCACCGTTCTC |
| SEQ ID NO: 35:<br>nucleotide sequence<br>of murine surfactant<br>protein B | ATGGCCAAGTCGCACCTACTGCAGTGGCTACTG<br>CTGCTTCCTACCCTCTGCTGCCCAGGTGCAGCT<br>ATCACGTCGGCCTCATCCCTGGAGTGTGCACAA<br>GGCCCTCAATTCTGGTGCCAAAGCCTGGAGCAT<br>GCAGTGCAGTGCAGAGCCCTGGGGCACTGCCT<br>GCAGGAAGTCTGGGGGCATGCAGGAGCTAATGA<br>CCTGTGCCAAGAGTGTGAGGATATTGTCCACCTC<br>CTCACAAAGATGACCAAGGAAGATGCTTTCCAGG<br>AAGCAATCCGGAAGTTCCTGGAACAAGAATGTGA<br>TATCCTTCCCTTGAAGCTGCTTGTGCCCCGGTGT<br>CGCCAAGTGCTTGATGTCTACCTGCCCCTGGTTA<br>TTGACTACTTCCAGAGCCAGATTAACCCCAAAGC<br>CATCTGCAATCATGTGGGCCTGTGCCCACGTGG<br>GCAGGCTAAGCCAGAACAGAATCCAGGGATGCC<br>GGATGCCGTTCCAAACCCTCTGCTGGACAAGCT<br>GGTCCTCCCTGTGCTGCCAGGAGCCCTCTTGGC<br>AAGGCCTGGGCCTCACACTCAGGACTTCTCTGA<br>GCAACAGCTCCCCATTCCCCTGCCCTTCTGCTG<br>GCTTTGCAGAACTCTGATCAAGCGGGTTCAAGC<br>CGTGATCCCCAAGGGTGTGCTGGCTGTGGCTGT<br>GTCCCAGGTGTGCCACGTGGTACCCCTGGTGGT<br>GGGTGGCATCTGCCAGTGCCTGGCTGAGCGCTA<br>CACAGTTCTCCTGCTAGACGCACTGCTGGGCCG<br>TGTGGTGCCCCAGCTAGTCTGTGGCCTTGTCCT<br>CCGATGTTCCACTGAGGATGCCATGGGCCCTGC<br>CCTCCCTGCTGTGGAGCCTCTGATAGAAGAATG<br>GCCACTACAGGACACTGAGTGCCATTTCTGCAA<br>GTCTGTGATCAACCAGGCCTGGAACACCAGTGA<br>ACAGGCTATGCCACAGGCAATGCACCAGGCCTG<br>CCTTCGCTTCTGGCTAGACAGGCAAAAGTGTGAA<br>CAGTTTGTGGAACAGCACATGCCCCAGCTGCTG<br>GCCCTGGTGCCTAGGAGCCAGGATGCCCACATC<br>ACCTGCCAGGCCCTTGGCGTATGTGAGGCCCCG<br>GCTAGCCCTCTGCAGTGCTTCCAAACCCCCACAC<br>CTCTGA |
| SEQ ID NO: 36:<br>nucleotide sequence<br>of myc-tagged murine<br>surfactant protein B | ATGGCCAAGAGCCATCTGCTGCAGTGGTTGCTG<br>CTGCTGCCCACCCTGTGTTGTCCTGGCGCCGCT<br>ATCACAAGCGCCAGCAGCTGGAATGTGCCCAG<br>GGCCCTCAGTTCTGGTGCCAGTCTCTGGAACAC<br>GCCGTGCAGTGTAGAGCCCTGGGCCACTGTCTG<br>CAGGAAGTGTGGGGACACGCTGGCGCCAACGA<br>CCTGTGTCAGGAATGCGAGGACATCGTGCATCT<br>GCTGACCAAGATGACCAAAGAGGACGCCTTCCA<br>GGAAGCTATCCGCAAGTTCCTGGAACAGGAATG<br>TGACATCCTGCCCCTGAAGCTGCTGGTGCCTAG<br>ATGCAGACAGGTGCTGGACGTGTACCTGCCTCT<br>CGTGATCGACTACTTCCAGAGCCAGATCAACCCT<br>AAGGCCATCTGCAACCACGTGGGCCTGTGCCCT<br>AGAGGCCAGGCTAAGCCTGAGCAGAACCCCGG<br>CATGCCTGACGCCGTGCCTAACCCTCTGCTGGA<br>CAAGCTGGTGCTGCCTGTGCTGCCAGGCGCTCT<br>GCTGGCTAGACCTGGACCTCACACCCAGGACTT<br>CAGCGAGCAGCAGCTGCCCATCCCCCTGCCTTT<br>CTGTTGGCTGTGCAGAACCCTGATCAAGAGGGT<br>GCAGGCCGTGATCCCCAAGggtgtgctggctgtggctgtgt<br>cccaggtgtgccacgtggtaccccttggtggtgggtggcatctgccagT<br>GCCTGGCCGAGAGATACACCGTGCTGCTGCTGG<br>ATGCCCTGCTGGGCAGAGTGGTGCCTCAGCTCG<br>TGTGTGGCCTGGTGCTGAGATGCTCTACCGAGG |

| | Sequences |
|---|---|
| | ACGCTATGGGCCCTGCCCTGCCTGCTGTGGAAC<br>CCCTGATCGAGGAATGGCCCCTGCAGGATACCG<br>AGTGCCACTTCTGCAAGAGCGTGATCAACCAGG<br>CTTGGAACACCTCCGAGCAGGCCATGCCCCAGG<br>CTATGCATCAGGCCTGCCTGAGATTCTGGCTGG<br>ACAGACAGAAATGCGAGCAGTTTGTGGAACAGC<br>ACATGCCACAGCTGCTGGCCCTGGTGCCAAGAT<br>CTCAGGACGCCCACATCACCTGTCAGGCTCTGG<br>GAGTGTGCGAGGCCCCTGCTAGTCCTCTGCAGT<br>GCTTCCAGACCCCCCACCTGCTCGAGGAACAAA<br>AACTCATCTCAGAAGAGGATCTGTGA |
| SEQ ID NO: 37:<br>nucleotide sequence<br>of HA- and myc-<br>tagged murine<br>surfactant protein B | ATGGCCAAGAGCCATCTGCTGCAGTGGTTGCTG<br>CTGCTGCCCACCCTGTGTTGTCCTGGCGCCGCT<br>ATCACAAGCGCCAGCAGCCTGGAATGTGCCCAG<br>GGCCCTCAGTTCTGGTGCCAGTCTCTGGAACAC<br>GCCGTGCAGTGTAGAGCCCTGGGCCACTGTCTG<br>CAGGAAGTGTGGGACACGCTGGCGCCAACGA<br>CCTGTGTCAGGAATGCGAGGACATCGTGCATCT<br>GCTGACCAAGATGACCAAAGAGGACGCCTTCCA<br>GGAAGCTATCCGCAAGTTCCTGGAACAGGAATG<br>TGACATCCTGCCCCTGAAGCTGCTGGTGCCTAG<br>ATGCAGACAGGTGCTGGACGTGTACCTGCCTCT<br>CGTGATCGACTACTTCCAGAGCCAGATCAACCCT<br>AAGGCCATCTGCAACCACGTGGGCCTGTGCCCT<br>AGAGGCCAGGCTAAGCCTGAGCAGAACCCCGG<br>CATGCCTGACGCCGTGCCTAACCCTCTGCTGGA<br>CAAGCTGGTGCTGCCTGTGCTGCCAGGCGCTCT<br>GCTGGCTAGACCTGGACCTCACACCCAGGACTT<br>CAGCGAGCAGCAGCTGCCCATCCCCCTGCCTTT<br>CTGTTGGCTGTGCAGAACCCTGATCAAGAGGGT<br>GCAGGCCGTGATCCCCAAGggtgtgctggctgtggctgtgt<br>cccaggtgtgccacgtggtacccctggtggtgggtggcatctgccagT<br>GCCTGGCCGAGAGATACACCGTGCTGCTGCTGG<br>ATGCCCTGCTGGGCAGAGTGGTGCCTCAGCTCG<br>TGTGTGGCCTGGTGCTGTACCCATACGATGTTCC<br>AGATTACGCTAGATGCTCTACCGAGGACGCTATG<br>GGCCCTGCCCTGCCTGCTGTGGAACCCCTGATC<br>GAGGAATGGCCCCTGCAGGATACCGAGTGCCAC<br>TTCTGCAAGAGCGTGATCAACCAGGCTTGGAAC<br>ACCTCCGAGCAGGCCATGCCCCAGGCTATGCAT<br>CAGGCCTGCCTGAGATTCTGGCTGGACAGACAG<br>AAATGCGAGCAGTTTGTGGAACAGCACATGCCA<br>CAGCTGCTGGCCCTGGTGCCAAGATCTCAGGAC<br>GCCCACATCACCTGTCAGGCTCTGGGAGTGTGC<br>GAGGCCCCTGCTAGTCCTCTGCAGTGCTTCCAG<br>ACCCCCCACCTGCTCGAGGAACAAAAACTCATCT<br>CAGAAGAGGATCTGTGA |
| SEQ ID NO: 38:<br>nucleotide sequence<br>of human surfactant<br>protein B | ATGCACCAAGCAGGGTACCCAGGCTGCAGAGGT<br>GCCATGGCTGAGTCACACCTGCTGCAGTGGCTG<br>CTGCTGCTGCTGCCCACGCTCTGTGGCCCAGGC<br>ACTGCTGCCTGGACCACCTCATCCTTGGCCTGT<br>GCCCAGGGCCCTGAGTTCTGGTGCCAAAGCCTG<br>GAGCAAGCATTGCAGTGCAGAGCCCTAGGGCAT<br>TGCCTACAGGAAGTCTGGGGACATGTGGGAGCC<br>GATGACCTATGCCAAGAGTGTGAGGACATCGTC<br>CACATCCTTAACAAGATGGCCAAGGAGGCCATTT<br>TCCAGGACACGATGAGGAAGTTCCTGGAGCAGG<br>AGTGCAACGTCCTCCCCTTGAAGCTGCTCATGC<br>CCCAGTGCAACCAAGTGCTTGACGACTACTTCCC<br>CCTGGTCATCGACTACTTCCAGAACCAGACTGAC<br>TCAAACGGCATCTGTATGCACCTGGGCCTGTGC<br>AAATCCCGGCAGCCAGAGCCAGAGCAGGAGCCA<br>GGGATGTCAGACCCCCTGCCCAAACCTCTGCGG<br>GACCCTCTGCCAGACCCTCTGCTGGACAAGCTC<br>GTCCTCCCTGTGCTGCCCGGGGCCCTCCAGGC<br>GAGGCCTGGGCCTCACACACAGGATCTCTCCGA<br>GCAGCAATTCCCCATTCCTCTCCCCTATTGCTGG<br>CTCTGCAGGGCTCTGATCAAGCGGATCCAAGCC<br>ATGATTCCCAAGGGTGCGCTAGCTGTGGCAGTG<br>GCCCAGGTGTGCCGCGTGGTACCTCTGGTGGC<br>GGGCGGCATCTGCCAGTGCCTGGCTGAGCGCTA<br>CTCCGTCATCCTGCTCGACACGCTGCTGGGCCG<br>CATGCTGCCCCAGCTGGTCTGCCGCCTCGTCCT<br>CCGGTGCTCCATGGATGACAGCGCTGGCCCAAG<br>GTCGCCGACAGGAGAATGGCTGCCGCGAGACTC<br>TGAGTGCCACCTCTGCATGTCCGTGACCACCCA |

TABLE 1-continued

Sequences

```
GGCCGGGAACAGCAGCGAGCAGGCCATACCAC
AGGCAATGCTCCAGGCCTGTGTTGGCTCCTGGC
TGGACAGGGAAAAGTGCAAGCAATTTGTGGAGC
AGCACACGCCCCAGCTGCTGACCCTGGTGCCCA
GGGGCTGGGATGCCCACACCACCTGCCAGGCC
CTCGGGGTGTGTGGGACCATGTCCAGCCCTCTC
CAGTGTATCCACAGCCCCGACCTTTGA
```

| | |
|---|---|
| SEQ ID NO: 39: Forward primer for site-directed mutagenesis for adding C-terminus HA epitope tag | TACCCATACGATGTTCCAGATTACGCTAGATGCT CTACCGAGGACGC |
| SEQ ID NO: 40: Reverse primer for site-directed mutagenesis for adding C-terminus HA epitope tag | AGCGTAATCTGGAACATCGTATGGGTACAGCAC CAGGCCACACACGAGC |

As used herein, "transduction" of a cell by a virus particle (e.g., an AAV particle) means entry of the particle into the cell and transfer of genetic material into the cell by the incorporation of nucleic acid into the virus particle and subsequent transfer into the cell via the virus particle.

As used herein, the term "polypeptide" encompasses both peptides and proteins, unless indicated otherwise. In one embodiment, the therapeutic agent is a polypeptide, an antigen, an antibody, or an antigen binding fragment, or a combination thereof.

The term "nucleic acid molecule" or its derivatives, as used herein, is intended to include unmodified DNA or RNA or modified DNA or RNA. For example, the nucleic acid molecules of the disclosure can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

Accordingly, the present disclosure also provides a nucleic acid molecule comprising a nucleotide sequence encoding a mutated AAV capsid protein, wherein the mutated AAV capsid protein comprises amino acid substitutions at amino acids 129, 445, and 731 of the AAV6 capsid protein sequence as set forth in SEQ ID NO:1. In one embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells.

Furthermore, the present disclosure provides a mutated AAV capsid protein comprising amino acid substitutions at amino acids 129, 445, and 731 of the AAV6 capsid protein sequence as set forth in SEQ ID NO:1. In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2.

As used herein, the term "viral particle", "vector", "viral vector", or "delivery vector", and their derivatives, refer to a particle that functions as a nucleic acid delivery vehicle, and which comprises the viral nucleic acid (i.e., the viral vector genome) packaged within the particle. Viral particles according to the present disclosure comprise a mutated AAV capsid and can package an AAV or rAAV vector genome or any other nucleic acid including viral or heterologous nucleic acids. A "heterologous nucleic acid" or "heterologous nucleotide sequence" is a sequence that is not naturally occurring in the virus. In general the heterologous nucleic acid or nucleotide sequence comprises an open reading frame that encodes a polypeptide and/or a non-translated RNA.

The term "recombinant adeno-associated viral particle" or "rAAV particle" comprises a rAAV vector genome packaged within an AAV capsid. The person skilled in the art readily recognizes that a rAAV particle comprises a capsid protein wherein the capsid protein encapsidates nucleic acids, often a promoter which drives expression of a gene of interest, i.e. a heterologous nucleic acid, between the AAV ITRs. The skilled person would readily recognize that a wild type AAV particle contains a rep and cap gene between ITRs while a rAAV particle contains any DNA sequence, optionally a promoter which drives expression of a transgene of interest. Both AAV and rAAV particles contain a capsid protein which encapsidates either the viral genome or heterologous nucleic acid, respectively. The skilled person can readily recognize when a helper virus construct or helper function is required, such as during production to generate rAAV particles.

A "recombinant adeno-associated viral vector genome" or "rAAV vector genome", as used herein, refers to one or more nucleic acid molecules comprising one or more heterologous nucleic acid segments (i.e., nucleic acid sequence not of AAV origin) that are flanked by at least one, optionally two, AAV inverted terminal repeat (ITRs) sequences. Such rAAV vector genomes can be replicated and packaged into viral particles when present in a producer cell that is expressing suitable helper functions or has been transfected or infected with a suitable helper in the form of plasmids, viruses or satellites such as virusoids, and is expressing AAV rep and cap gene products (i.e. AAV rep and capsid proteins). When a rAAV vector genome is incorporated into a larger nucleic acid molecule, for example, in a chromosome or in another vector such as a plasmid used for cloning or transfection, then the rAAV vector genome may be referred to as a "pro-vector" which can be "rescued" by replication and encapsidation in the presence of AAV packaging functions and suitable helper functions. A rAAV vector genome can be in any of a number of forms, including, but not limited to, plasmids, linear artificial chromosomes, complexed with liposomes, encapsulated within liposomes, and optionally, encapsidated in a viral particle, particularly rAAV particle. The term "inverted terminal repeat" or "ITR" sequence, as used herein, refers to relatively short sequences found at the termini of viral genomes which are in opposite orientations. An "AAV inverted terminal repeat (ITR)" sequence is a term readily recognized by the skilled person, referring to an approximately 145 nucleotide sequence present at both termini of the native single-stranded AAV genome. The outermost 125 nucleotides of the ITR can be present in either of two alternative orientations, providing heterogeneity among different AAV genomes and between the two ends of a single AAV genome. These outermost 125 nucleotides also contain several shorter regions of self-complementarity that allow intrastrand base-pairing to occur within this portion of the ITR. An ITR also includes any viral terminal repeat or synthetic sequence that forms a hairpin structure and functions to mediate the desired functions of an ITR such as replication, virus packaging, integration and/or pro-virus rescue. The ITR can be an AAV ITR or a non-AAV ITR. For example, a non-AAV ITR sequence such as those of canine parvovirus, mouse parvovirus, human parvovirus B-19, or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al.

An "AAV inverted terminal repeat" or "AAV ITR" may be from any AAV, including but not limited to serotypes 1, 2, 3, 4, 5, 6, 7, 8, 9, 10 or 11 or any other AAV. An AAV ITR need not have the native ITR sequence (e.g. a native AAV ITR sequence may be altered by insertion, deletion, truncation and/or missense mutations), so long as the ITR mediates the desired functions, e.g., replication, virus packaging, integration, and/or pro-virus rescue.

The term "helper virus" for AAV, as used herein, refers to a virus that allows AAV to be replicated and packaged by a host cell. Such helper viruses include, but not limited to, adenoviruses, herpesviruses and poxviruses such as vaccinia. The adenoviruses encompass a number of different subgroups including the commonly used type 5 of subgroup C (Ad5). In the case of herpesviruses, this family includes, but not limited to, herpes simplex viruses (HSV), Epstein-Barr viruses (EBV), cytomegaloviruses (CMV) and pseudorabies viruses (PRV). Adenoviruses and herpesviruses of human, non-human mammalian and avian origin are known in the art and are available from depositories such as the American Type Culture Collection (ATCC).

The term "helper function", as used herein, refers to an activity that is required for replication and/or packaging of an AAV but is not encoded within that AAV. Helper function can be provided by a host cell that is expressing suitable helper functions or by, for example, a helper virus. Without wishing to be bound by theory, helper functions may also stimulate transcription of some AAV promoters, including p5, and may enhance processivity of replication in cells in which helper functions are expressed.

The term "promoter," as used herein, refers to a nucleotide sequence that directs the transcription of a gene or coding sequence to which it is operably linked.

The term "operably linked", as used herein, refers to an arrangement of two or more components, wherein the components so described are in a relationship permitting them to function in a coordinated manner. For example, a transcriptional regulatory sequence or a promoter is operably linked to a coding sequence if the transcriptional regulatory sequence or promoter facilitates aspects of the transcription of the coding sequence. The skilled person can readily recognize aspects of the transcription process, which include, but not limited to, initiation, elongation, attenuation and termination. In general, an operably linked transcriptional regulatory sequence joined in cis with the coding sequence, but it is not necessarily directly adjacent to it.

A "segment" of a nucleotide sequence is a sequence of contiguous nucleotides. A segment can be at least about 5, 10, 15, 20, 25, 30, 35, 40, 45, 50, 60, 75, 85, 100, 110, 120, 130, 145, 150, 160, 175, 200, 250, 300, 350, 400, 450, 500 or more contiguous nucleotides.

Accordingly, in an embodiment, the rAAV vector genome comprises at least one heterologous nucleic acid segment flanked by AAV ITRs encoding a therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding a therapeutic agent in muscle, airway, liver, central nervous system, retina or lung cells.

The presence of the rAAV vector genome can be tracked by a marker. In another embodiment, the particle further comprises a nucleotide sequence encoding a marker, optionally luciferase.

A "therapeutic agent" can be an agent that can alleviate or reduce symptoms that result from an absence or defect in a protein in a cell, tissue or subject. In addition, a "therapeutic agent" can be an agent that otherwise confers a benefit to a subject, e.g., anti-infectious, acquired or genetic disease effects or improvement in survivability upon exposure to a causative agent of an infectious, acquired or genetic disease. For example, the "therapeutic agent" can be an agent to supplement the absence or defect in a protein in a cell due to a genetic defect of the host cell. Further, a "therapeutic agent" can be a polypeptide, a therapeutic protein, an antigen, an antibody, or an antigen binding fragment. The antibody can be a monoclonal, polyclonal, chimeric, humanized antibody, or a fragment thereof, or a combination thereof. The antigen binding fragment is a Fab, Fab', F(ab')2, scFv, dsFv, ds-scFv, dimer, minibody, diabody, or multimer thereof or bispecific antibody fragment, or a combination thereof.

In regard to the infectious, acquired or genetic disease Ebola, monoclonal antibodies-based therapies are effective at reversing the progression of lethal Ebola virus infection in mouse, guinea pig and non-human primate (NHP) models [19-27]. The humoral immune response correlates with survival and plays an important role in protection [28, 29]. Some of the first monoclonal antibodies shown to protect against Ebola virus infection were 1H3, 2G4 and 4G7, which formed the cocktail ZMab, and subsequently comprised two of the three components of ZMapp, which was used to experimentally treat health care workers during the West Africa outbreak [30-32]. Most effective monoclonal antibodies neutralize Ebola virus by binding the viral glycoprotein (GP) that studs the exterior of the virion and impede viral entry through inhibition of GP fusion and/or interaction with its receptor, Niemann-Pick C1, as is the case for 2G4 [33]. However, not all effective Ebola virus monoclonal antibodies are neutralizing. For example, monoclonal antibodies 5D2 and 7C9 bind the mucin-like domain of the Ebola viral GP, providing no neutralizing activity but conferring complete protection in mice [34], suggesting that for some monoclonal antibodies, immunoglobulin effector functions are critical for protection against Ebola virus [35, 36]. Therefore, the monoclonal antibodies can be administered or used as monotherapies, or combination cocktails as combination therapies.

Accordingly, in one embodiment, the therapeutic agent is monoclonal antibody or a fragment thereof. In another embodiment, the monoclonal antibody is a neutralizing monoclonal antibody or a fragment thereof, or a non-neutralizing monoclonal antibody or a fragment thereof. In an embodiment, the monoclonal antibody is a neutralizing antibody, such as the specific monoclonal antibody 1H3, 2G4, 4G7, 100, 114, CA45, ADI-15878, FVM02p, FVM04, BDBV223, or a fragment thereof, or a combination thereof, against Ebola virus. In another embodiment, the monoclonal antibody is a non-neutralizing antibody, such as the specific monoclonal antibody 5D2, 7C9, or a fragment thereof, or combination thereof, against Ebola virus. In another embodiment, the therapeutic agent is a specific monoclonal antibody 1H3, 2G4, 4G7, 5D2, 7C9, 100, 114, CA45, ADI-15878, FVM02p, FVM04, BDBV223, or a fragment thereof, or a combination cocktail thereof, against Ebola virus, or monoclonal antibody MR72, MR82, MR78, MR191, or a fragment thereof, or a combination thereof, against Marburg virus. In one embodiment, the therapeutic agent is a combination cocktail comprising at least two specific monoclonal antibodies or fragments thereof selected from the group consisting of 1H3, 2G4, 4G7, 5D2, 7C9, 100, 114, CA45, ADI-15878, FVM02p, FVM04, and BDBV223, against Ebola virus, or MR72, MR82, MR78, and MR191, against Marburg virus. In an embodiment, the monoclonal antibody is 100 or a fragment thereof against Ebola virus, or MR191 or a fragment thereof against Marburg virus. In an embodiment, the monoclonal antibody is 100 or a fragment thereof against Ebola virus. In an embodiment, the monoclonal antibody is MR191 or a fragment thereof against Marburg virus. In an embodiment, the infectious, acquired or genetic disease is Ebola, and the therapeutic agent comprises an antibody, optionally a monoclonal antibody or a fragment thereof, or an antigen binding fragment, or a combination thereof, against Ebola virus. In a further embodiment, the infectious disease is Ebola, and the therapeutic agent comprises the monoclonal antibody 100 or a fragment thereof against Ebola Virus. In a further embodiment, the infectious disease is Marburg virus disease, and the therapeutic agent comprises the monoclonal antibody MR191 or a fragment thereof against Ebola Virus.

In an embodiment, the therapeutic agent is an antibody encoded by heavy chain nucleotide sequence as shown in SEQ ID NO:3 and light chain nucleotide sequence as shown in SEQ ID NO:4; encoded by heavy chain nucleotide sequence as shown in SEQ ID NO:5 and light chain nucleotide sequence as shown in SEQ ID NO:6; encoded by heavy chain nucleotide sequence as shown in SEQ ID NO:7 and light chain nucleotide sequence as shown in SEQ ID NO:8; encoded by heavy chain nucleotide sequence as shown in SEQ ID NO:9 and light chain nucleotide sequence as shown in SEQ ID NO:10; encoded by heavy chain nucleotide sequence as shown in SEQ ID NO:11 and light chain nucleotide sequence as shown in SEQ ID NO:12; encoded by heavy chain nucleotide sequence as shown in SEQ ID NO:13 and light chain nucleotide sequence as shown in SEQ ID NO:14; encoded by heavy chain nucleotide sequence as shown in SEQ ID NO:15 and light chain nucleotide sequence as shown in SEQ ID NO:16; encoded by heavy chain nucleotide sequence as shown in SEQ ID NO:17 and light chain nucleotide sequence as shown in SEQ ID NO:18; encoded by heavy chain nucleotide sequence as shown in SEQ ID NO:19 and light chain nucleotide sequence as shown in SEQ ID NO:20; encoded by heavy chain nucleotide sequence as shown in SEQ ID NO:21 and light chain nucleotide sequence as shown in SEQ ID NO:22; encoded by heavy chain nucleotide sequence as shown in SEQ ID NO:23 and light chain nucleotide sequence as shown in SEQ ID NO:24; or encoded by heavy chain nucleotide sequence as shown in SEQ ID NO:25 and light chain nucleotide sequence as shown in SEQ ID NO:26, or a combination cocktail thereof, against Ebola virus, or an antibody encoded by heavy chain nucleotide sequence as shown in SEQ ID NO:27 and light chain nucleotide sequence as shown in SEQ ID NO:28; encoded by heavy chain nucleotide sequence as shown in SEQ ID NO:29 and light chain nucleotide sequence as shown in SEQ ID NO:30; encoded by heavy chain nucleotide sequence as shown in SEQ ID NO:31 and light chain nucleotide sequence as shown in SEQ ID NO:32, or encoded by heavy chain nucleotide sequence as shown in SEQ ID NO:33 and light chain nucleotide sequence as shown in SEQ ID NO:34, or a combination thereof, against Marburg virus. In a further embodiment, the therapeutic agent is an antibody encoded by heavy chain nucleotide sequence as shown in SEQ ID NO:13 and light chain nucleotide sequence as shown in SEQ ID NO:14, against Ebola virus. In a further embodiment, the therapeutic agent is an antibody encoded by heavy chain nucleotide sequence as shown in SEQ ID NO:33 and light chain nucleotide sequence as shown in SEQ ID NO:34, against Marburg virus.

Methods and Uses

The term "concurrent administration", "simultaneous administration" or "co-administration", and their derivatives, as used herein, refer to two or more rAAV particles, vector genomes or therapeutic agents for administration to a subject body, using doses and time intervals such that the rAAV particles, vector genomes or therapeutic agents of administration are present together within the subject body, or at a site of action in the subject body, over a time interval in less than de minimus quantities. The time interval may be any suitable time interval, such as an appropriate interval of minutes, hours, days, or weeks, for example. The rAAV particles, vector genomes or therapeutic agents of administration may be administered together, such as parts of a single composition, for example, or separately as two, three or four compositions. The rAAV particles, vector genomes or therapeutic agents of administration may be administered substantially simultaneously, for example, within less than or equal to about 5, 4, 3, 2 or 1 minute, of one another, or within a short time of one another, for example, within less than or equal to about 60, 45, 30, 20, 15 or 10 minutes. The rAAV particles, vector genomes, or therapeutic agents of administration so administered may be considered to have been administered at substantially the same time. The skilled person can readily recognize the appropriate doses and time intervals for administration of rAAV particles, vector genomes or therapeutic agents of administration to a subject body or at a site of action in the subject body, so that same will be present at more than de minimus levels within the subject body or at a site of action in the subject body, and/or at effective concentrations within the subject body or at a site of action in the subject body. The co-administration can be by one or more routes of administration. In an embodiment, two or more rAAV particles, vector genomes or therapeutic agents are co-administered to the subject in need thereof.

The term "pharmaceutically acceptable" in referring to diluent, buffer, carrier, or excipient, as used herein, includes any and all solvents, dispersion media, coatings, antibacterial and antifungal agents, isotonic and absorption delaying agents, that are physiologically compatible. Pharmaceutically acceptable diluent, buffer, carrier, or excipient includes sterile aqueous solutions or dispersions and sterile powders for the extemporaneous preparation of sterile injectable solutions or dispersion. The skilled person can readily recognize the use of such media and agents for pharmaceutically active substances. In one embodiment, the rAAV particle is comprised in a pharmaceutical composition that includes a pharmaceutically acceptable diluent, buffer, carrier, or excipient.

The term "infectious disease", "transmissible disease" or "communicable disease", and their derivatives, as used herein, refer to or describe a disease or disorder of resulted from an infection, for example, caused by infectious agents including viruses, viroids, prions, bacteria, nematodes such as parasitic roundworms and pinworms, arthropods such as ticks, mites, fleas, and lice, fungi such as ringworm, and other macroparasites such as tapeworms and other helminths. Examples of infectious diseases include viral diseases such as viral hemorrhagic fevers such as Ebola and Marburg virus disease, gastroenteritis, dengue fever, West Nile fever, yellow fever, influenza, respiratory syncytial virus disease, Lassa fever, rabies, smallpox, cowpox, horsepox, monkeypox, Hentavirus pulmonary syndrome, Hendra virus disease, human immunodeficiency virus disease and acquired immunodeficiency disease syndrome, Hepatitis, and Zika fever, and bacterial diseases including drug resistant bacterial diseases such as tuberculosis and methicillin-resistant *Staphylococcus aureus* infection, and drug resistant parasitic diseases such as malaria.

The term "genetic disease", "genetic disorder", or "genetic condition", and their derivatives, as used herein, refer to a disease, disorder or condition caused by an abnormality in a subject's genome. The abnormality includes but not limited to single gene inheritance, multifactorial inheritance, mitochondrial inheritance and chromosome abnormalities. The genetic disease, disorder or condition can be an autosomal dominant disorder, an autosomal recessive disorder, an X-linked dominant disorder, an X-linked recessive disorder or a Y-linked disorder. The genetic disease, disorder or condition can be congenital such that it is present from birth, or it can develop during the subject's lifespan due to the abnormality.

The term "acquired disease", "acquired disorder", or "acquired condition", and their derivatives, as used herein, refer to a disease, disorder, or condition that is not congenital or hereditary, but developing after birth and not caused by an abnormality in a subject's genome. It is known in the art that a subject can be genetically predisposed to an acquired disease.

The term "treating" and its derivatives, as used herein, refers to improving the condition associated with an infectious, acquired or genetic disease, such as reducing or alleviating symptoms associated with the condition or improving the prognosis or survival of the subject. The term "preventing" and its derivatives, as used herein, refer to averting or delaying the onset of the infectious, acquired or genetic disease, such as inhibiting or avoiding the advent of the disease, or vaccinated against the disease, or the lessening of symptoms upon onset of the disease, in the subject. The term "prophylactic" shall have a corresponding meaning.

The term "subject" as used herein refers to any member of the animal kingdom, optionally a mammal, optionally a human. In an embodiment, the subject is human.

Accordingly, the present disclosure provides a method of treating or preventing an infectious, acquired or genetic disease in a subject in need thereof, involving administering at least one rAAV particle, wherein the rAAV particle comprises a mutated capsid protein encapsidating a rAAV vector genome, wherein the rAAV vector genome comprises at least one heterologous nucleic acid segment flanked by AAV ITRs encoding a therapeutic agent operably linked to a promoter capable of expressing the segment in a host cell, wherein the mutated capsid protein comprises amino acid substitutions at amino acids 129, 445, and 731 of the AAV6 capsid protein sequence as set forth in SEQ ID NO: 1, and wherein the therapeutic agent treats or prevents the infectious, acquired or genetic disease in the subject in need thereof. In one embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells. In an embodiment, the therapeutic agent is any therapeutic agent as described herein, and the infectious, acquired or genetic disease is any infectious, acquired or genetic disease as described herein.

Also provided is use of at least one rAAV particle for treating or preventing an infectious, acquired or genetic disease in a subject in need thereof, wherein the rAAV particle comprises a mutated capsid protein encapsidating a rAAV vector genome, wherein the rAAV vector genome comprises at least one heterologous nucleic acid segment flanked by AAV ITRs encoding a therapeutic agent operably linked to a promoter capable of expressing the segment in a host cell, and wherein the mutated capsid protein comprises amino acid substitutions at amino acids 129, 445, and 731 of the AAV6 capsid protein sequence as set forth in SEQ ID NO: 1. In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells. In an embodiment, the therapeutic agent is any therapeutic agent as described herein, and the infectious, acquired or genetic disease is any infectious, acquired or genetic disease as described herein.

Further provided is use of at least one rAAV particle in the manufacture of a medicament for treating or preventing an infectious, acquired or genetic disease in a subject in need thereof, wherein the rAAV particle comprises a mutated capsid protein encapsidating a rAAV vector genome, wherein the rAAV vector genome comprises at least one heterologous nucleic acid segment flanked by AAV ITRs encoding a therapeutic agent operably linked to a promoter capable of expressing the segment in a host cell, and wherein the mutated capsid protein comprises amino acid substitutions at amino acids 129, 445, and 731 of the AAV6 capsid protein sequence as set forth in SEQ ID NO:1. In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells. In an embodiment, the therapeutic agent is any therapeutic agent as described herein, and the infectious, acquired or genetic disease is any infectious, acquired or genetic disease as described herein.

Even further provided is at least one rAAV particle for use in treating or preventing an infectious, acquired or genetic disease in a subject in need thereof, wherein the rAAV particle comprises a mutated capsid protein encapsidating a rAAV vector genome, wherein the rAAV vector genome comprises at least one heterologous nucleic acid segment flanked by AAV ITRs encoding a therapeutic agent operably linked to a promoter capable of expressing the segment in a host cell, and wherein the mutated capsid protein comprises amino acid substitutions at amino acids 129, 445, and 731 of the AAV6 capsid protein sequence as set forth in SEQ ID NO:1. In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In another embodiment, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells. In an embodiment, the therapeutic agent is any therapeutic agent as described herein, and the infectious, acquired or genetic disease is any infectious, acquired or genetic disease as described herein.

The rAAV particle functions as a delivery vehicle that delivers heterologous nucleic acid segment ("payloads") encoding a therapeutic agent for treating or preventing an infectious, acquired or genetic disease. In one embodiment, the infectious disease is selected from the group consisting of viral diseases such as viral hemorrhagic fevers, Ebola, Marburg virus disease, gastroenteritis, dengue fever, West Nile fever, yellow fever, influenza, respiratory syncytial virus disease, Lassa fever, rabies, smallpox, cowpox, horsepox, monkeypox, Hentavirus pulmonary syndrome, Hendra virus disease, human immunodeficiency virus disease and acquired immunodeficiency disease syndrome, Hepatitis, Zika fever, optionally Ebola or Marburg virus disease, and bacterial diseases including drug resistant bacterial diseases such as tuberculosis and methicillin-resistant *Staphylococcus aureus* infection, and drug resistant parasitic diseases such as malaria. In another embodiment, the acquired or genetic disease is selected from the group consisting of cancer, autoimmune disorders, vascular degeneration, neurodegenerative diseases such as Huntington's disease, cystic fibrosis, inflammatory bowel diseases such as Crohn's Disease, and surfactant protein B deficiency. In a further embodiment, the genetic disease is surfactant protein B deficiency.

The rAAV particle disclosed herein shows tropism to lung tissue and muscle tissue. Accordingly, also provided is use of at least one rAAV particle for delivering a therapeutic agent to a tissue for treating or preventing an infectious, acquired or genetic disease in a subject in need thereof, wherein the tissue is lung tissue or muscle tissue. In an embodiment, the use of at least one rAAV particle for delivering a therapeutic agent to a tissue in a subject in need thereof comprises use of the rAAV particle comprising a mutated capsid protein encapsidating a rAAV vector genome, wherein the rAAV vector genome comprises at least one heterologous nucleic acid segment flanked by AAV ITRs encoding a therapeutic agent, wherein the mutated capsid protein comprises amino acid substitutions at amino acids 129, 445, and 731 of the AAV6 capsid protein sequence as set forth in SEQ ID NO:1, wherein the therapeutic agent treats or prevents the infectious, acquired or genetic disease in the subject in need thereof, and wherein the tissue is lung tissue. In an embodiment, the lung tissue comprises alveolar type 2 (AT2) cells. In an embodiment, the rAAV particle described herein delivers a therapeutic agent to AT2 cells. In an embodiment, the use of at least one rAAV particle for delivering a therapeutic agent to a tissue for treating or preventing an infectious, acquired or genetic disease in a subject in need thereof comprises use of the rAAV particle comprising a mutated capsid protein encapsidating a rAAV vector genome, wherein the rAAV vector genome comprises at least one heterologous nucleic acid segment flanked by AAV ITRs encoding a therapeutic agent, wherein the mutated capsid protein comprises amino acid substitutions at amino acids 129, 445, and 731 of the AAV6 capsid protein sequence as set forth in SEQ ID NO:1, wherein the therapeutic agent treats or prevents the infectious, acquired or genetic disease in the subject in need thereof, and wherein the tissue is muscle tissue. In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2. In an embodiment, the subject is any subject as described herein. In an embodiment, the use or administration route is any use or administration route as described herein. In an embodiment, the therapeutic agent remains in the serum of the subject for any period of time as described herein. In an embodiment, the therapeutic agent is any therapeutic agent as described herein, and the infectious, acquired or genetic disease is any infectious, acquired or genetic disease as described herein. In an embodiment, the infectious disease is influenza. In an embodiment, the infectious disease is respiratory syncytial virus disease.

The present disclosure also describes a use or administration of a rAAV particle for providing or producing a constant supply or continuous infusion of therapeutic proteins or antibodies suitable in gene therapy for treating or preventing diseases. In an embodiment, the rAAV particle described herein can function as a delivery vehicle that delivers a "payload" encoding a therapeutic agent, such as a therapeutic protein or an antibody, for treating or preventing an infectious, acquired or genetic disease described herein. It is known in the art that therapeutic proteins such as monoclonal antibodies are useful in the treatment of cancer and autoimmune disorders. A number of monoclonal antibodies have been described for the treatment of cancer, for example, as reviewed in Neves and Kwok 2015 [14b], herein incorporated by reference. The use or administration of rAAV particle carrying a payload encoding therapeutic agents such as monoclonal antibodies or fragments thereof can therefore maintain an effective supply of the therapeutic agents for treating cancer in a subject in need. The use or administration of rAAV particle can also provide the accumulation of therapeutic agents at a tumor site, for example, the accumulation of a monoclonal antibody or a fragment thereof that is specific against a marker or a target expressed on tumor cells.

For genetic diseases, a constant supply of a therapeutic protein provided by the rAAV particle of the present disclosure allows for a flexible treatment approach by compensating the deficiency of an essential protein, for example, deficiency due to genetic defect or ineffective genes, for example, in lung tissue. In surfactant protein B (SPB) deficiency, patients are deficient for essential protein SPB. In an embodiment, the genetic defect or disease is surfactant protein B (SPB) deficiency. In an embodiment, the therapeutic protein is SPB. In an embodiment, the rAAV particle comprises the therapeutic protein SPB. In an embodiment, the genetic defect or disease is SPB deficiency, and the therapeutic protein is SPB. In an embodiment, the genetic defect or disease is SPB deficiency in the lung, and the therapeutic protein is SPB. In an embodiment, the rAAV particle comprises a mutated capsid protein encapsidating a rAAV vector genome, wherein the rAAV vector genome comprises nucleotide sequence encoding SPB. In an embodiment, the SPB is encoded by nucleotide sequence selected from the group consisting of SEQ ID NO:35-38. In an embodiment, the SPB is encoded by nucleotide sequence as shown in SEQ ID NO:35. In an embodiment, the SPB is encoded by nucleotide sequence as shown in SEQ ID NO:36. In an embodiment, the SPB is encoded by nucleotide sequence as shown in SEQ ID NO:37. In an embodiment, the SPB is encoded by nucleotide sequence as shown in SEQ ID NO:38.

The use or administration of a rAAV particle to a subject comprising ingestion, instillation such as intranasally, inhalation such as via aerosol, or injection. The route of injection includes but not limited to intradermal, subcutaneous, intramuscular, intravenous, intraosseous, intraperitoneal, intrathecal, epidural, intracardiac, intraarticular, intracavernous, intravitreal, intracerebral, intracerebroventricular, intratracheal or intraportal. In an embodiment, the at least one rAAV particle is administered or co-administered intravenously, intranasally, intratracheal, intramuscularly, or via aerosol. In another embodiment, two or more rAAV particles are co-administered intravenously, intranasally, intratracheally, intramuscularly, or via aerosol, to the subject in need thereof, and wherein the co-administration is by one or more routes. In an embodiment, the at least one rAAV particle is delivered to lung cells or tissues.

The therapeutic agent remains in the serum of the subject for a period of time, allowing it to protect the subject from an infectious, acquired or genetic disease, such as Ebola. In one embodiment, the therapeutic agent remains in the serum of the subject for at least 2, 4, 8, 10, 12, 14, 16 or 18 weeks, optionally at least 18 weeks, up to 26, 28, 30, 32, or 34 weeks, optionally up to 34 weeks. In another embodiment, the therapeutic agent remains in the serum of the subject for up to 34 weeks. In another embodiment, the subject is protected from Ebola from 3, 7 or 14 days post administration to at least 3 weeks, or 1, 2, 3, 4, or 5 months, optionally at least 5 months.

The present disclosure further provides a method of producing a protein in vivo in a subject, comprising delivering or introducing into the subject a rAAV particle comprising a mutated capsid protein encapsidating a rAAV vector genome, wherein the rAAV vector genome comprises at least one heterologous nucleic acid segment flanked by AAV ITRs encoding the protein operably linked to a promoter capable of expressing the segment in vivo in the subject, and wherein the mutated capsid protein comprises amino acid substitutions at amino acids 129, 445, and 731 of the AAV6 capsid protein sequence as set forth in SEQ ID NO:1. In an embodiment, the mutated capsid protein has amino acid substitutions Phe129Leu, Tyr445Phe and Tyr731Phe, wherein the mutated capsid protein is mutated AAV6 capsid protein having an amino acid sequence as shown in SEQ ID NO:2, the rAAV vector genome comprises at least one heterologous nucleic acid segment flanked by AAV ITRs encoding the therapeutic agent operably linked to a promoter capable of expressing the segment in a host cell. In another embodiment, the host cell is selected from the group consisting of a human, primate, murine, feline, canine, ovine, bovine, porcine, caprine, equine, lupine, and vulpine host cell. In a further embodiment, the promoter is capable of expressing the at least one heterologous nucleic acid segment encoding the therapeutic agent in muscle, airway, liver, central nervous system, retina or lung cells. In an embodiment, the delivering or introducing into the subject a rAAV particle comprises any mode of administration described herein.

In addition, the present disclosure provides a method of producing at least one protein in vitro in a host cell, comprising introducing into the host cell at least one recombinant adeno-associated viral (rAAV) particle comprising a mutated capsid protein encapsidating a rAAV vector genome, wherein the rAAV vector genome comprises at least one heterologous nucleic acid segment flanked by AAV ITRs encoding the protein operably linked to a promoter capable of expressing the segment in the host cell, and wherein the mutated capsid protein comprises amino acid substitutions at amino acids 129, 445, and 731 of the AAV6 capsid protein sequence as set forth in SEQ ID NO:1. In an embodiment, the protein is any protein described herein. The skilled person can readily recognize the suitable production or manufacturing methods for producing proteins such as therapeutic agents using the rAAV particle as described herein.

The following non-limiting Examples are illustrative of the present disclosure:

Example 1

Triple Mutant AAV6 Capsid Generates Rapid and Potent Expression in the Muscle and Airway of Mice The present Example describes triple mutant AAV6 capsid termed AAV6.2FF which generates rapid and potent expression in the muscle and airway of mice.

Materials and Methods

Cell Culture and Plasmids

Cell lines were maintained in DMEM (HyClone) supplemented with L-glutamine (HyClone) and 7% fetal bovine serum (HyClone) at 37° C. and 5% $CO_2$. The pDGM6 plasmid contains the Rep and AAV6 Cap genes, which was modified to generate a pDGM6.2FF plasmid. The AAV genome plasmids used contained firefly luciferase (Luc) or alkaline phosphatase (AP) driven by the CASI promoter followed by an SV40 polyA signal and a WPRE.

Heparin Binding Assay

Crude transfected cell lysate from AAV6 and AAV6.2FF pseudotyped vectors were clarified and 0.22 µm filtered prior to loading onto a 5 mL HiTrap heparin HP column (GE). The column was equilibrated with DMEM prior to loading the vector and subsequently washed first with 25 mL of HBSS without $Mg^{2+}/Ca^{2+}$ (HyClone), again with 25 mL of HBSS with $Mg^{2+}/Ca^{2+}$ (HyClone) and finally eluted with 10 mL of HBSS 300 mM NaCl. The proportion of AAV in each fraction was determined by taqman qPCR [15].

AAV Transduction, Binding & Internalization Assays $1\times10^5$ cells were plated and allowed to adhere overnight in 24 well plates. AAV was added the next day at an MOI of 2000 in triplicate. 72 hours following the addition of the vector, cell lysate was harvested for quantification of luciferase expression (Promega) and Bradford analysis to determine the total protein content (Biorad). Transgene expression is reported as relative light units (RLU) per Lg of total protein.

Intravenous Immunoglobulin (IVIG) Neutralization Assay

Human IVIG (Privigen) was serially diluted in PBS and added to $1\times10^8$ vector genomes (vg) of AAV in equal volume, for a total of 25 µl, and incubated for 1 hour at 37° C. then added to HeLa cells in triplicate. After 72 hours, cell lysate was harvested for luciferase quantification according to manufacturer's instructions.

In Vivo Imaging of Luciferase Expression

All animal experiments were approved by the Institutional Animal Care Committees of the Canadian Science Centre for Human and Animal Health and the University of Guelph and Cincinnati Children's Hospital Medical Center. Albino C57BL/6 mice (Jackson Labs) received $1\times10^{11}$ vg of AAV6-Luc or AAV6.2FF-Luc in the gastrocnemius muscle in a 40 µl injection. Luciferase expression was quantified on day 1, 3, 7, 14, 21, 28, 56 and 112 post AAV delivery using a Xenogen IVIS system.

Airway AP Expression

C57BL/6 mice (Jackson Labs) were administered $1\times10^{11}$ vg of AAV6-AP or AAV6.2FF-AP by modified intranasal technique as previously described [16]. 3 weeks following AAV delivery, the lungs and nose were harvested and fixed in 2% paraformaldehyde for 2 or 16 hours, respectively. Tissues were washed 3 times in PBS and heat inactivated for 1 hour at 65° C. prior to overnight incubation in AP staining buffer (100 mM Tris pH 8.5, 100 mM NaCl, and 50 mM $MgCl_2$) with 100×X-PHOS (10 mg/mL 5-Bromo-4-chloro-3-indolyl phosphate, Sigma) and 100× nitro blue tetrazolium chloride (50 mg/mL, Invitrogen). Gross images were obtained prior to paraffin embedding and sectioning for histological staining. Transduction was quantified by analyzing the copy number of AAV vg present 100 ng of genomic DNA extracted from paraffin embedded tissue by qPCR as previously described [16]. Quantification of AP present in homogenized lung tissue was performed as previously reported [15].

Results

F129L, Y445F and Y731F Mutations do not Impede Heparin Sulfate Binding Capacity

The ability of AAV6 to bind heparin sulfate is a favorable characteristic that enables heparin chromatography purification methods, therefore it was determined if AAV6.2FF retains heparin-binding capacity. In a heparin-binding assay, 62.4% of the input AAV6 vector was found in the elution fraction compared to 72.9% for AAV6.2FF (FIG. 1A). Furthermore, less AAV6.2FF was located in the flow-through (FT) and wash (W) fractions than AAV6 (AAV6: FT-6.7%, W1-19.3%, W2-11.4%, AAV6.FF: FT-4.9%, W1-6.1%, W2-15.8%), indicating the AAV6.2FF mutations do not negatively impact heparin binding.

AAV6.2FF Mediates Enhanced Transduction In Vitro

AAV transduction of a panel of cell lines, including human and murine lung epithelial cells, resulted in consistently greater transgene expression from AAV6.2FF compared to AAV6 and AAV9 (FIG. 1B). While AAV9 is a relatively poor transducer in cell culture, AAV6 is one of the stronger serotypes for in vitro use [2], however AAV6.2FF produced between a 7- to 39-fold increase in transgene expression depending on the cell line.

AAV cell binding assays demonstrated similar binding profiles for both AAV6 and AAV6.2FF (FIG. 1C), however, internalization assays exposed variation in AAV6 and AAV6.2FF luciferase expression (FIG. 1D). With two hours contact time, there was a 3.2-fold increase in AAV6.2FF-mediated expression compared to AAV6 and this trend steadily increased with longer contact times to a 9.1-fold difference at 72 hours. These results indicate that the mechanism of improved AAV6.2FF transduction efficiency is not due to cell binding properties but rather occurs post internalization, potentially during trafficking to the nucleus.

Mutation of Surface Exposed Tyrosine Residues Reduces Intravenous Immunoglobulin (IVIG) Neutralization of AAV6.2FF Unexpectedly, the three mutations that generate the AAV6.2FF capsid conferred a 10-fold increase in resistance to pooled IVIG neutralization. 1 mg/mL of IVIG was able to neutralize 97% of AAV6, however the same concentration was only able to neutralize 20% AAV6.2FF (FIG. 2). AAV6.2FF required a minimum of 10 mg/mL to neutralize 100% of the vector.

Figure 3A:
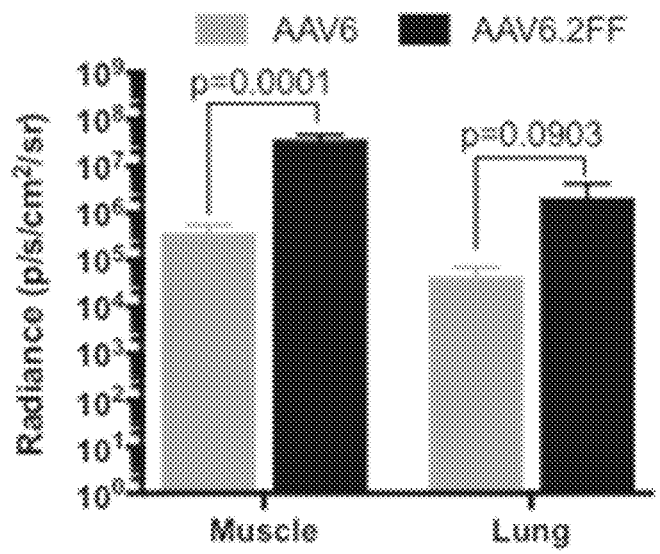
FIGS. 3A-3C show comparison of AAV6 and AAV6.2FF-mediated expression 24 hours post AAV delivery. Albino C57BL/6 mice (n=4 mice/group) received $1\times10^{11}$ vector genomes (vg) by intramuscular injection or intranasal delivery.
Figure 3B:
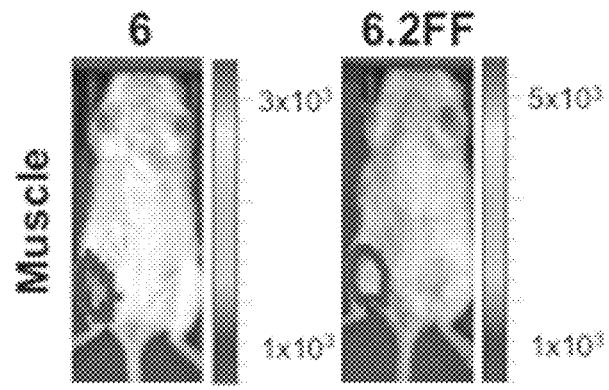
Figure 3C:
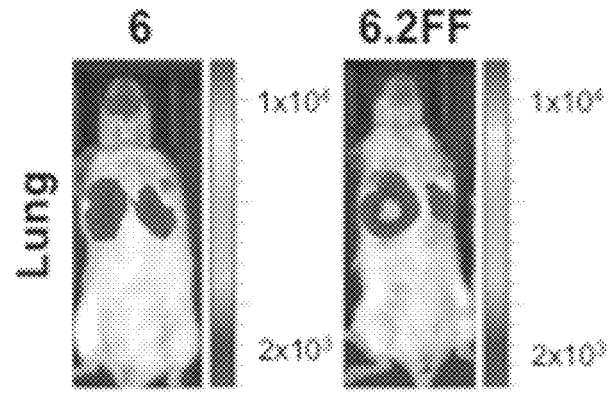

AAV6.2FF Displays Rapid Early Expression Kinetics in the Muscle and Luna of Mice Most AAV capsids reach peak transgene expression between 14-28 days post delivery, however little is known about the early expression kinetics of various capsids. AAV6 and AAV6.2FF vectors expressing firefly luciferase delivered to the muscle or the lungs were compared 24 hours following AAV administration using an in vivo imaging system (IVIS). Remarkably, in both tissues, AAV6.2FF produced drastically more transgene expression than AAV6 after only 24 hours (FIG. 3A). In the muscle, AAV6.2FF yielded 101-fold greater radiance than AAV6 (FIG. 3B), while in the lung there was a 49-fold difference favoring AAV6.2FF (FIG. 3C).

Long-Term AAV6 and AAV6.2FF-Mediated Expression in the Muscle is Equivalent

Figure 4A:
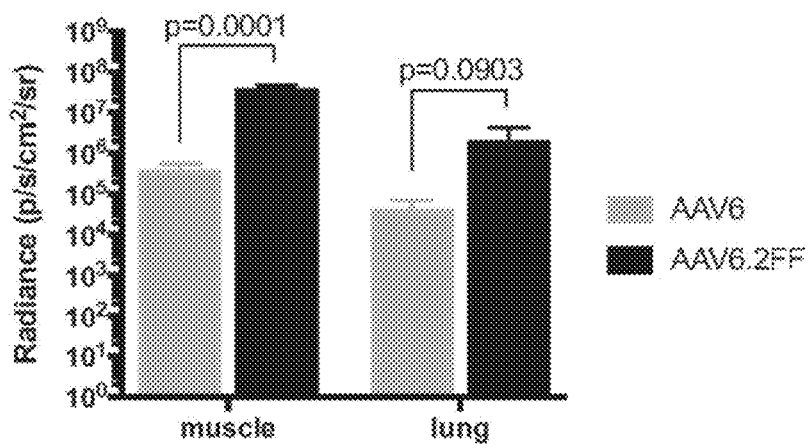
FIGS. 4A-4C show intramuscular expression kinetics of AAV6 and AAV6.2FF. Albino C57BL/6 mice (n=4/group) were injected with $1\times10^{1}$ vg of AAV6- or AAV6.2FF-Luciferase.
Figure 4B:
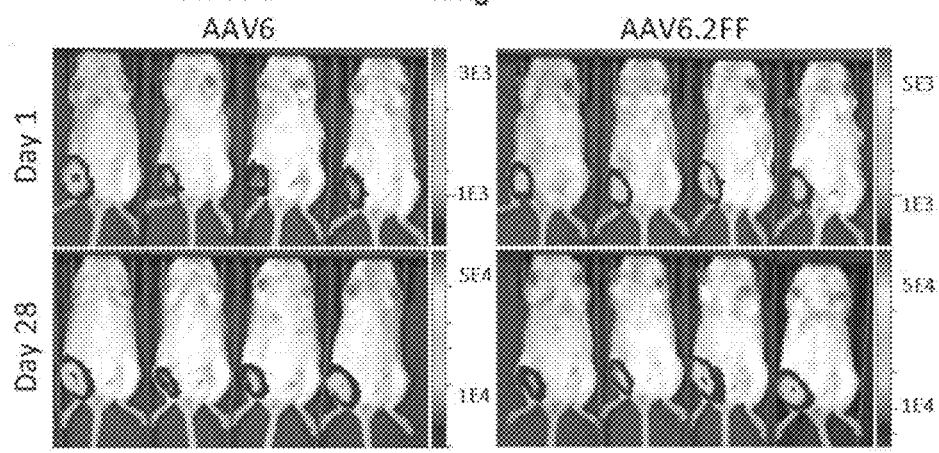
Figure 4C:
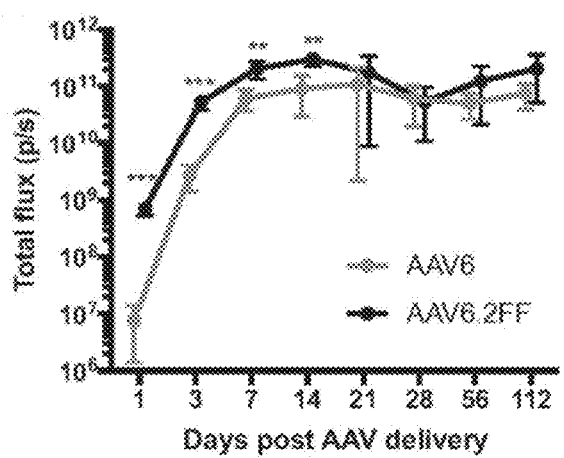

In addition to the 24-hour time point, luciferase expression was also quantified from the muscle on days 3, 7, 14, 21, 28, 56, and 112 days post AAV delivery (FIGS. 4A and 4C). AAV6.2FF-mediated transgene expression was significantly stronger than AAV6 on the days 3, 7 and 14 time points with 18.9-fold, 3.5-fold and 3.0-fold greater signal, respectively (FIG. 4B). Beyond two weeks, there is an insignificant difference in the luciferase expression produced by the AAV6 and AAV6.2FF vectors, however the luciferase signal from both groups plateaued at a high magnitude and have not begun to decline 16 weeks post injection.

AAV6.2FF is Highly Efficient at Transducing the Airway of Mice

Figures 6A, 6B, 6C:
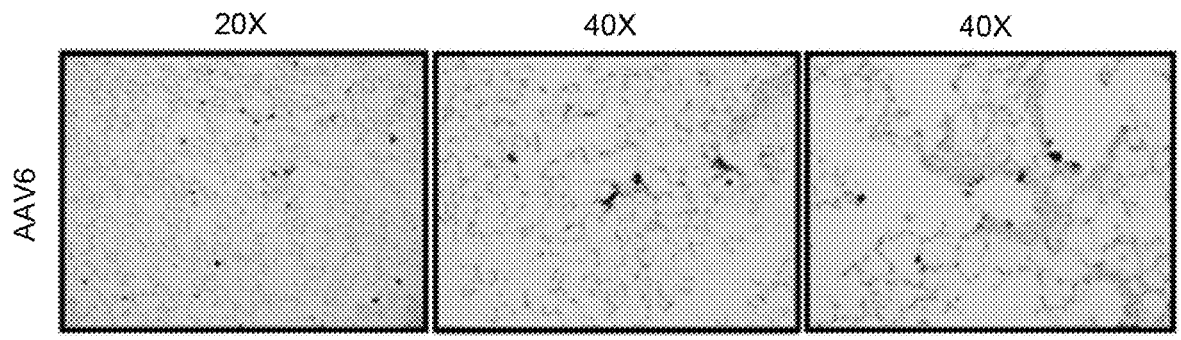
FIGS. 6A-6F show histological AP staining of lung tissue. Lung sections were counterstained with nuclear fast red and transduced cells expressing AP appear purple. Representative images of transduced lung are shown at (FIG. 6A, FIG. 6D) 20× and (FIG. 6B, FIG. 6E) 40× for AAV6 and AAV6.2FF, respectively.
Figures 6D, 6E, 6F:
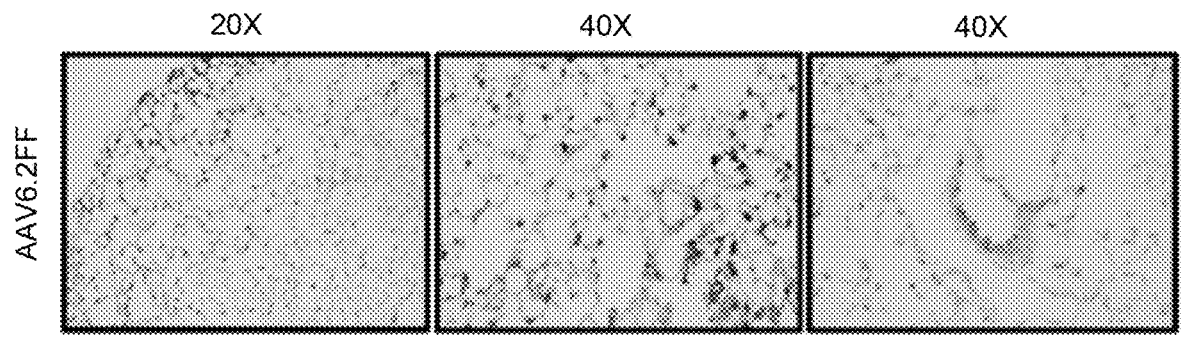

Intranasal delivery of AAV6 and AAV6.2FF vectors expressing a heat stable alkaline phosphatase (AP) demonstrated potent transduction of the mouse airway by AAV6.2FF. Although the overall AP staining distribution was consistent between the two vectors, there is a visible difference in the extent of transduction in the nasal cavity and lung lobes (FIGS. 5A-5H). Microscopic analysis of the lung tissue revealed both vectors predominantly transduce alveolar cells, however a greater proportion of cells were transduced with the AAV6.2FF vector compared to AAV6 (FIGS. 6A-6F). Both capsids also transduce airway cells in addition to alveolar cells (FIGS. 6C and 6F).

Figure 7A:
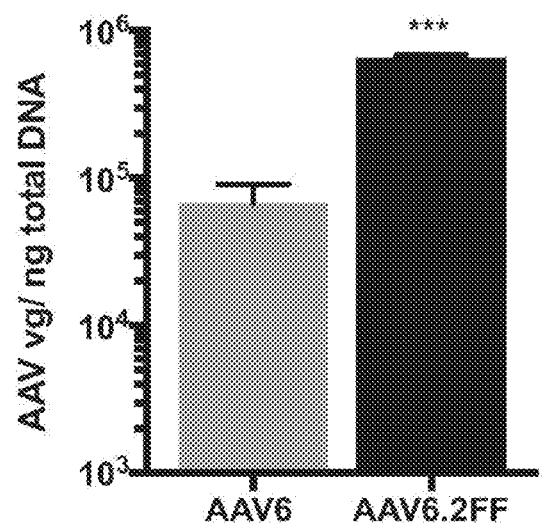
FIGS. 7A and 7B show quantification of transduced lung tissue.
Figure 7B:
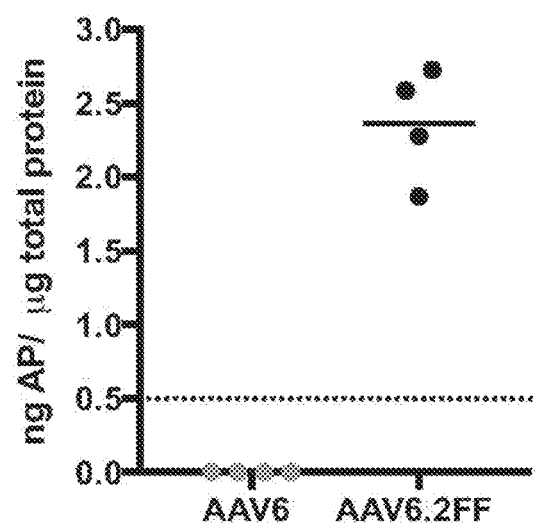

Quantification of the AAV vector genomes present in lung tissue 3 weeks following delivery demonstrates AAV6.2FF transduced the mouse lung 9.6-fold more efficiently than AAV6 (FIG. 7A). A secondary quantitative analysis of AP activity showed AAV6.2FF transduction yielded a mean of 2.36 ng of AP per µg of total lung homogenate, while the lungs transduced by AAV6 contained concentrations of AP below the level of detection (FIG. 7B).

Discussion

Similar to AAV6.2, AAV6.2FF maintains the heparin sulfate binding properties of AAV6, which is ideal for large-scale production of AAV using heparin column chromatography, as ultracentrifugation is impractical [6, 11]. AAV6 heparin binding is conferred by a single lysine at position 531 and replacing this residue with a glutamate (K531E) eliminates heparin binding capacity [12], indicating that F129L, Y445F or Y731F mutation does not hamper K531 interaction with heparin.

AAV can be difficult to work with in cell culture, sometimes requiring large multiplicities of infection (MOI) to transduce a small proportion of a monolayer. AAV6 is one of the most amenable serotypes to in vitro transduction, however, the mutations introduced to produce AAV6.2FF further improve this capsid's ability to transduce monolayer cultures. AAV6.2FF mediated the strongest luciferase expression in all cell lines tested, making it a useful tool for cell culture experiments.

Pre-existing immunity to AAV capsids has had detrimental outcomes for some past gene therapy clinical trials [13]. Two separate studies reported the presence of anti-AAV6 neutralizing antibodies in 30-46% of healthy individuals sampled [12, 13]. The increased resistance to intravenous immunoglobulin (IVIG) neutralization mediated by AAV6.2FF allows the generation of more effective gene therapies by evading pre-existing immunity while retaining other beneficial properties of AAV6. However, the decreased IVIG neutralization against AAV6.2FF is surprising in view of only three amino acid differences between AAV6.2FF and the parental AAV6. F129L is not a surface exposed residue and only becomes externally available during endosomal trafficking, without wishing to be bound by theory, therefore its role in antibody neutralization may be minimal [14]. The surface exposed tyrosine residues at positions 445 and 731 were replaced with phenylalanine and although the chemical structures of these amino acids are similar the mutations resulted in a beneficial reduction in IVIG neutralization.

AAV6.2FF mediated drastically greater transgene expression than AAV6 in the lungs and nasal cavities of mice three weeks post AAV administration. AAV6.2 was previously reported to generate approximately a 2-fold increase in transduction of alveolar cells compared to AAV6 [5], whereas AAV6.2FF enhanced transduction 9.6 times over AAV6 in the lung. Conversely, AAV6.2FF did not yield a significant difference compared to AAV6 in the muscle as long-term expression of these vectors beyond two weeks produced equivalent levels of transgene. However, 24-hour expression was much stronger from AAV6.2FF in both the muscle and lungs with 101- and 49-fold greater expression, respectively. Therefore, the present disclosure provides an engineered AAV6 variant that enhances the magnitude of early transgene expression without negatively altering the long-term expression profile of AAV6. Without wishing to be bound by theory, this increase in 24-hour expression may be due to a reduction of ubiquitin-mediated degradation of AAV capsids due to the absence of tyrosine residues at positions 445 and 731. Consequently, AAV trafficking and entry to the nucleus is more efficient, resulting in greater transgene expression shortly after viral entry [9]. This quicker transgene expression could be beneficial as a feature of AAV6.2FF-based vaccines to protect subjects during rapidly spreading infectious disease outbreaks, i.e. ring vaccination strategies.

AAV6.2FF was developed as a dual-purpose tool for a vectored immunoprophylaxis (VIP) platform to enable intramuscular and intranasal expression using the same vector to standardize vector production both for research and future translation to clinical studies. This advancement shows implications in the use of VIP as a post-exposure treatment option during outbreaks of emerging infectious diseases.

Example 2

Intramuscular AAV-Mediated Expression of Monoclonal Antibodies Provides Complete Protection Against Ebola Virus Infection Prior to 2012, Ebola virus (EBOV), a negative-sense single-stranded RNA virus in the Filoviridae family, was responsible for sporadic, well-contained outbreaks primarily localized to central Africa. The 2013-2016 West African epidemic was several magnitudes larger than any previously recorded Ebola outbreak [17]. Despite the overwhelming need for prophylactic and therapeutic options highlighted by the recent West Africa outbreak, there is still not a licensed vaccine or therapeutic available. The unusual scale of this outbreak demonstrates the potential for EBOV to cause widespread threat to human life and socioeconomic disruption (http://www.worldbank.org/en/topic/macroeconomics/publication/2014-2015-west-africa-ebola-crisis-impact-update), justifying further investigation into prevention and treatment strategies.

Monoclonal antibodies (mAbs) are a rapidly expanding set of tools for therapeutic intervention against infectious, acquired or genetic diseases that pose a significant threat to public health and for which the human population has no pre-existing or vaccine-induced immunity [18]. MAb-based therapies are effective at reversing the progression of lethal Ebola virus infection in mouse, guinea pig and non-human primate (NHP) models [19-27]. These studies demonstrate that the humoral immune response correlates with survival and plays an important role in protection [28, 29]. Some of the first mAbs shown to confer protection to EBOV were 1H3, 2G4 and 4G7, which formed the mAb cocktail ZMab, and subsequently comprised two of the three components of ZMapp, which was used to experimentally treat health care workers during the West Africa outbreak [30-32]. Most effective mAbs neutralize EBOV by binding the viral glycoprotein (GP) that studs the exterior of the virion and impede viral entry through inhibition of GP fusion and/or interaction with its receptor, Niemann-Pick C1, as is the case for 2G4 [33]. However, not all effective EBOV mAbs are neutralizing. For example, 5D2 and 7C9 bind the mucin-like domain of the EBOV GP, providing no neutralizing activity but conferring complete protection in mice [34], suggesting that for some mAbs, immunoglobulin effector functions are critical for protection against EBOV [35, 36].

Adeno-associated virus (AAV) vectors have been used extensively for gene therapy applications and are widely regarded as a safe and effective method of gene transfer [37, 38]. Functional mAbs can be produced directly in vivo through AAV-mediated expression in order to prevent viral infection [39-42]. Although this process has been coined as vectored immunoprophylaxis, suggesting utility as a "vaccine" administered prior to exposure, ideally this platform could be optimized for use in a post-exposure setting as well. A previous attempt to prevent EBOV infection by AAV9-mediated expression of mAbs yielded protection with a 14 day lead-time between intramuscular AAV administration and challenge; however, it required that one of the mAbs in the cocktail, 2G4, be humanized and that the mice be immune deficient to avoid anti-transgene B-cell responses that were thought to compromise the efficacy of the intramuscular AAV9 delivery [43]. The present disclosure shows the production of AAV vectors pseudotyped with a novel, rapidly expressing AAV capsid, AAV6.2FF, encoding murine mAbs (AAV-mAb) 2G4, 5D2 and 7C9 and evaluated the protective efficacy of these vectors as monotherapies when delivered intramuscularly. Furthermore, a two-component cocktail containing AAV-2G4 and AAV-5D2 was administered to the muscle with various lead-times prior to EBOV challenge to elucidate the minimum window required for protection.

Materials and Methods

Study Design

The overall objective of these studies was to identify a rapidly expressing AAV vector and to test the utility of AAV-mediated antibody gene transfer to protect against lethal Ebola virus challenge in mice as well as to determine the minimum therapeutic window for this application. Mouse studies involving luciferase imaging (n=4 mice/group) and Ebola virus challenge (n=6 mice/group) were conducted in the biosafety level 2 and 4 biocontainment laboratories, respectively, at the Public Health Agency of Canada, National Microbiology Laboratory (NML) and were approved by the Canadian Science Centre for Human and Animal Health Animal Care Committee. All other experiments involving mice took place at the University of Guelph Animal Isolation facility and were approved by the institutional Animal Care Committee. All mice were monitored daily and the animal care technicians were blinded to the treatment regimen.

AAV Vectors

Vector genome plasmids were engineered to contain the muscle optimized CASI promoter [39] followed by a firefly luciferase (Luc) reporter gene or a mouse IgG2a heavy chain linked to a kappa light chain by a self-cleaving 2A sequence, followed by a WPRE and a SV40 polyA signal between AAV2 inverted terminal repeats. AAV-mAb vector genomes (i.e. rAAV vector genomes) encoding the variable heavy and light chains of 2G4, 5D2, and 7C9 were codon and RNA optimized when synthesized by GeneArt. AAV genome and packaging plasmids were propagated in the SURE 2 (Agilent) strain of *Escherichia coli*. AAV vectors were produced by co-transfection of HEK 293 cells with genome and packaging plasmids as described previously [44]. Vectors pseudotyped with AAV8, AAV9 and AAV-DJ were purified by iodixanol gradient while AAV6 and AAV6.2FF vectors were purified by heparin column. AAV vector titers were determined by qPCR as described [45].

Mice

Mice were purchased from Charles River and allowed to acclimatize for 7-14 days prior to the start of an experiment. AAV vector administrations were performed on six-week-old mice. C57BL/6 mice were used in all experiments with the exception of the comparison of mAb expression in BALB/c mice. In the case of the in vivo luciferase imaging experiments, albino C57BL/6 mice were used since the lighter skin pigmentation is more conducive to imaging.

AAV Vector Administration

IM AAV administrations were performed in the gastrocnemius muscle using a 29-gauge needle and a 40 µl injection volume. IV tail vein injections were conducted on slightly heated mice using a 100 µl injection volume. Modified IN vector administrations were performed as previously described [16]. Single AAV-mAbs were administered IM or IN at a dose of $2 \times 10^{11}$ vg per mouse whereas the AAV-2G4+AAV-5D2 cocktail was dosed at a total of $4 \times 10^{11}$ vg (equal parts AAV-2G4/AAV-5D2). In the co-transduction route of administration experiments, AAV-2G4 and AAV-5D2 were co-administered either combined into one syringe for a single IM injection or as a dual instillation with each vector injected into a separate leg muscle, however the total dose was $4 \times 10^{11}$ vg regardless of administration method.

In Vivo Luciferase Imaging $1 \times 10^{11}$ vg of AAV6-Luc, AAV6.2FF-Luc, AAV8-Luc, AAV9-Luc or AAV-DJ-Luc were administered IM to 6-week old albino C57BL/6 mice in a 40 µl volume. Bioluminescence imaging was performed on days 0, 1, 3, 7, 14, 21, 28 and 56 post vector administration using the IVIS Spectrum CT instrument (Perkin Elmer, Waltham, Mass.). Briefly, mice were anesthetized by isoflurane inhalation and injected intraperitoneally with 150 mg/kg D-luciferin (potassium salt, Perkin Elmer, Waltham, Mass.) using a 25-G needle. Approximately 10 min after D-luciferin injection, mice were anesthetized under oxygen containing 1-3% isoflurane and placed into the IVIS Spectrum CT IVIS instrument imaging chamber to acquire bioluminescence surface radiance images. Resultant data were analyzed and signal intensity quantified using Living Image software (Perkin Elmer, Waltham, Mass.).

AAV-mAb Expression Profiling in Mice

Saphenous vein blood draws were conducted on a weekly basis for one month and then periodically until 126 dpa. Serum levels of EBOV-specific antibody were determined by ELISA, as previously described [46].

EBOV Challenge Studies

The mice challenge studies were performed in the biological safety level-4 (BSL-4) facility at the Canadian Science Centre for Human and Animal Health (CSCHAH) in Winnipeg, Canada. The protocol was approved by the Animal Care Committee of the CSCHAH in accordance with guidelines from the Canadian Council on Animal Care. Groups of six mice were challenged intraperitoneally with $1000 \times LD_{50}$ of MA-EBOV strain Mayinga [47]. Naive control animals received DMEM only. Clinical signs of infection and body weight were monitored daily for two weeks after challenge and survivors were followed three times longer than the death of the last control animal.

Statistical Analysis

GraphPad Prism 7 software was used for statistical analyses. Multiple t-tests were used to compare differences in luciferase expression from each AAV capsid and to compare AAV-2G4 and AAV-5D2 mAb expression levels at each time point. 2-way ANOVA was used to analyze differences in mAb output following different routes of administration of the AAV-2G4/AAV-5D2 cocktail. Challenge survival of AAV-mAb treated groups was compared to the mock group using the Mantel-Cox log rank test.

Results

AAV Vectors Mediate Early Onset Transgene Expression Following Intramuscular Injection In an effort to identify an AAV vector that promotes robust and rapid transgene expression following intramuscular (IM) injection, a panel of AAV capsids representing some of the most commonly used serotypes for muscle transduction, including AAV6, AAV8 and AAV9 were used to pseudotype an AAV-CASI-Firefly Luciferase (AAV-Luc) genome and monitored for early transgene expression kinetics. In addition to the above-mentioned capsids, a novel variant of AAV6, termed AAV6.2FF, as described above in Example 1, was engineered with three point mutations to enhance muscle transduction and AAV-DJ, which has not previously been evaluated for muscle transduction, were included in the panel. Images depicting firefly luciferase expression from each of the five vectors were captured on days 1, 3, 7, 14 (FIG. 8A), 21, 28 and 56 post AAV vector administration (FIG. 9). The flux (photons/second) generated at the site of IM injection by animals within each of the AAV vector groups was quantified over time (FIG. 8B). Luciferase transgene expression was detectable as little as 24 hours (hr) post vector-administration for all AAV capsids and continued to increase in intensity over the first 14-21 days before plateauing and remaining relatively stable for up to 56 days post-vector administration. Mice were continued to be monitored for luciferase expression on a bimonthly basis to determine when transgene expression begins to wane. At 24 hr post-vector administration, AAV6.2FF expressed luciferase at levels that were statistically significantly higher than any of the other capsids investigated, including the gold standards AAV8 and 9, with AAV6.2FF flux values that ranged from 10 to 1000 times greater than all other vectors tested. Since AAV6.2FF promoted the fastest and most robust transgene expression, particularly at early time points, and because that transgene expression remained localized to the site of injection; this capsid was selected for AAV-mediated antibody gene transfer experiments.

Substantial Extramuscular Luciferase Expression Detected Following IM Administration of AAV8 and AAV9 Vectors IM administration of AAV8 and AAV9 vectors expressing firefly luciferase was found to mediate substantial transgene expression in tissues other than the muscle (FIGS. 10A and 10B, FIGS. 11A and 11B). This inadvertent transduction was particularly striking for AAV9, where luciferase expression in extramuscular tissues, particularly in the abdomen (liver), represented 70-90% of the total flux 24 hr post-vector administration (FIG. 10D). This value was somewhat lower and more variable for AAV8, with peak extramuscular transgene expression occurring three days post-vector administration and representing 0-85% of the total flux (FIG. 10C). In both cases, extramuscular transgene expression waned such that it was no longer detectable at 21 and 56 days post-AAV8 and AAV9 administration, respectively.

Sustained AAV6.2FF-Mediated mAb Expression Levels in the Serum More than 18 Weeks after IM Vector Administration Antibody expression levels in mice transduced with AAV6.2FF pseudotyped AAV-2G4 and AAV-5D2 were monitored from 0-126 days following IM administration (FIGS. 12A and 12B). Serum 2G4 and 5D2 antibody levels rose steeply during the first 14 days and subsequently slowed, but have yet to decline at 126 days post AAV (dpa) administration. While serum containing 2G4 tended to yield somewhat higher ELISA OD values than 5D2, there was no statistically significant difference in serum EBOV GP binding capacity at any time point between the AAV-2G4 and AAV-5D2 groups. Moreover, AAV-2G4 and AAV-5D2 mAb expression levels were comparable following intranasal (IN) administration; however, this mode of vector administration resulted in lower overall serum antibody levels than IM administration (FIGS. 13A and 13B) [16]. Finally, differences in AAV-mediated antibody expression levels were detected in mice with different genetic backgrounds, such that mAb expression levels were considerably higher in BALB/c than in C57BUL6 mice regardless of route of administration, and this was statistically significant at 14 and 21 dpa for IM and IN routes of administration, respectively (FIGS. 14A and 14B). Taken together, these results indicate that IM delivery of EBOV mAbs using AAV6.2FF promotes robust and sustained serum mAb expression levels for more than four months and that AAV-mediated mAb expression differs depending on the genetic background of the mouse.

Optimizing AAV-Vector Mediated Delivery of mAb Cocktails

Since therapeutic antibodies against EBOV are often given in the form of a mAb cocktail, the feasibility of co-administering two different AAV-mAb vectors in the same dose while still producing functional antibodies was investigated. To address this question, an equal dose of the AAV-2G4/AAV-5D2 cocktail was administered in either a single intravenous (IV) tail vein injection or a single IM injection. A third group received two separate IM injections; AAV-2G4 in the left leg and AAV-5D2 in the right leg, to investigate whether heterodimer formation due to AAV co-transduction would impact production of functional mAb titers. No significant difference was found in mAb expression levels between IV, one or two IM injections at 7, 49 or 126 dpa; however, there was a trend toward slightly better serum mAb expression levels in the mice that received AAV-mAb vectors in two separate IM injections (FIG. 15).

For this reason, the AAV-mAb cocktail was administered as two IM injections for the challenge studies.

AAV-Mediated mAb Expression Provides Complete Protection Against EBOV Challenge

Figure 8A:
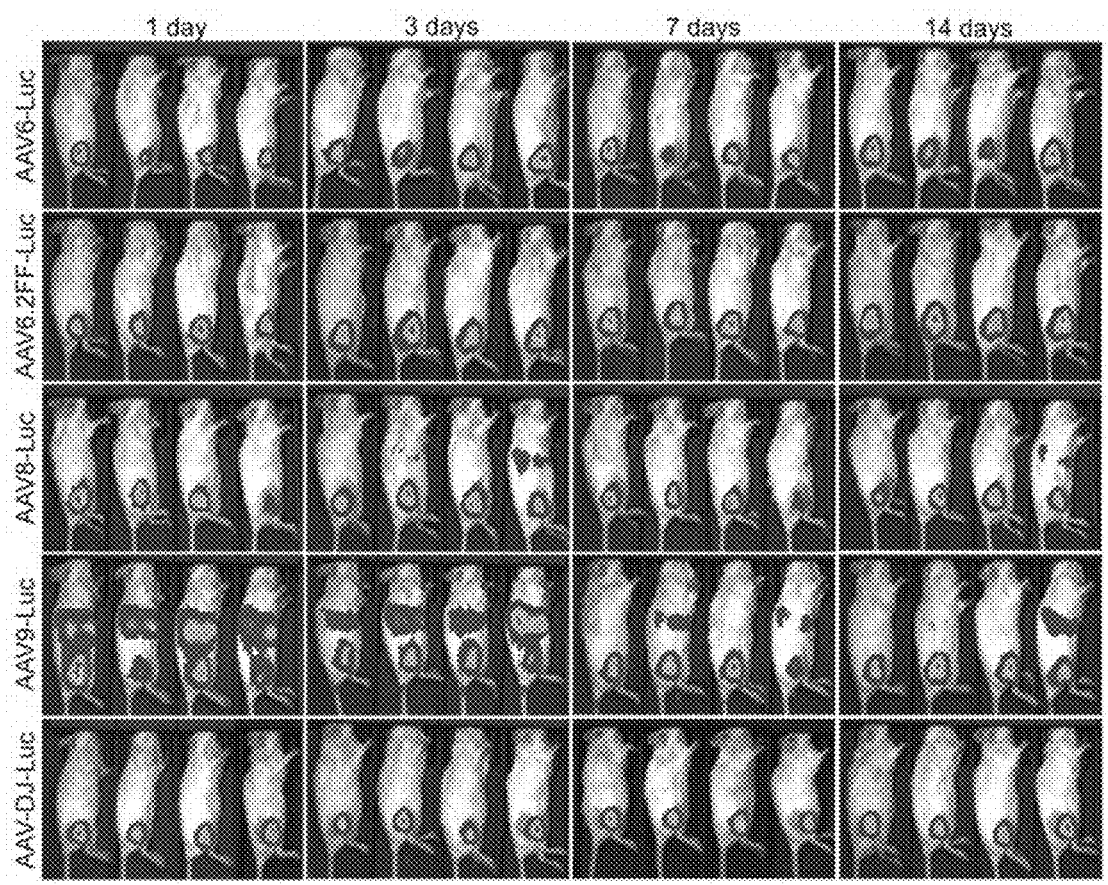
FIGS. 8A and 8B show early transgene expression kinetics of five different AAV capsids. Albino C57BU6 mice (n=4/group) were injected intramuscularly with $1\times10^{11}$ vg of an AAV vector expressing firefly luciferase (Luc) packaged with either AAV6, AAV6.2FF, AAV8, AAV9 or AAV-DJ capsid.
Figure 8B:
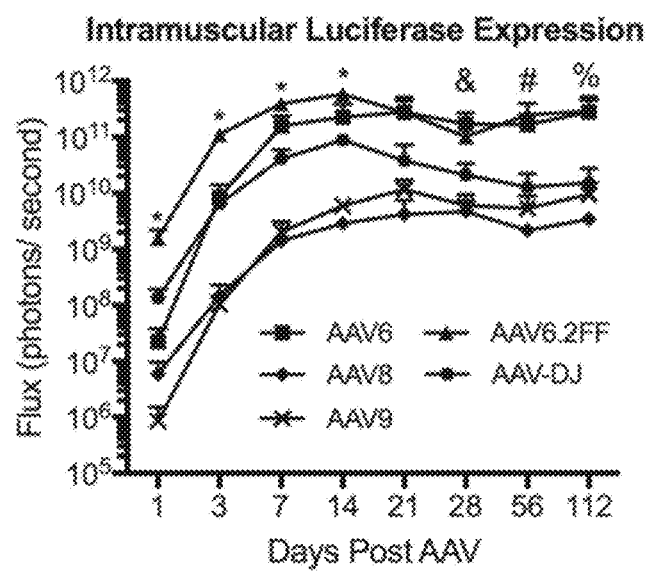
Figure 9:
FIG. 9 shows in vivo imaging of AAV-mediated luciferase expression at later time points. Additional luciferase imaging of the mice described in FIGS. 8A-8B was conducted 21, 28 and 56 days after mice received a single IM injection of $1 \times 10^{11}$ vg of AAV-Luc pseudotyped with five different AAV capsids. # Image was not obtained for this mouse.
Figure 10A:
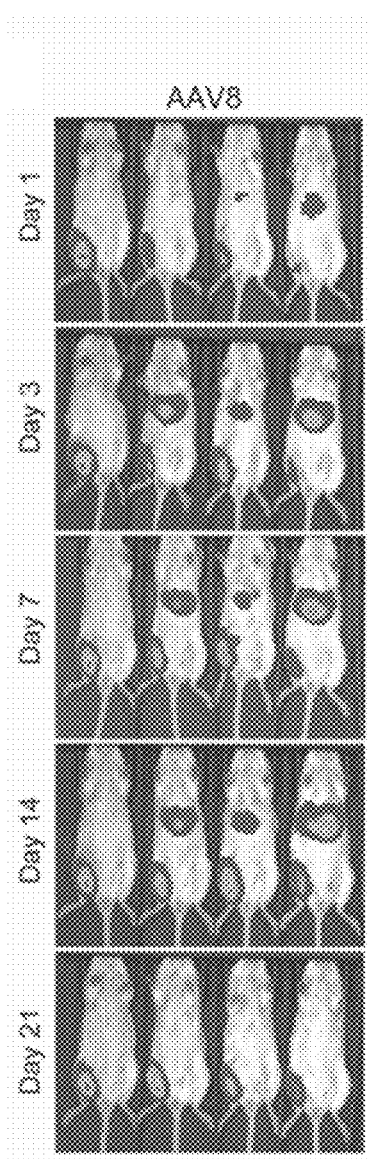
FIGS. 10A-10D show substantial extramuscular transgene expression mediated by AAV8 and AAV9 vectors following intramuscular administration. Albino C57BL/6 mice (n=4/group) injected intramuscularly with $1 \times 10^{11}$ vg of AAV8 (FIG. 10A) or AAV9 (FIG. 10B) vectors expressing firefly luciferase were imaged ventrally on days 1, 3, 7, 14, 21, 28 and 56 dpa. The relative photon emission ($p/s/cm^2/sr$) produced by luciferase from AAV8 (FIG. 10C) and AAV9 (FIG. 10D) was quantified at various time points from 1 to 56 dpa and the percent extramuscular transgene expression relative to the total transgene expression graphed. Each line depicts the luciferase expression profile of an individual animal.
Figure 10B:
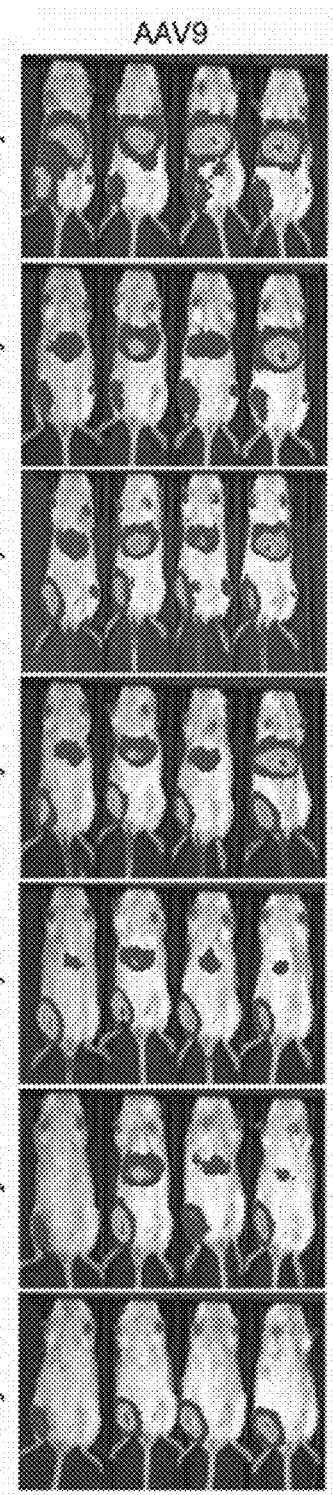
Figure 10C:
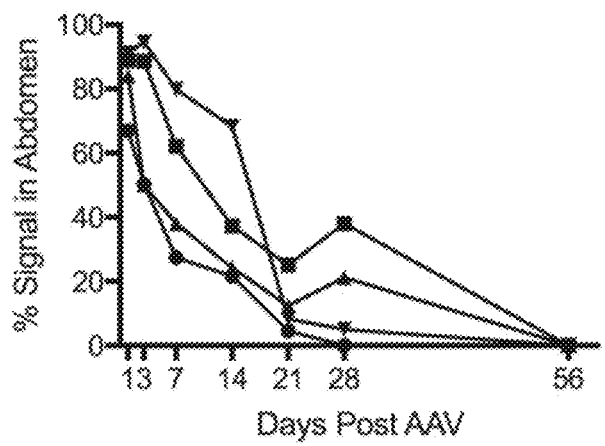
Figure 10D:
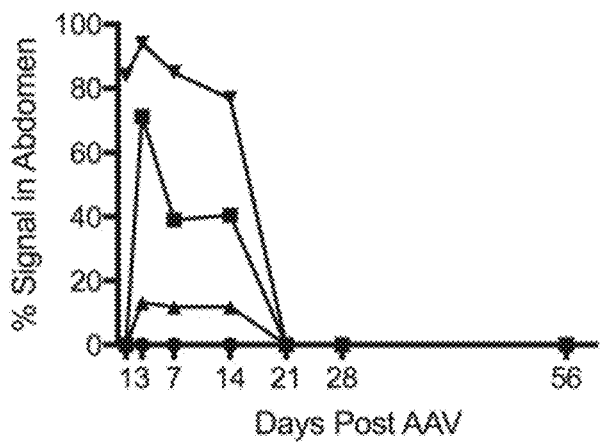
Figure 11A:
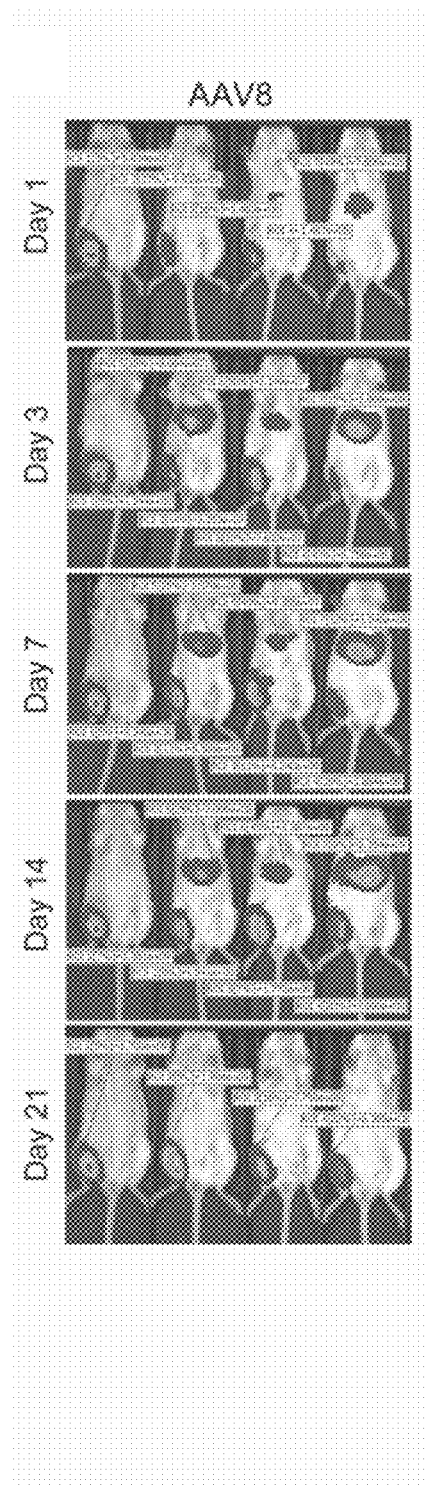
FIGS. 11A and 11B show region of interest (ROI) values for extramuscular transgene expression mediated by AAV8 and AAV9 vectors following intramuscular administration. Albino C57BL/6 mice (n=4/group) injected intramuscularly with $1 \times 10^{11}$ vg of AAV8 (FIG. 11A) or AAV9 (FIG. 11B) vectors expressing firefly luciferase were imaged ventrally on days 1, 3, 7, 14, 21, 28 and 56 dpa and ROI values for areas where signal was quantified are shown.
Figure 11B:
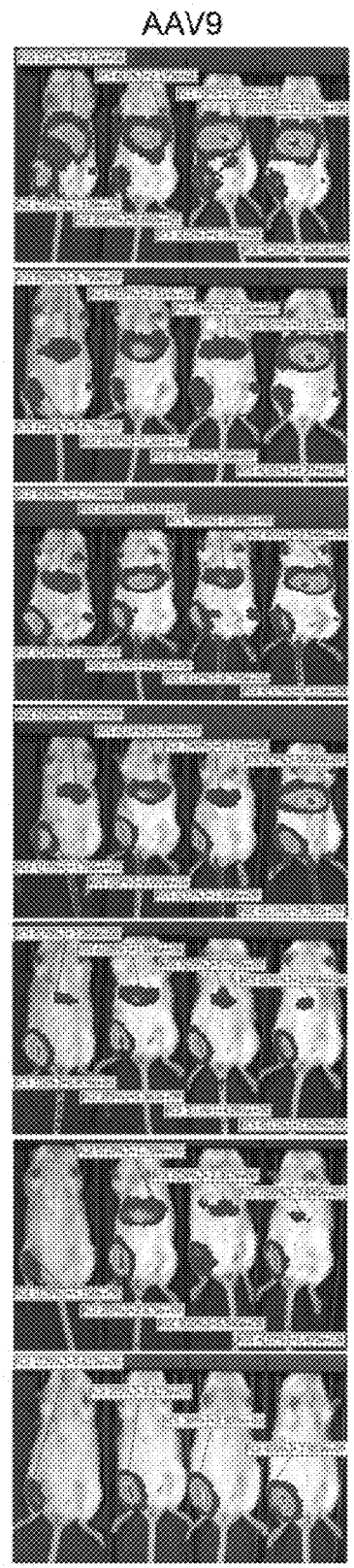
Figure 16A:
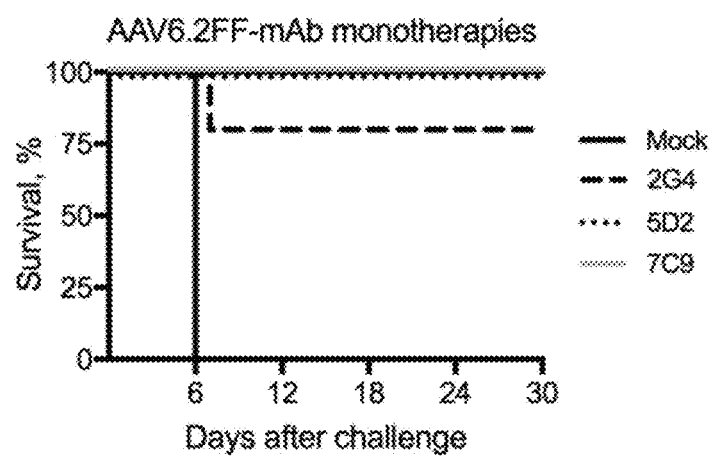
FIGS. 16A-16D show AAV6.2FF-mediated expression of 5D2 and 7C9 provides complete protection against mouse-adapted Ebola virus (MA-EBOV) challenge. C57BL/6 mice (n=6/group) received an IM injection of $2 \times 10^{11}$ vg of single AAV6.2FF-mAbs or a cocktail of $2 \times 10^{11}$ vg of AAV6.2FF-2G4 and $2 \times 10^{11}$ vg of AAV6.2FF-D2 for a total dose of $4 \times 10^{11}$ vg. All AAV monotherapies were given 14 days prior to intraperitoneal challenge with $1000 \times LD_{50}$ MA-EBOV.
Figure 16B:
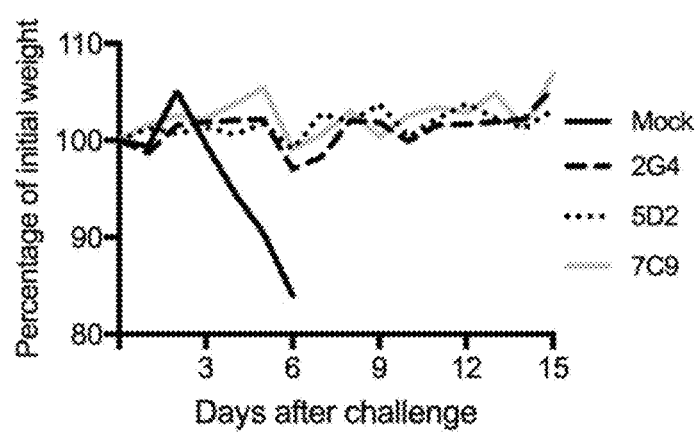

Previous studies using AAV vectors to express mAbs in a prophylactic setting allowed between 14-28 days for antibody to accumulate in the serum before animals were challenged [43, 48]. Given the speed with which transgene expression was detectable after AAV6.2FF muscle transduction (FIGS. 8A and 8B), mice were initially challenged with mouse-adapted Ebola virus (MA-EBOV) 14 days after AAV-mAb administration. For this experiment, mice receiving AAV-5D2 or AAV-7C9 (expressing non-neutralizing mAbs) were completely protected from lethal MA-EBOV challenge, whereas the group that received AAV-2G4 had 83% survival (FIG. 16A). Moreover, mice that received the AAV-mAb monotherapies experienced negligible weight loss (FIG. 16B).

Figure 16C:
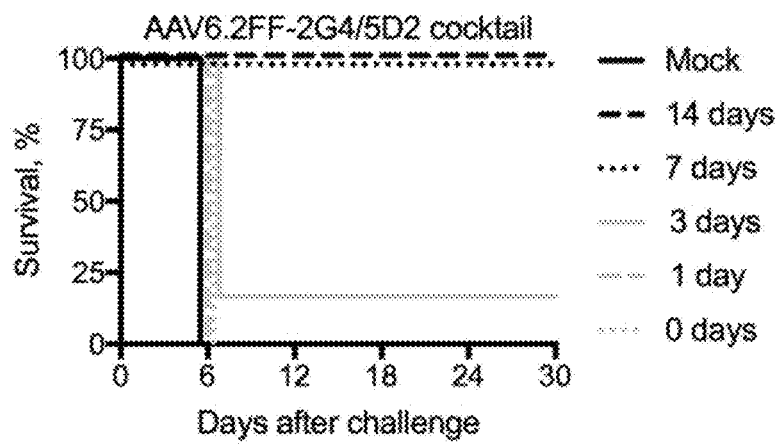
Figure 16D:
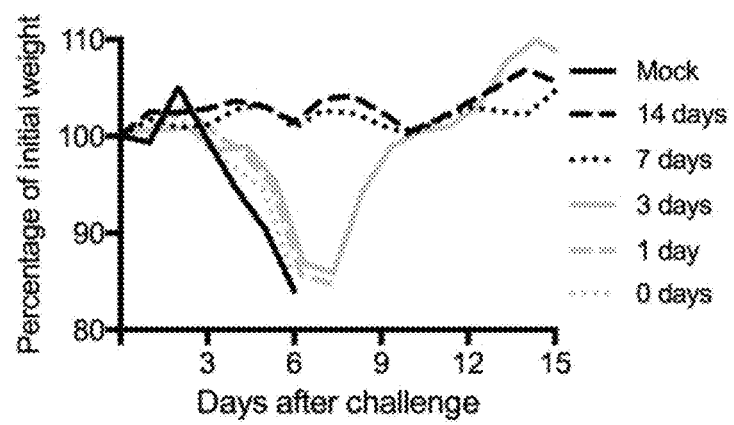

In addition to the use of AAV-mAb expression in a prophylactic setting, the application of this strategy was investigated in a post-exposure or therapeutic setting. Using a two-component mAb cocktail comprised of AAV-2G4, a neutralizing mAb, and AAV-5D2, a non-neutralizing mAb, the minimum lead-time required to confer protection against lethal MA-EBOV challenge in mice was characterized. Similar to the AAV-mAb monotherapies, the cocktail was able to provide 100% protection when administered 14 days prior to challenge (FIG. 16C). Full protection was also observed with seven days' lead-time without apparent morbidity (FIG. 16D). Remarkably, the cocktail conferred 16% survival with only three days' lead-time for mAb accumulation; however, this mouse experienced weight loss and displayed clinical signs of infection prior to recovery. No extension of life in the other mice in the three-day group was observed, and the sole mouse to succumb to infection in the AAV-2G4 monotherapy group died only one day after the control mice. MA-EBOV challenge the same day or 24 hr post AAV-mAb delivery did not extend survival and these mice died on day 6-post infection along with control mice.

Figure 12A:
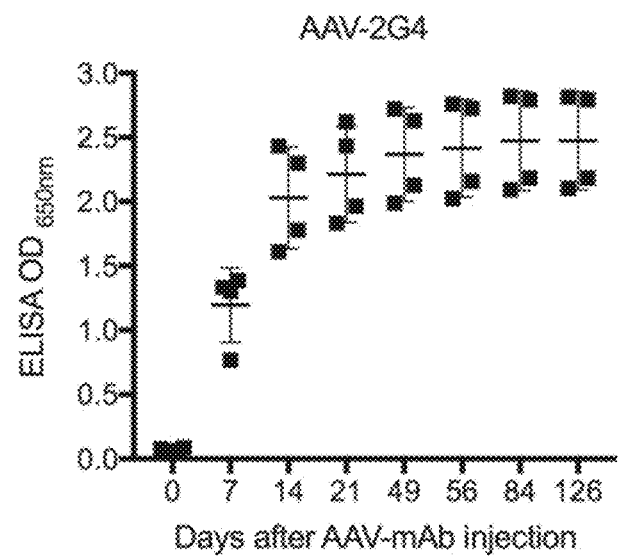
FIGS. 12A and 12B show AAV6.2FF-mAb expression levels in mice following intramuscular administration. C57BL6 mice (n=4) were injected IM with $2 \times 10^{11}$ vg of (FIG. 12A) AAV-2G4 or (FIG. 12B) AAV-5D2. Serum was collected from 1 to 126 dpa and analyzed at a 1:100 dilution for Ebola virus glycoprotein (EBOV GP) binding capacity by ELISA.
Figure 12B:
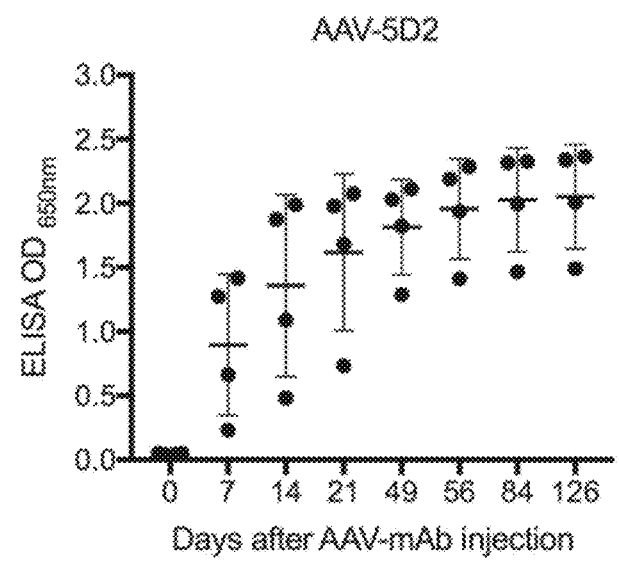
Figure 14A:
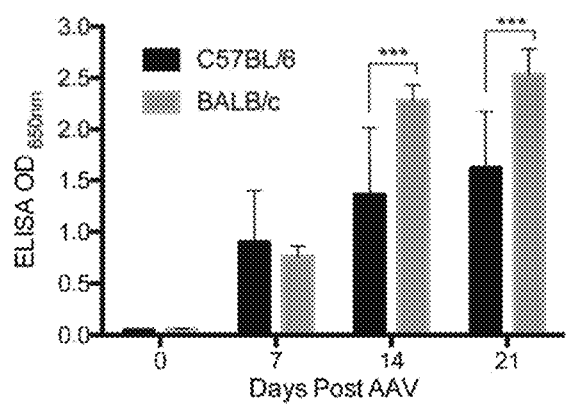
FIGS. 14A and 14B show comparison of mAb expression levels in C57BL6 and BALB/c following intramuscular and intranasal administration of AAV-5D2. Groups of C57BL/6 and BALB/c mice (n=4) were injected IM (FIG. 14A) or IN (FIG. 14B) with $2 \times 10^{11}$ vg of AAV-5D2. Serum was collected and analyzed at a dilution of 1:100 for EBOV GP binding capacity by ELISA. p=0.001. Serum mAb expression was compared using multiple t-tests, one per time point. ***Indicates $p<0.001$ and *indicates $p<0.05$.
Figure 14B:
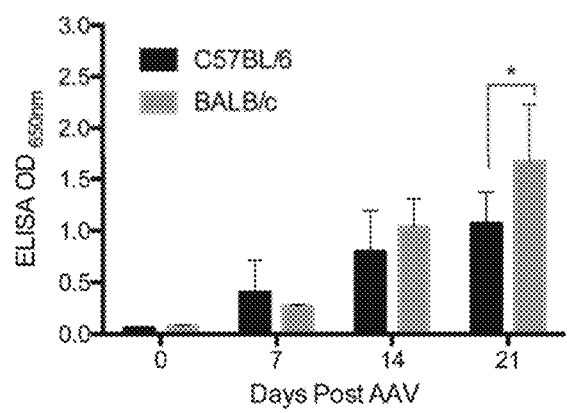
Figure 15:
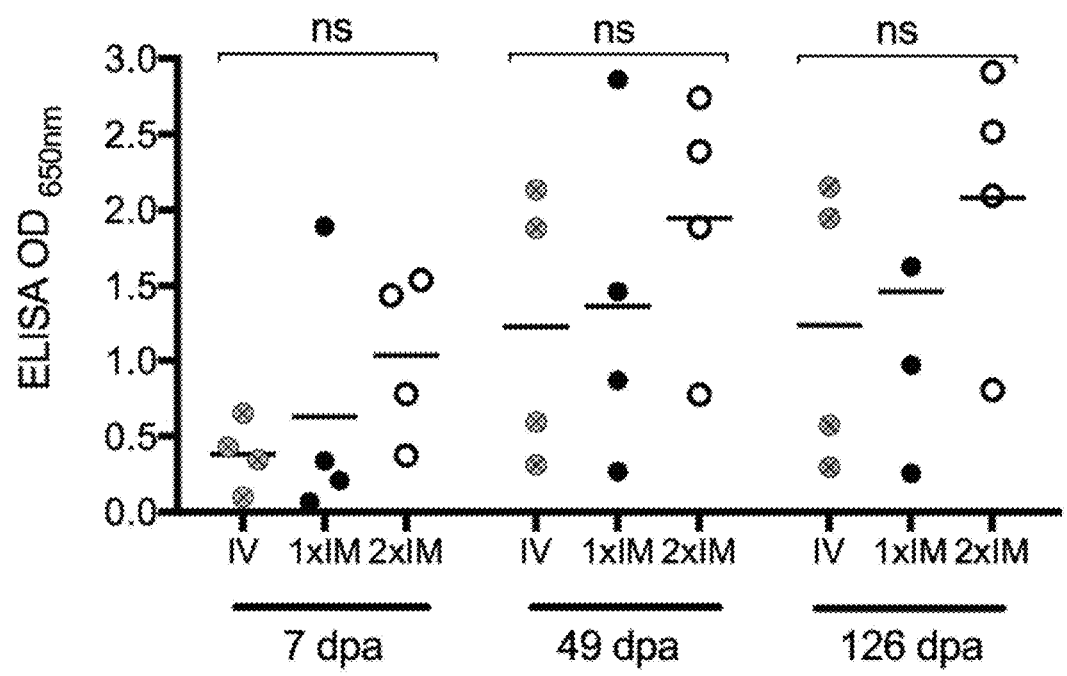
FIG. 15 shows comparison of AAV6.2FF-mediated mAb cocktail (2G4+5D2) expression levels in mice following intravenous, single, or separate intramuscular injections. Serum mAb expression levels in C57BL/6 mice (n=4) following AAV6.2FF-2G4/AAV-5D2 cocktail ($4 \times 10^1$ vg total) administration either combined and administered intramuscularly (1×IM) or intravenously (IV) or separated and administered in two IM injections (2×IM) on either leg were evaluated by ELISA. No significant differences in mAb expression levels were observed when comparing routes of administration or combined vs. separate injections of AAV vectors by 2-way ANOVA.
Figure 17A:
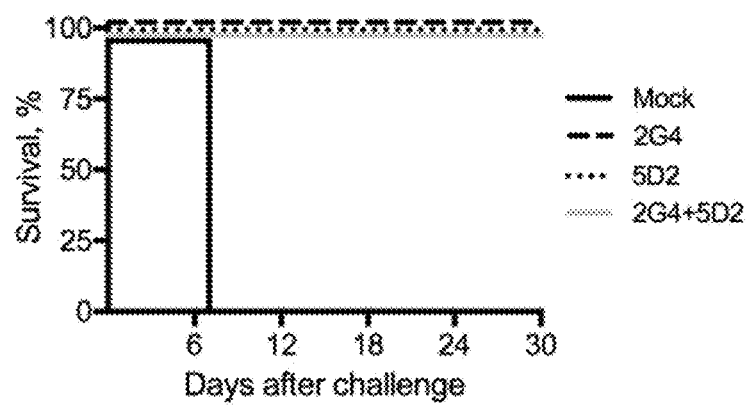
FIGS. 17A and 17B show sustained AAV6.2FF-mediated mAb expression protects mice from MA-EBOV challenge five months after a single IM injection. C57BL/6 mice received an IM injection of $2 \times 10^{11}$ vg of single AAV6.2FFmAbs (n=4/group) or a cocktail of $2 \times 10^{11}$ vg of AAV6.2FF-2G4 and $2 \times 10^{11}$ vg of AAV6.2FF-5D2 (n=8/group) for a total dose of $4 \times 10^{11}$ vg. AAV vectors were administered 140 days prior to intraperitoneal challenge with $1000 \times LD_{50}$ MA-EBOV.
Figure 17B:
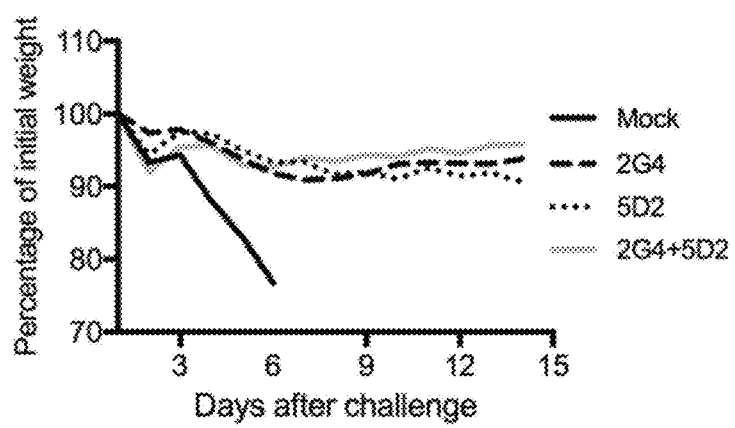

Protection from EBOV Challenge Extends Five Months after a Single IM Injection of AAV-mAb Investigated next was the protective efficacy of AAV-mediated mAb expression from a single administration given five months prior to challenge. Groups of mice received AAV-2G4, AAV-5D2 or an AAV-2G4/AAV-5D2 cocktail by IM injection (either in one injection or as two separate injections) and were subsequently monitored for serum mAb levels by ELISA (see FIGS. 12A and 12B and FIG. 15). At 126 dpa, mice were bled and their serum mAb levels evaluated by ELISA. As shown in Table 2, ELISA OD readings ranged from 0.25 to 3, with mice receiving one IM injection containing AAV-2G4+AAV-5D2 having somewhat lower serum antibody levels compared to mice receiving the cocktail as two separate IM injections. At 140 days post-AAV-mAb administration, mice were challenged intraperitoneally with $1000 \times LD_{50}$ MA-EBOV and monitored for clinical signs of disease and weight loss. Age matched control mice all died on day 7 and two of the mice from the AAV-2G4/AAV-5D2 single IM cocktail group (mouse #6 and 8, Table 2) died on days 8 and 9 post-challenge (FIGS. 17A and 17B). All other mice survived challenge despite having lower serum mAb levels than the mouse that died on day 9 (Table 2). In this second study in which older mice were challenged, the survivors lost weight for a longer period of time than six to eight-week-old mice challenged 7 to 14 days after AAV-mAb administration (FIGS. 16B and 16D). These results demonstrate that AAV VIP mediates stable, long-term mAb expression in the serum of mice and can confer protection against lethal MA-EBOV challenge more than five months after a single IM administration.

TABLE 2

Results of MA-EBOV challenge 140 days after mice received a single intramuscular injection of an AAV6.2FF vector expressing 2G4, 5D2 or a combination of 2G4 + 5D2.

| AAV Vector | Mouse # | ELISA OD reading prior to challenge# | Outcome |
| --- | --- | --- | --- |
| AAV-2G4 | 1 | 2.8 | Survived |
|  | 2 | 2.2 | Survived |
|  | 3 | 2.1 | Survived |
|  | 4 | 2.8 | Survived |
| AAV-5D2 | 1 | 1.5 | Survived |
|  | 2 | 2 | Survived |
|  | 3 | 2.4 | Survived |
|  | 4 | 2.3 | Survived |
| AAV-2G4 + AAV-5D2 | 1 | 2.1 | Survived |
|  | 2 | 2.5 | Survived |
|  | 3 | 2.9 | Survived |
|  | 4 | 0.8 | Survived |
|  | 5* | 1 | Survived |
|  | 6* | 3 | Died |
|  | 7* | 1.6 | Survived |
|  | 8* | 2.5 | Died |

Serum was harvested from mice 14 days prior to intraperitoneal challenge with $1000 \times LD_{50}$ of MA-EBOV. *Mice received AAV-2G4+AAV-5D2 as a single IM injection.

Discussion

Vectored immunoprophylaxis (VIP), in which AAV vectors are used to deliver pathogen specific mAb genes in vivo allowing for continuous and sustained secretion of antibodies into the circulation, offers a novel approach for pre- and post-exposure prophylaxis against pathogens of public health importance for which no effective vaccines or therapies are available. VIP has been shown to be highly effective at protecting mice, ferrets, and non-human primates (NHPs), from a variety of infectious agents including human immunodeficiency virus [39, 40], influenza virus [41, 42] and *Plasmodium falciparum* sporozoites [49]. Recently, AAV9-mediated delivery of two of the antibody components of the ZMapp cocktail protected mice against systemic and airway challenge with MA-EBOV when delivered 14 days prior to challenge [43]. The aim of this study was to investigate whether AAV-mediated antibody gene transfer of a single neutralizing or non-neutralizing antibody could protect mice from systemic EBOV challenge, and to determine the minimum therapeutic window between AAV-mediated antibody-transfer and challenge.

To investigate the potential utility of VIP in a post-exposure scenario, it was important to select an AAV capsid that promoted rapid transgene expression. While a number of studies have quantified luciferase reporter gene expression from various AAV capsids following different routes of administration [50-53], the focus has largely been on quantification of signal longevity as opposed to characterizing the kinetics of transgene expression at early time points. Unexpectedly, all of the AAV capsids evaluated in this study generated a robust luciferase signal that was detectable 24 hr after a single IM injection. AAV6.2FF outperformed AAV6 and all other capsids evaluated, without wishing to be bound by theory, this may be partly due to the removal of surface-exposed tyrosine residues, which is known to mitigate capsid ubiquitination and degradation, but this does not explain the entire beneficial effect [9]. Given the remarkable speed of transgene expression, especially from AAV6.2FF, this strongly shows that with the appropriate capsid, AAV-VIP could potentially be applied in a post-exposure scenario or during ring vacation strategies during rapidly spreading hot zones.

Due to their ability to mediate high-level transgene expression, AAV8 and AAV9 are popular choices for AAV-antibody gene transfer [42, 45]; however, migration of transgene expression from the site of IM administration has been reported for AAV8 [54], similar to what was observed in this Example. A large proportion of AAV9-mediated transgene expression (70-90%) is detected outside the muscle, in what appears to be the liver, within the first 24 hr post-vector administration. Exactly how AAV8/9 migrate to other tissues early after IM administration is not known, but without wishing to be bound by theory, it is plausible that these vectors transduce a population of short-lived immune cells that travel to the liver. Despite that systemic administration of AAV-DJ almost exclusively targets the liver [3], transgene expression from AAV-DJ remained intramuscular, unlike AAV8/9. Delivery of AAV-mAbs IM is more practical and safer than systemic administration; therefore, the present inventors sought to select a capsid that does not migrate away from the muscle.

The expression profiles of two distinct AAV-mAbs, one with neutralizing activity (2G4) and one without (5D2) and demonstrate that both are capable of high-level expression in mice were characterized. AAV-2G4 consistently produced higher ELISA values in both IM and IN treated groups. However, since the mAb transgenes were murine IgG2a molecules it was not possible to quantify the amount of mAb in the serum and higher ELISA OD values do not necessarily indicate higher expression.

Co-transfection severely impacted functional mAb output in vitro; however, co-administration of AAV-2G4 and AAV-5D2 did not significantly alter mAb expression in vivo. Without wishing to be bound by theory, it may be that a higher proportion of cells in vitro were co-transfected, which could lead to the production of improperly paired antibody chains and therefore poorly functional mAbs. A greater number of available cells in vivo may reduce the likelihood of co-transduction; therefore, although undesirable heterodimers may still be generated, they are not the primary product and do not seem to impede overall serum concentrations of functional mAbs.

The AAV-2G4/AAV-5D2 cocktail conferred 100% protection with only a seven-day lead-time before EBOV challenge. This is the shortest prophylactic window in which AAV-mAb expression has demonstrated full protection against EBOV challenge and the first time that a non-neutralizing mAb has been shown to protect against EBOV via VIP. Also observed is the minimal extension of life in groups with partial protection. Although there was a sole survivor in the three-day lead-time group, all of its cage-mates died the same day as the untreated controls and the one mouse that succumbed to infection in the AAV-2G4 monotherapy group died only one day after the controls. With minimal protection conferred by the AAV-2G4/AAV-5D2 cocktail at three dpa, it appears that the minimum lead-time required for full protection was missed, which would be between seven and three dpa. These challenge experiments were conducted using C57BL/6 mice prior to the observation that BALB/c mice displayed significantly greater 5D2 mAb levels, therefore, without wishing to be bound by theory, it may be that using mice on a BALB/c background could show better efficacy.

Both of the non-neutralizing AAV-mAb monotherapies provided 100% protection with 14 days lead-time, while the only neutralizing mAb we examined (2G4) was partially effective. These results are similar to what Qiu et al observed when mice were treated with these same mAbs intraperitoneally and challenged with MA-EBOV [34]. Since 5D2 and 7C9 were engineered as murine IgG2a antibodies with functional Fc domains, they may induce complement-dependent cytotoxicity or antibody-dependent cell-mediated cytotoxicity in place of viral neutralization.

Despite pre-clinical success in post-symptomatic treatment of non-human primates (NHPs) with ZMapp [55], a clinical trial treating humans with the mAb cocktail failed to significantly improve patient outcome [56]. Limited doses of ZMapp were available during the West Africa outbreak and it was not feasible to scale-up production quickly enough since the mAbs were manufactured in *Nicotiana benthamiana*. Large-scale recombinant mAb production is technically challenging due to specific glycosylation requirements making the manufacturing process slow and expensive [26]. AAV-mediated mAb production avoids these issues and additionally, vectors can be lyophilized and stockpiled [57]. Furthermore, a single dose of AAV-mAb provides circulating mAbs for much longer periods of time than passively administered mAbs. Since AAV-mAb expression is independent of the host immune response it can provide protection to seniors or the immunocompromised, which offers an advantage over traditional vaccines. Alternatively, in healthy individuals, AAV-mAb expression offers a stopgap, slowing viral replication to allow the immune response time to catch up to the infection and generate natural immunity [41]. The AAV-mAb platform can be applied to counter bioterrorism or to treat emerging viral diseases rapidly as the only constraint is a protective mAb sequence, which in many cases is already available. While post-exposure AAV-mAb therapy is not yet feasible, the mAbs used in ZMapp and in this study are of a first generation and recently countless, more potent, mAbs have been characterized that may facilitate this advancement [58-60].

Example 3

Vectorized Expression of Filovirus-Specific Monoclonal Antibodies are Protective at Low Concentrations This Example further explores immunity conferred by the AAV6.2FF-mAb vector system, including the effect on the endogenous humoral immune system as well as the ability to express human IgG1 in immunocompetent mice using the platform describe herein.

Materials and Methods

AAV Vectors

All monoclonal antibody genes were expressed using the bicistronic expression cassette developed by Fang et al. [61] and optimized by Balazs et al. [39], including a CASI promoter, heavy and light chains separated by a furin-2A cleavage site, a woodchuck hepatitis virus post-transcriptional regulatory element (WPRE) and SV40 poly A signal between the AAV2 inverted terminal repeats (ITR). Murine mAbs were engineered using the murine IgG2a heavy chain and kappa light chain sequences while human mAb vectors utilized the human IgG1 heavy chain and lambda light chain. All vectors were produced using the AAV6.2FF capsid [62] following the methods described in Example 2.

Mice

Experiments involving animals were approved by the University of Guelph and the Canadian Science Centre for Human and Animal Health Animal Care Committees according to the guidelines outlines by the Canadian Council on Animal Care. All experiments were completed using six-week-old female BALB/c mice (Charles River). Vector administrated intramuscularly (IM) were diluted to a 40 μl volume in PBS and administered to the gastrocnemius muscle using a 29-gauge needle. AAV cocktails were administered at equimolar vg quantities by separate injections to each hind leg to prevent co-transduction. Intranasal (IN) vector instillation was completed as described in Example 2.

Biodistribution Analysis

Genomic DNA was extracted from mouse tissues using the Qiagen DNeasy Blood & Tissue kit. AAV ITR copy number was quantified by Taqman qPCR [45] and normalized by nanodrop DNA concentrations.

Enzyme-Linked Immunosorbent Assays

Serum samples were collected by saphenous bleed in EDTA collection tubes and aliquoted for storage at −80° C. Human IgG and murine IgG concentrations were quantified using commercially available kits (Abcam 195215 and 157719). Reciprocal antibody titers were determined by coating half area 96 well plates (Corning) with 1p g/mL recombinant EBOV GP (IBT Bioservices 0501-001), MARV GP (IBT Bioservices 0506-015), EBOV VP40 (IBT Bioservices 0564-001), Influenza A virus HA (SinoBiological 11684-V08H) or mAb 100 (purified by protein G column) protein overnight at 4° C. Plates were washed four times with 0.2% PBS-Tween20 (PBS-T) and blocked with SuperBlock™ buffer (ThermoFisher 37515). Two-fold serial dilutions of serum were incubated at 37° C. for one hour and then washed four times with PBS-T. Secondary antibody (Pierce P31430) was added and incubated at a 1:2,000 dilution for one hour at 37° C. washed four times with PBS-T and then incubated with TMB substrate (Pierce P134021) for 15 minutes before acquiring absorbance values at 650 nm on a plate reader. Reciprocal titer was defined as the highest serial serum dilution that gave an $OD_{650}$ value 2-fold greater than the mean of the negative control wells.

Challenge Models

Ebola and Marburg virus challenge studies were completed in the containment level 4 facility at the Canadian Science Centre for Human and Animal Health. Mice were challenged with 1,000 times the lethal dose for 50% of animals ($LD_{50}$) of mouse-adapted Ebola virus (MA-EBOV; strain Mayinga) or mouse-adapted Marburg virus (MA-MARV; strain Angola) by intraperitoneal (IP) injection. Post-exposure Ebola virus challenges were completed using an IP dose of 100 times $LD_{50}$. Non-lethal influenza virus (strain PR8; A/PR/8/34(H1N1)) challenge was completed by IP injection of 600 hemagglutinin (HA) units diluted in PBS to a 500 μl volume for both primary and secondary exposures.

Statistics

Statistical analyses were performed using GraphPad Prism 7 software. Kaplan-Meyer survival plots were analyzed by Mantel-Cox log rank test for statistical significance compared to mock treated controls. Results were considered significant when p-values were s0.05. All error bars represent the standard deviation of the mean.

Results

AAV6.2FF-Mediated Expression of Murine IaG2a Antibodies Extends Beyond 400 Days

Figure 18:
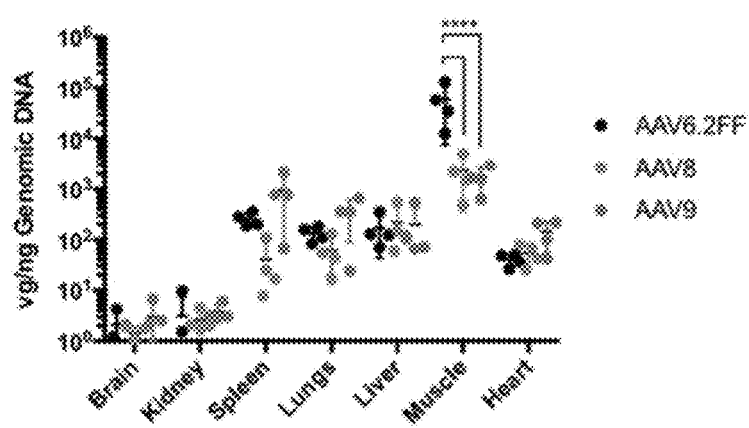
FIG. 18 shows biodistribution of AAV6.2FF, AAV8 and AAV9 following intramuscular delivery. BALB/c mice (n=4/group) were injected IM with $1 \times 10^{11}$ vg of AAV6.2FF-, AAV8- or AAV9-Luciferase and were euthanized five days later for tissue harvest. Genomic DNA was extracted and analyzed by qPCR for AAV ITR copy number, which was normalized to input DNA concentration. Muscle samples were harvested from the site of AAV injection. Two-way ANOVA was used to determine statistical difference between the number of AAV genomes for 3 serotypes in each tissue. *$p<0.0001$.

The 2G4 and 5D2 mAbs in "first-generation" vectors, AAV6.2FF-2G4 and AAV6.2FF-5D2, were engineered as murine IgG2a to promote optimal effector functions in mice as well as to avoid a potential immune response against a foreign immunoglobulin. AAV6.2FF had a stronger tropism for the muscle than AAV8 or AAV9, both popular serotypes for similar applications (FIG. 18).

Figure 19A:
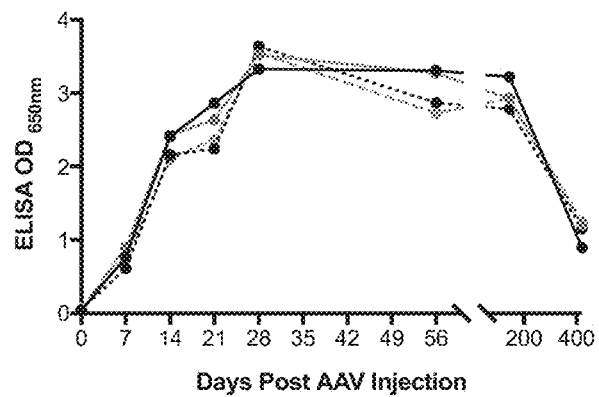
FIGS. 19A and 19B show long-term expression of 5D2. $2 \times 10^{11}$ vg of AAV6.2FF-5D2 (murine IgG2a) was administered by (FIG. 19A) intramuscular injection or (FIG. 19B) intranasal instillation to BALB/c mice. Serum samples were collected at weekly intervals, which were analyzed and quantified by EBOV GP ELISA at a 1:100 dilution. Each curve represents data derived from an individual mouse.
Figure 19B:
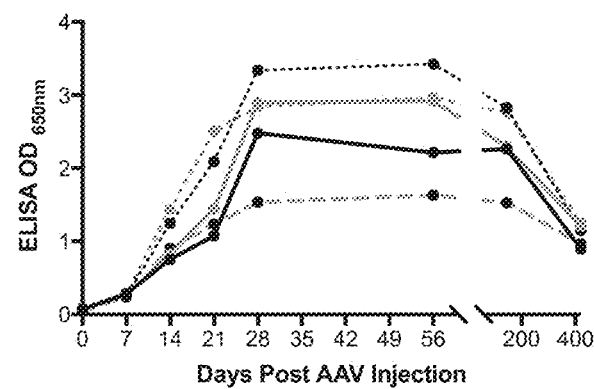

Peak AAV6.2FF-mediated expression of mAbs was observed 28 days post-IM or IN vector administration and these high concentrations plateaued for more than 146 days (FIGS. 19A and 19B). At some point between 146 and 420 days, mAb concentrations decreased for both methods of vector delivery, however these terminal OD values are still greater than 0.8, which is protective mAb concentration (see Table 2). Despite IM injection yielding much more consistent serum mAb concentrations than IN administration of the same vector dose ($2 \times 10^{11}$ vg), both routes demonstrated very similar patterns of mAb expression kinetics over the 420-day experiment, regardless of the magnitude of peak expression.

AAV6.2FF-2G4/AAV6.2FF-5D2 Treatment Prevents Both Morbidity and Mortality

Figure 20A:
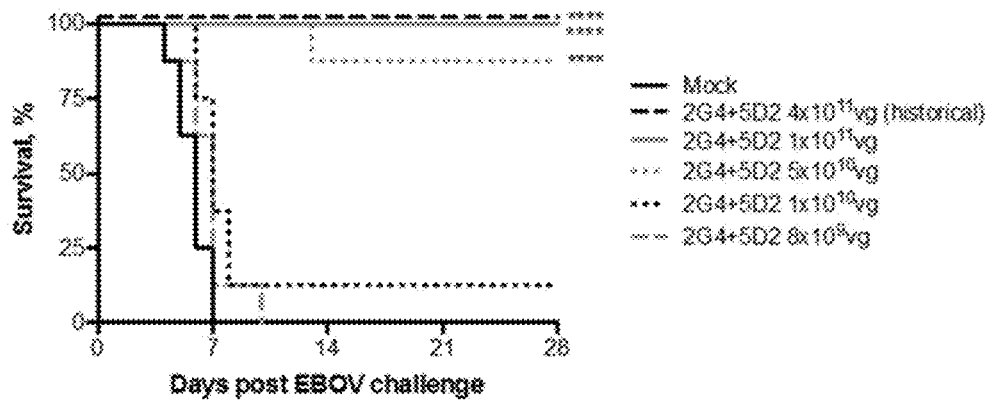
FIGS. 20A and 20B show effects of AAV6.2FF-2G4/ AAV6.2FF-5D2 dose reduction. BALB/c mice (n=8/group) were administered various doses of the AAV6.2FF-2G4/ AAV6.2FF-5D2 cocktail IM. 28 days following AAV administration, mice were challenged with $1000 \times LD_{50}$ MA-EBOV and monitored for (FIG. 20A) survival and (FIG. 20B) weight loss (plotted as group averages). ****$p<0.0001$.
Figure 20B:
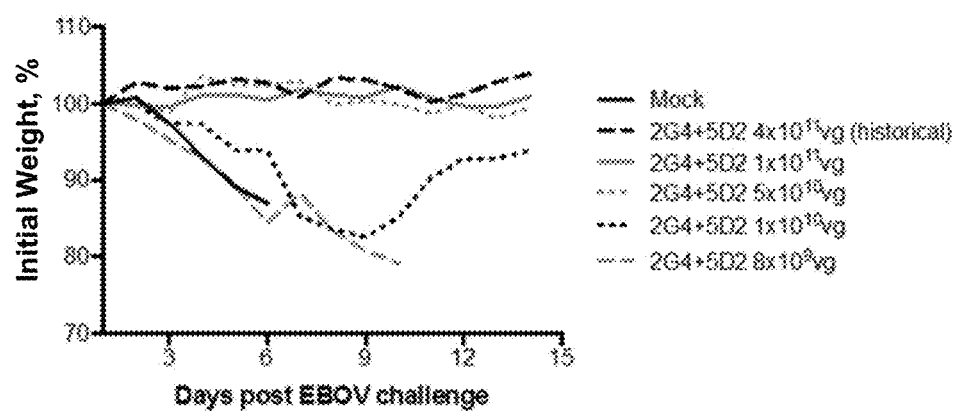

In an effort to determine the minimum therapeutic dose of AAV6.2FF-2G4/AAV6.2FF-5D2 vector cocktail, which at $4 \times 10^{11}$ vg (equimolar vector concentrations) confers 100% survival with treatment only seven days prior to challenge, a dose reduction experiment was completed in which mice were treated 28 days prior to challenge at doses ranging from $4 \times 10^{11}$ vg to $8 \times 10^9$ vg. At doses of $4 \times 10^{11}$, $1 \times 10^{11}$, and $5 \times 10^{10}$ vg, 100%, 100% and 88% survival were observed, respectively (FIG. 20A). $1 \times 10^{10}$ vg resulted in a single survivor (12.5% survival) and the lowest dose, $8 \times 10^9$ vg did not protect any animals. There was no morbidity associated with the survivors of the $4 \times 10^{11}$ vg, $1 \times 10^{11}$ vg and $5 \times 10^{10}$ vg doses, however the mouse that survived at the $1 \times 10^{10}$ vg dose did experience significant weight loss prior to recovery (FIG. 20B).

Figure 21A:
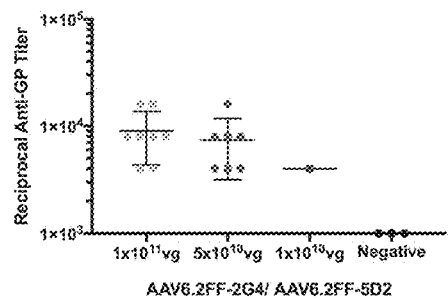
FIGS. 21A-21D show EBOV GP reciprocal antibody titers pre and post challenge. Serum from the surviving mice in the AAV6.2FF-2G4/AAV6.2FF-5D2 dose reduction experiment of FIGS. 20A and 20B ($1 \times 10^{11}$ vg n=8, $5 \times 10^{10}$ vg n=7, $1 \times 10^{10}$ vg n=1) was analyzed by EBOV GP ELISA (FIG. 21A) immediately prior to challenge (28 days post AAV administration) and (FIG. 21B) 28 days post challenge.
Figure 21B:
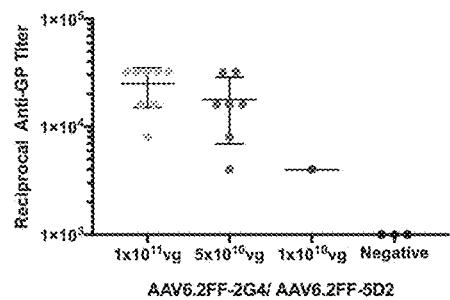
Figure 21C:
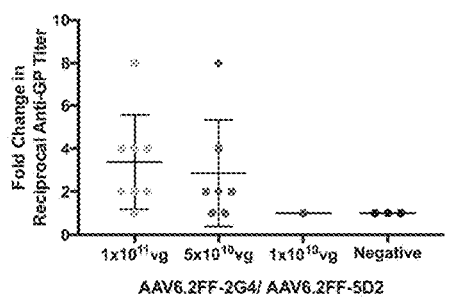
Figure 21D:
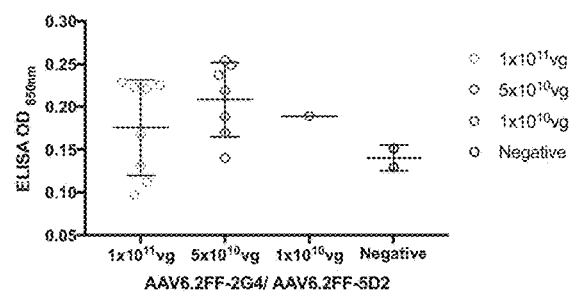

Prior to challenge, serum was collected from the mice in the dose reduction experiment to determine the reciprocal EBOV GP antibody titer (FIG. 21A). These titers represent the concentrations of AAV6.2FF-expressed 2G4 and 5D2 28 days post-vector administration. GP antibody titers were also determined 28 days post-EBOV challenge to investigate the potential increase in GP antibody concentrations due to the contribution of the endogenous humoral response against EBOV (FIG. 21B). The difference in pre- and post-challenge GP antibody titers ranged from a one- to eight-fold increase, however all of these mice survived. Therefore, the pre-challenge GP antibody titers were sufficiently protective (FIG. 21C). Serum from mice surviving 28 days post-EBOV challenge was also examined for antibodies against the EBOV matrix protein, VP40 (FIG. 21D).

VP40 antibodies were not detected above background in any mice. This result combined with minimal increase in GP antibody titers post-challenge and negligible weight loss indicate that AAV6.2FF-2G4/AAV6.2FF-502 treatment likely conferred sterilizing immunity against EBOV infection onto these mice.

Figure 22A:
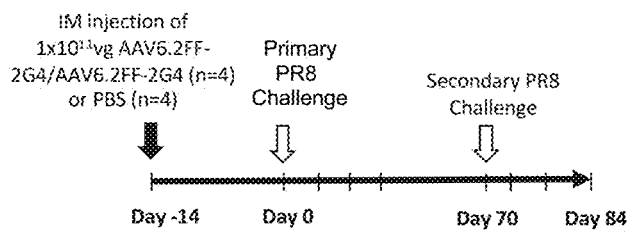
FIGS. 22A-22D show endogenous humoral response to influenza A virus in the context of protective 2G4/5D2 antibody titers.
Figure 22B:
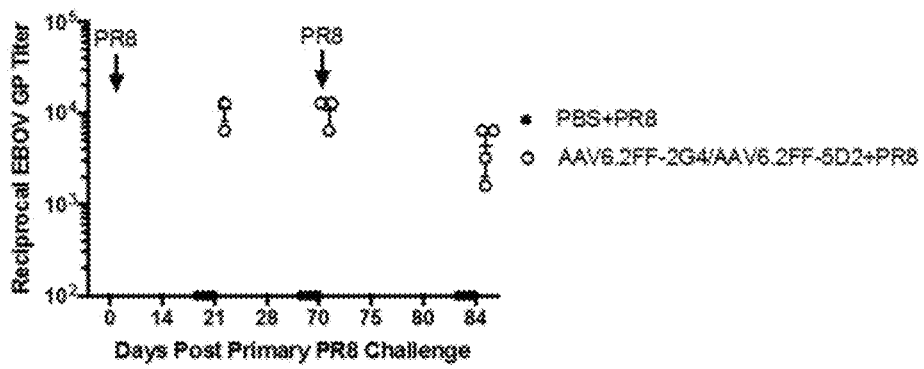
Figure 22C:
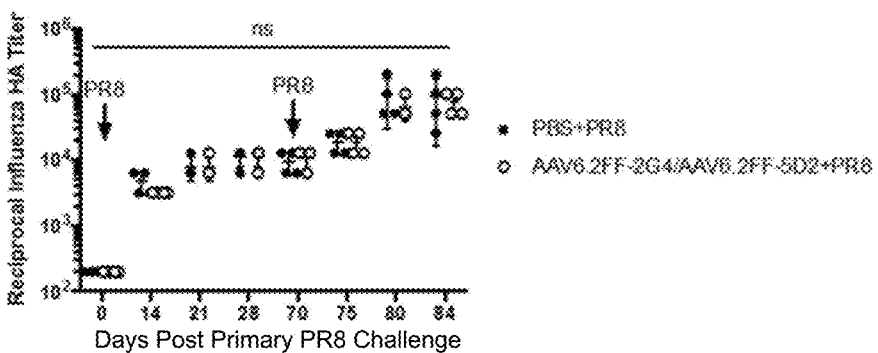
Figure 22D:
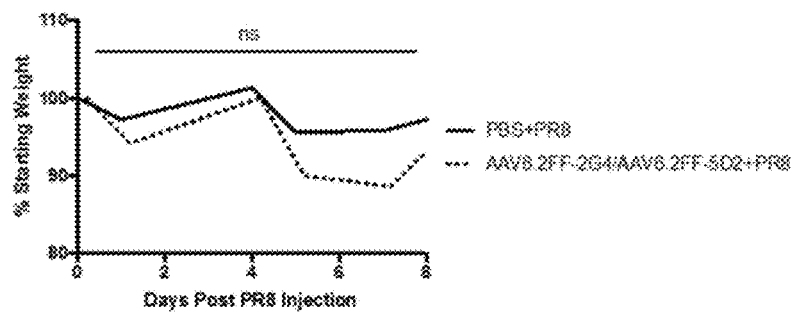

Protective mAb Concentrations Mediated by AAV6.2FF-2G4/AAV6.2FF-5D2 Did not Impact the Endogenous Humoral Response to a Heterologous Challenge To investigate the ability of the endogenous humoral immune system to respond appropriately to a heterologous infection in the context of AAV6.2FF-2G4/AAV6.2FF-5D2 expression, mice pre-treated with either AAV6.2FF-2G4/AAV6.2FF-5D2 or PBS were exposed to a non-lethal challenge of influenza A virus, followed by quantification of the antibody response against the influenza HA protein was compared in both groups (FIGS. 22A-22D). Reciprocal antibody titers against the EBOV GP reached protective concentrations in AAV6.2FF-2G4/AAV6.2FF-5D2 treated mice and were not above background in the PBS-treated group (FIG. 22B). Influenza virus HA antibody titers were indistinguishable between the treatment groups for both primary and secondary influenza virus exposures (FIG. 22C), indicating AAV6.2FF-mAb treatment did not hamper the primary or secondary B cell response in mice. Mice were also weighed throughout the first eight days following primary influenza virus infection and no statistical difference between treatment groups was observed (FIG. 22D).

Serum mAb 100 Concentrations >100 µg/mL Confer a Survival Advantage Against Ebola Virus Challenge Murine IgG2a antibodies were selected to vectorize in part to avoid an immune response against a human IgG. However, B cell mining of human survivors has resulted in exceptionally potent mAbs against filoviruses and expressing human antibodies in mice would streamline preclinical development. An AAV6.2FF vector was engineered to express mAb 100 as a human IgG1 (AAV6.2FF-100) and administered IM to mice at a dose of $5 \times 10^9$ vg and the concentrations of human IgG were monitored over 17 weeks (FIGS. 23A-23D). The use of human antibodies allows precise quantification of the amount of transgene expression mediated by AAV, since endogenous Ab responses cannot confound the assay. Concentrations of mAb 100 steadily rose at each time point, indicating continuous expression and, without wishing to be bound by theory, possible recycling of the human IgG1 by murine FcRn [63]. Furthermore, mAb concentrations over 200 µg/mL at 17 weeks indicates that an immune response against this human antibody was not an overtly limiting factor.

Figures 23A, 23B:
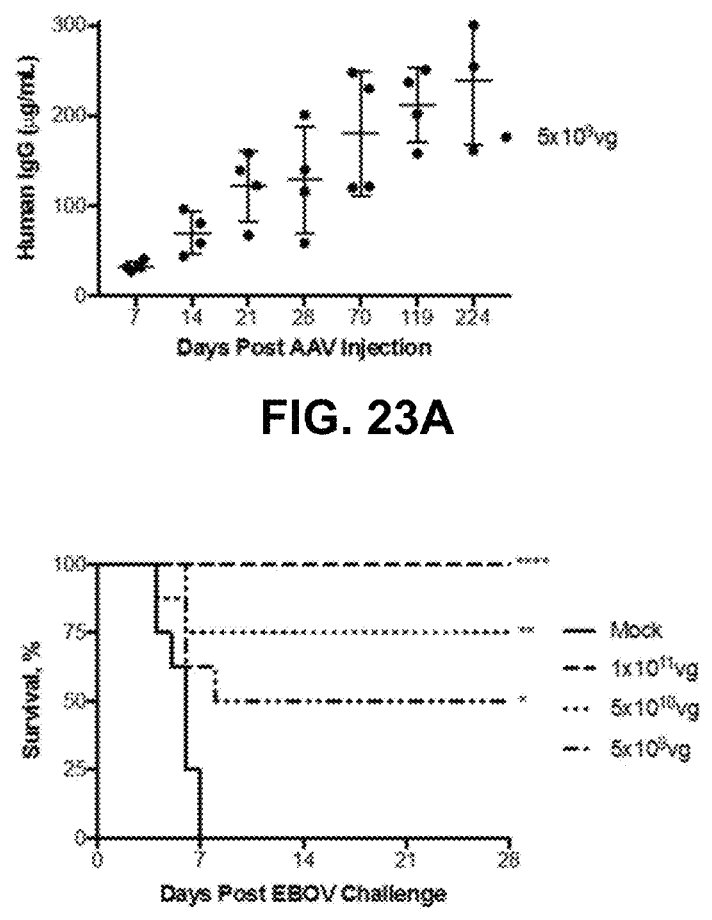
Figures 23C, 23D:
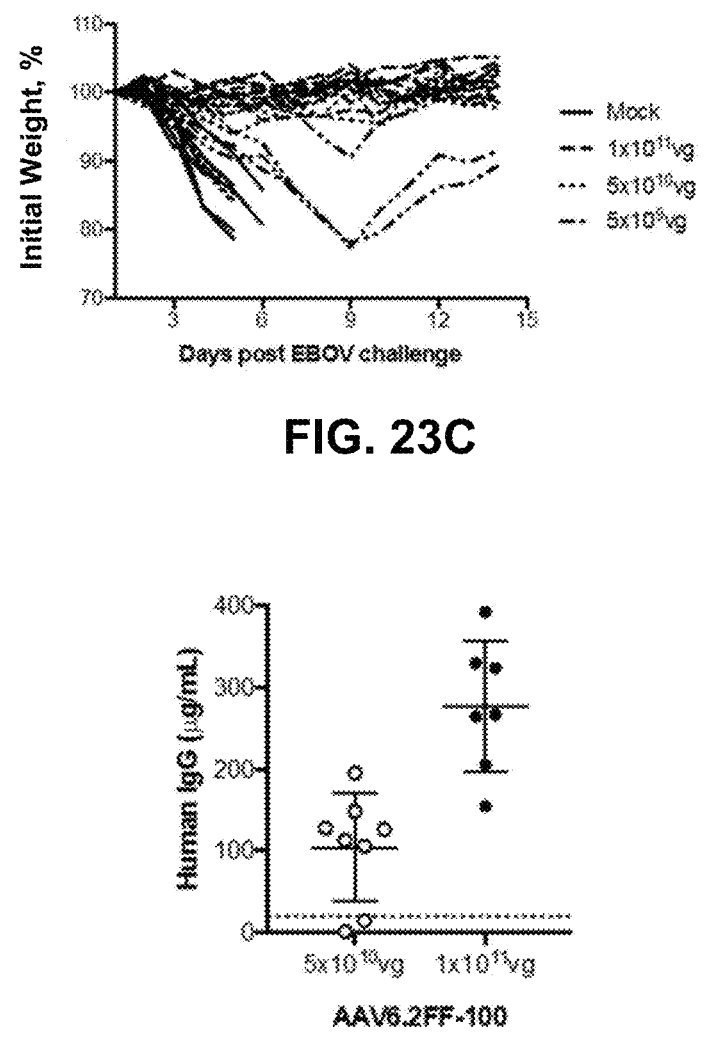

A $1 \times 10^{11}$ vg dose of AAV6.2FF-100 conferred 100% survival, while $5 \times 10^{10}$ vg and $5 \times 10^9$ vg resulted in 75% and 50% survival respectively (FIG. 23C). Weight loss was not observed for any mice in the group that received $1>10^{11}$ vg and similarly in the $5 \times 10^{10}$ vg group, none of the surviving mice experienced any weight loss, showing AAV6.2FF-100 was able to generate sterilizing immunity at these doses (FIG. 23D). At the lowest dose tested ($5 \times 10^9$ vg), four of eight mice survived the challenge and three of these survivors experienced weight loss, potentially demonstrating that the minimum efficacious dose was being approached. In the AAV6.2FF-2G4/AAV6.2FF-5D2 dose reduction experiment, the lowest dose of $8 \times 10^9$ vg resulted in 0% protection, while an even lower dose of $5 \times 10^9$ vg of AAV6.2FF-100 yielded 50% survival, highlighting the benefit of selecting high quality mAbs for expression.

Serum samples were collected immediately prior to challenge, allowing quantification of the mAb 100 concentration at this time to further understand the minimum mAb concentration required to confer protection. The $1 \times 10^{11}$ vg dose yielded an average human IgG concentration of 277 µg/mL, while half this dose of AAV6.FF-100, $5 \times 10^{10}$ vg, generated an average concentration of 104 µg/mL, demonstrating scaling of the vector dose to output mAb concentration is not linear. Two of eight mice in the group that received $5 \times 10^{10}$ vg had very low concentrations of mAb 100 in the serum compared to the rest of the group (1.1 µg/mL and 14.5 g/mL, versus a mean of 136 g/mL for the other six mice), which was likely due to poor administration of the vector to the gastrocnemius muscle and the EBOV challenge was lethal in these two mice. Of the mice that survived, the serum human IgG concentrations ranged from 105-196 g/mL and 155-392 µg/mL for the groups that received $5 \times 10^{10}$ vg and $1 \times 10^{11}$ vg, respectively. Therefore, the minimum protective threshold was somewhere between 14.5-105 µg/mL. This range was determined as such because pre-challenge blood samples were not collected from mice that received the dose of $5 \times 10^9$ vg, which likely would have narrowed the range of the protective threshold for AAV6.2FF-100.

Post-Exposure Administration of AAV6.2FF-mAbs Results in Partial Survival

Vectorized mAb expression had clear advantages as an alternative to long-term passive antibody therapy. It was then investigated if AAV6.2FF-mAbs would be effective in a post-exposure setting since these vectors take time to generate protective mAb concentrations. A traditional challenge dose of $1,000 \times LD_{50}$ is designed to robustly test a vaccine's ability to generate immunity in the host, however this dose does not accurately recapitulate contact exposure to Ebola virus.

The mouse model of Ebola virus infection is rapid and stringent, with death usually occurring in five to seven days. In most cases of human infection there is an incubation period of typically four to nine days post-exposure to the virus prior to the presentation of clinical signs and symptoms. To more accurately model the course of clinical infection, the challenge dose of MA-EBOV was reduced to $100 \times LD_{50}$ to investigate whether post-exposure use of AAV6.2FF-mAbs could provide protection.

Figures 24A, 24B:
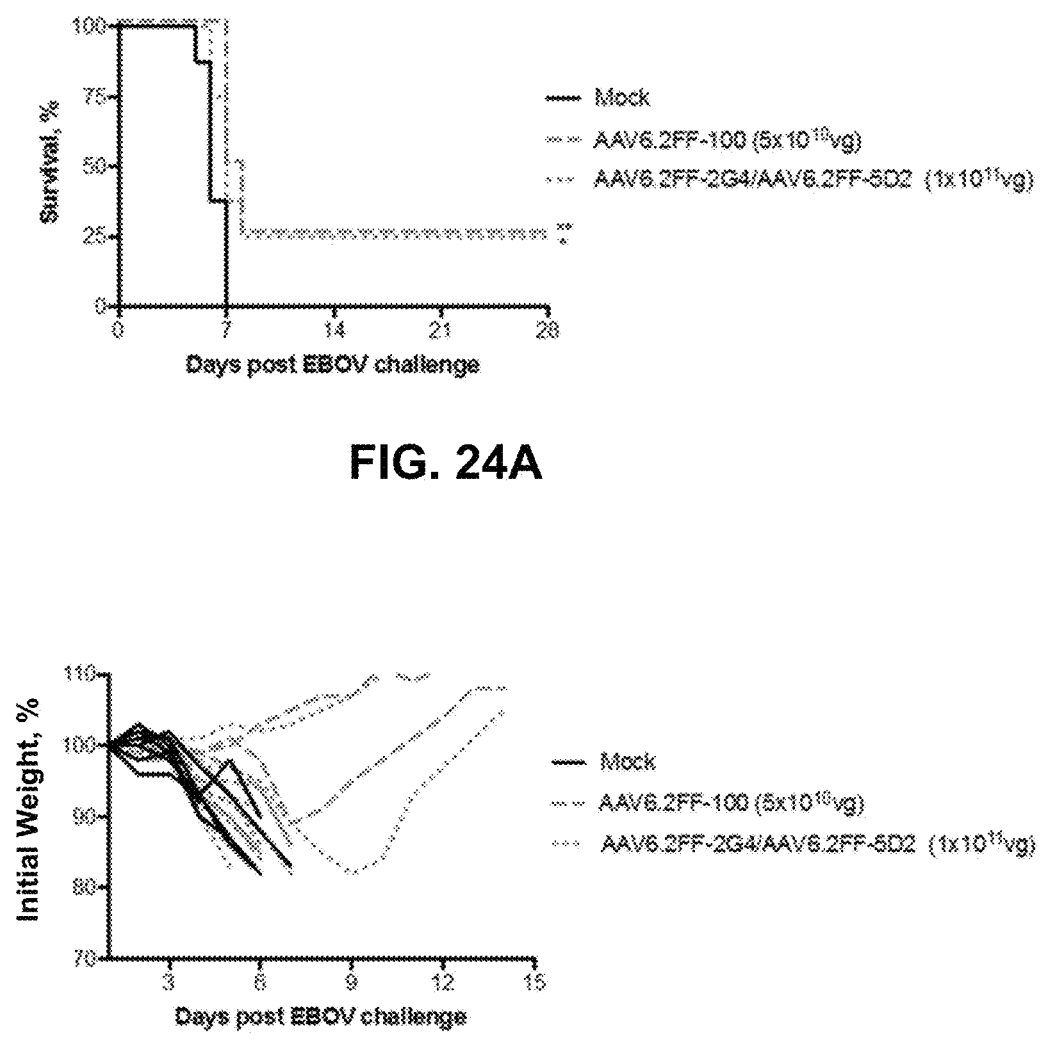

Groups of mice were treated IM with either $1 \times 10^{11}$ vg of AAV6.2FF-2G4/AAV6.2FF-5D2 or $5 \times 10^{11}$ vg of AAV6.2FF-100 immediately following IP injection of $100 \times LD_{50}$ MA-EBOV. Surprisingly, two of eight mice from each treated group survived despite 100% death in the mock group (FIG. 24A). Of the surviving mice, one from each treated group experienced weight loss, while the other did not, steadily gaining weight throughout the monitoring period (FIG. 24B). It is important to note that 20% survival was observed for both treatments, despite AAV6.2FF-100 being administered at half the dose of AAV6.2FF-2G4/AAV6.2FF-5D2, clearly demonstrating the superiority of mAb 100 compared to 2G4 and 5D2.

Figure 25A:
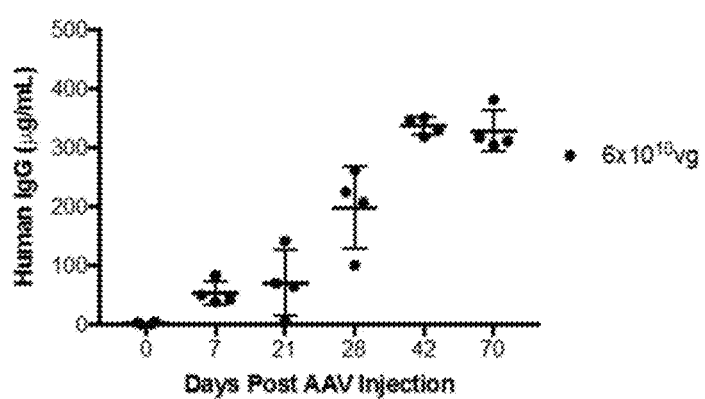
FIGS. 25A-25D show AAV6.2FF-MR191 mediates complete protection from Marburg virus challenge.
Figure 25B:
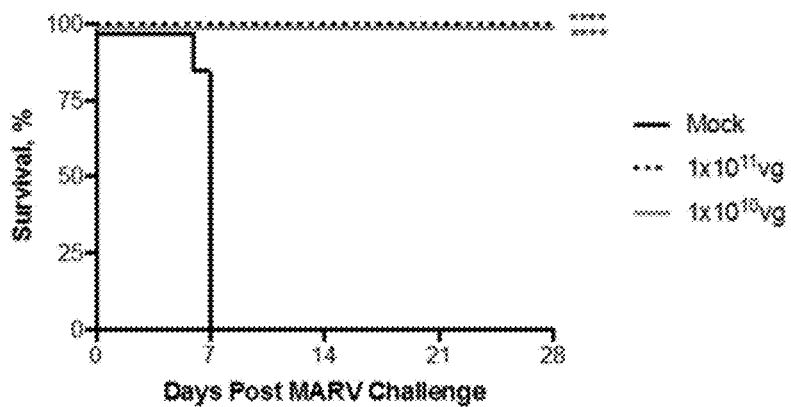
Figure 25C:
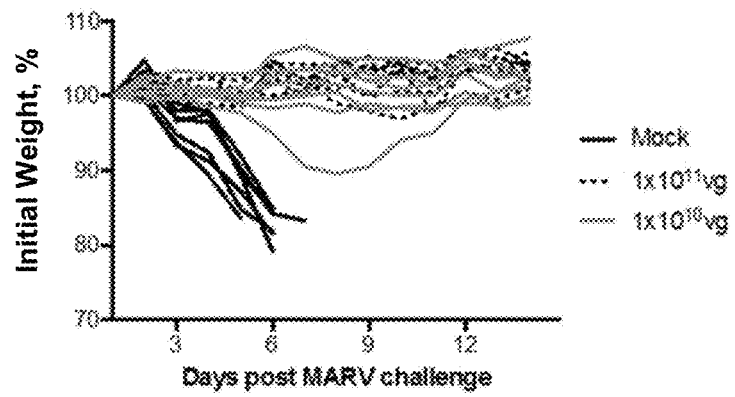
Figure 25D:
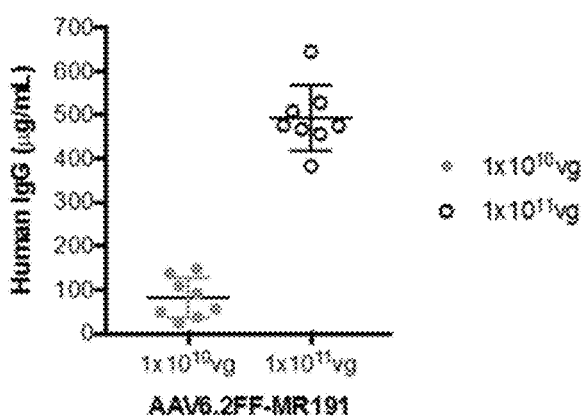

Vectorized Expression of MR191 Confers a Survival Advantage at Concentrations as Low as 24 µg/mL With the success of AAV6.2FF-mAb vectors for the prevention of Ebola virus infection, inventors sought to expand the platform described herein to Marburg virus, a closely related cousin of Ebola virus, to investigate whether AAV6.2FF-mAb vectors would be effective in a new infectious disease model. AAV6.2FF-MR191 was administered IM to mice at a dose of $6 \times 10^{10}$ vg resulted in human IgG concentrations of over 300 µg/mL by six to ten weeks post-injection (FIG. 25A). In seven days, serum MR191 concentrations reached 38-83 µg/mL. Next, inventors investigated the protective efficacy of AAV6.2FF-MR191 at two doses in a lethal mouse model of Marburg virus infection. A high dose of $1 \times 10^{11}$ vg and a low dose of $1 \times 10^{10}$ vg both yielded 100% survival with vector administration 28 days prior to challenge (FIG. 25B). With the exception of one mouse in the low dose group, none of the animals experienced weight loss (FIG. 25C), showing these doses of AAV6.2FF-MR191 confer sterilizing immunity similar to the AAV6.2FF-2G4/AAV6.2FF-5D2 and AAV6.2FF-100 vectors. Serum samples were collected from these mice immediately prior to challenge and human IgG concentrations were quantified (FIG. 25D). The $1 \times 10^{10}$ vg and $1 \times 10^{11}$ vg doses of AAV6.2FF-MR191 generated antibody concentrations between 24-137 µg/mL and 383-645 µg/mL respectively. Each one of these MR191 concentrations resulted in survival, demonstrating the potency of MR191 and also highlighting that high vector doses were not required to confer protective serum mAb concentrations. The single mouse that lost weight did not have the lowest human IgG concentration prior to challenge. In fact, it had the second lowest pre-challenge titer (37.4 ug/mL). It is also worth noting that this mouse lost only 10% of its pre-challenge weight, which although significant, was not yet approaching lethality. The expansion of this AAV6.2FF-mAb expression system to Marburg virus demonstrates the flexibility of the platform beyond Ebola virus.

Figure 26A:
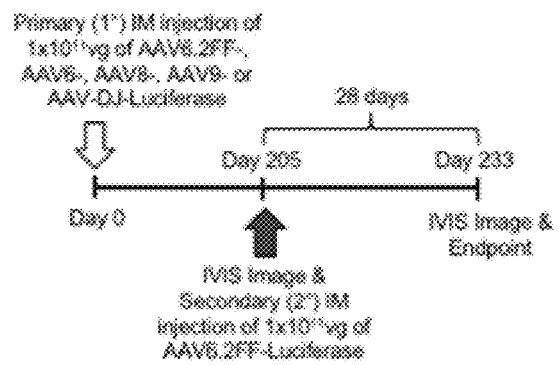
FIGS. 26A-26F show intramuscular administration of AAV6.2FF-Luciferase following prior exposure to heterologous or homologous vectors results in substantial transgene expression.
Figure 26B:
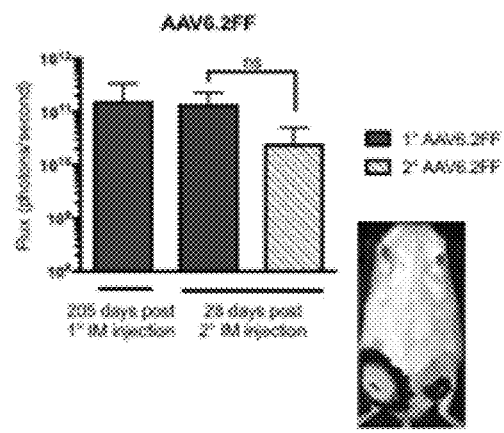
Figure 26C:
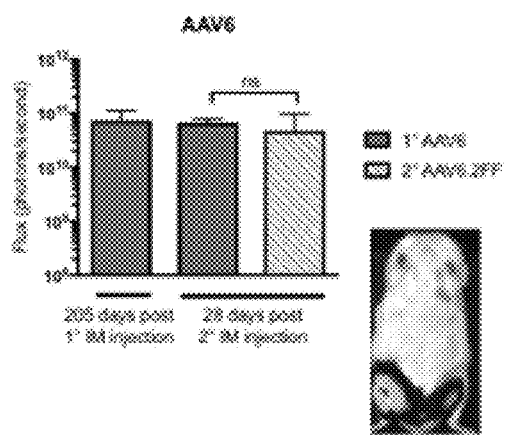
Figure 26D:
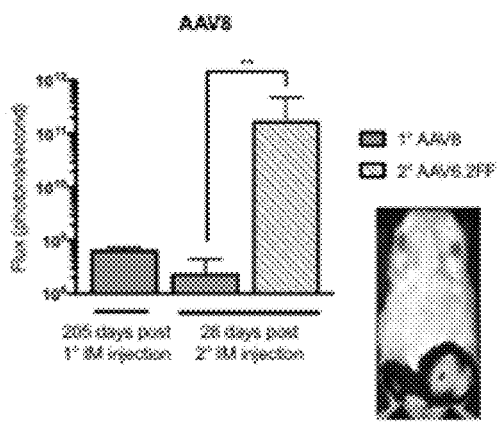
Figure 26E:
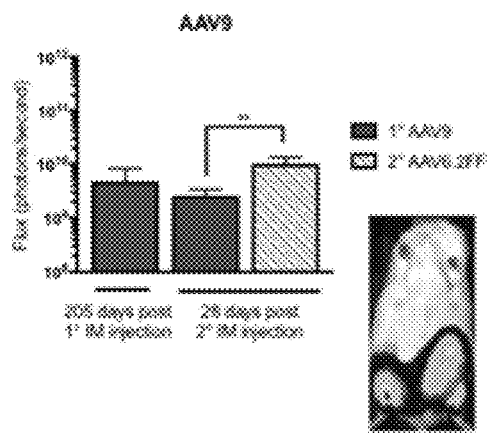
Figure 26F:
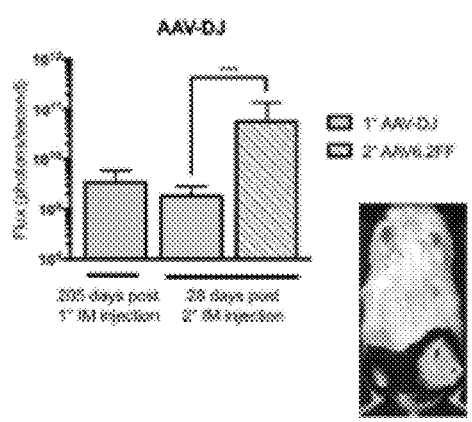

AAV6.2FF Vectors can be Effectively Re-Administered to Mice with Prior Exposure to the Capsid In order to function as a practical platform, AAV6.2FF-mAb vectors should be able to be administered to individuals with pre-existing vector immunity from either natural exposure or previous AAV6.2FF-mAb vector administration. First, luciferase expressing AAV vectors were investigated by observing transgene expression from IM administration of AAV6.2FF-Luciferase to the right calf muscle 205 days after injection with either a homologous or a heterologous vector in the left flank (FIG. 26A). Secondary IM exposure of AAV6.2FF-Luciferase generated strong transgene expression; approaching approximately one log lower than the luciferase expression observed after the primary injection (FIG. 26B). This indicated either IM injection of this vector resulted in a minimal AAV-specific immune response or that IM injection was largely able to mostly circumvent any pre-existing capsid-specific immunity. Secondary AAV6.2FF injection in mice previously administered AAV6 yielded transgene expression as strong as what was observed for the primary vector (FIG. 26C). AAV6.2FF-Luciferase injected in mice previously administered AAV8, AAV9 or AAV-DJ generated stronger transgene expression than any of the primary vectors (FIGS. 26D-26F).

Figure 27A:
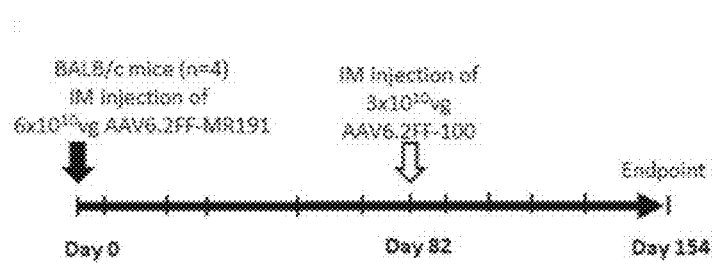
FIGS. 27A-27D show attempted re-administration of a second AAV6.2FF-mAb vector encoding a heterologous human IgG.
Figure 27B:
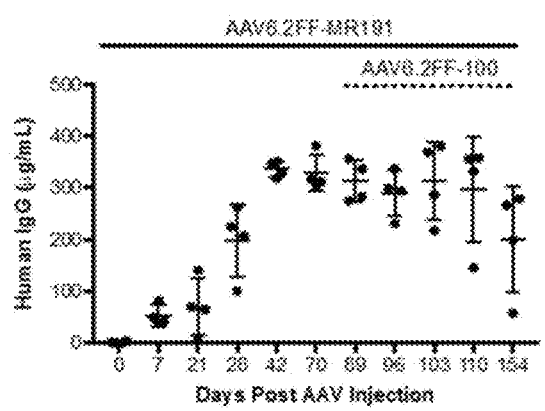
Figure 27C:
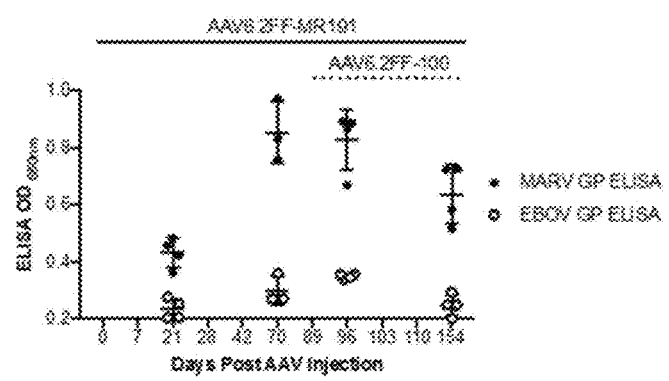
Figure 27D:
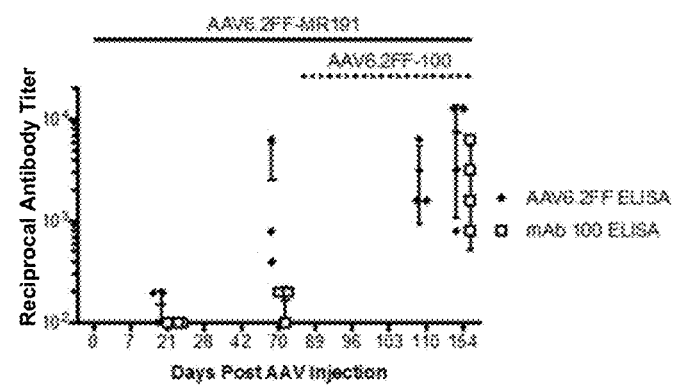

Second, re-administration of AAV6.2FF was investigated in the context of two distinct AAV6.2FF-mAb vectors: AAV6.2FF-MR191 and AAV6.2FF-100. Expression of MR191 was monitored following vector administration for 70 days (FIG. 27A). These mice were subsequently treated with AAV6.2FF-100 to determine if both MARV and EBOV GP antibodies could be detected at protective concentrations. Human IgG concentrations were monitored before and after treatment with AAV6.2FF-100 and appeared to have been impacted by prior exposure to the heterologous AAV6.2FF-mAb vector (FIG. 27B). There was a dip in human IgG concentrations observed after administration of AAV6.2FF-100 administration that subsequently stabilized in three out of four mice. The fourth mouse had significantly declining human IgG concentrations at endpoint. Only MARV GP mAbs were detected by ELISA at time points following administration of the second vector, and EBOV GP mAbs were not detected above background indicating re-administration of the same vector expressing a heterologous antibody was unsuccessful (FIG. 27C). The endogenous humoral response generated against the AAV6.2FF capsid and the human IgG backbone in pre- and post-secondary vector administration was evaluated by ELISA. The humoral immune response against the capsid and the antibody response against the human antibody backbone increased (FIG. 27D).

Discussion

The lack of significant weight loss in mice treated with AAV6.2FF-2G4/AAV6.2FF-5D2, animals combined with minimal increases in pre- to post-challenge GP antibody titers in some mice as well as negative VP40 antibody titers showed these AAV6.2FF-mAb vectors were able to induce sterilizing immunity, with minimally immunogenic vectors. VP40 is a much less dominant immunological epitope than GP, therefore the virus must be able to infect cells and replicate in order for VP40 to be displayed to the immune system. VP40 is not present on the surface of EBOV virions and a lack of VP40 antibodies is consistent with sterilizing immunity.

Although these 2G4/5D2 mAb concentrations were sufficient to prevent both morbidity and mortality, it was unclear if they would affect the endogenous humoral response, similarly to how colostrum prevents an infant from effectively generating a robust antibody response to a vaccine [64]. Nonetheless, the present inventors showed that naive mice or those treated with AAV6.2FF-2G4/AAV6.2FF-5D2 responded with equivalent influenza HA antibody titers, thus were able to respond normally to an infection while carrying protective concentrations of 2G4/5D2 mAb. This finding demonstrates AAV6.2FF-mAb vaccines could be regularly used without fear of suppressing the endogenous immune system and could also be used in combination with conventional vaccines.

Hyperglobulinemia is a related potential side effect of AAV6.2FF-mAb therapies that has been raised. It is difficult to find a clinical definition for IgG-related hyperglobulinemia as the condition is generally related to IgD and IgE [64, 65]. A normal IgG concentration for a mouse is 2-5 mg/mL [66]. AAV6.2FF-MR191 expression was protective at less than 100 ug/mL. Assuming, conservatively, 2 mg/mL of murine IgG in the blood of mice, AAV6.2FF-mediated MR191 expression accounted for less than 5% of the total IgG. ZMapp™ was dosed at 50 mg/kg over multi-day treatment courses in humans to maintain a therapeutic threshold, however lower but more consistent mAb levels mediated by AAV6.2FF, would be able to maintain therapeutic efficacy without the peak and trough pharmacokinetics associated with repeat recombinant mAb administration.

There is strong evidence of the prophylactic efficacy of AAV6.2FF-mAb therapies, however post exposure use extends the potential applications of this therapy. Potential exposure to Ebola virus in a lab accident or health care setting are realistic possibilities that would require post-exposure interventions. For therapeutic use, AAV6.2FF-mAbs could be combined with an initial bolus of recombinant antibodies to extend the therapeutic window while also providing immediate intervention. Ebola virus is an aggressive infection and even partial group survival at a 100×LD50 challenge dose is promising because there is very little time for antibody production. With respect to less virulent virus such as influenza or respiratory syncytial virus (RSV) that does not cause fatality quickly, the chances of post-exposure prophylaxis is much higher. Thus, therapeutic applications of AAV6.2FF-mAbs, include post-exposure AAV6.2FF-mAbs treatment, for less virulent pathogens such as influenza or RSV.

Expansion of the AAV6.2FF-mAb platform to express the Marburg virus mAb, MR191, demonstrates the flexibility of this technology for applications beyond Ebola virus. The development of vaccines and other therapeutics to combat Ebola virus has become much more popular since the 2014-2016 West Africa outbreak.

The potential to re-administer AAV6.2FF vectors intramuscularly makes this platform a viable option for routine use. Re-administration of AAV6.2FF was successfully carried out in the present disclosure using luciferase vectors, and this experiment matched primary and secondary doses and were completed over 200 days apart. The follow up experiment in which homologous AAV6.2FF vectors were used to express heterologous mAbs was not successful in generating mAbs against both EBOV and MARV GPs. However, the secondary vector in this experiment was given at a lower dose than the primary injection ($3\times10^{10}$ vg vs $6 \times 10^{11}$ vg), without wishing to be bound by theory, the dose may be too low to overcome anti-AAV6.2FF capsid antibodies that may still be present since the secondary dose was administered only 70 days following primary vector, as opposed to 200 days in the AAV-luciferase re-administration experiment. Without wishing to be bound by theory, it is also possible that the secondary vector generated a boosted a primary response against either the AAV6.2FF capsid or the human IgG constant region, hindering expression of mAb 100. Without wishing to be bound by theory, the spike in antibody titers against mAb 100 may be the reason the re-administration experiment was not successful this time compared to the luciferase re-administration.

Antibodies against AAV6.2FF were detected in day 70 (pre-secondary injection) samples, however the reciprocal titers were greater following the secondary injection, without wishing to be bound by theory, suggesting a boosted response against the vector. The antibody response to the human IgG was low until day 70 and were drastically increased in post-secondary administration serum samples, without wishing to be bound by theory, which also suggests a boosted response against the human Fc domain of the IgG since the mAb variable regions were heterologous. Although a humoral response was detected against both the capsid and mAb 100, without wishing to be bound by theory, it is possible that the response directed against the human IgG was more damaging than the anti-capsid antibodies, which is consistent with the ability to re-administer the AAV6.2FF-luciferase vector IM.

In short, the boost dose shown in FIGS. 27A-27D was lower than the initial dose and a strong immune response against the Fc domain of the second human IgG might have obstructed the effects of re-administration. In contrast, as noted above, re-administration with luciferase was successful, and it was a less immunogenic transgene and the primary and secondary doses were matched (FIG. 26B), pointing to successful re-administration following certain matrix.

The low vector doses at which the inventors were able to confer 100% survival in mice demonstrates that relatively low yet sustained serum mAb concentrations are protective and this provides confidence in terms of scaling these AAV6.2FF-mAb vectors for use in larger animal models and eventually humans. Neutralizing antibody expression for over 400 days could realistically offer protection during a filovirus outbreak as they tend to be contained in less time but would offer locals and foreign health care workers an extra layer of protection in addition to a conventional vaccine.

Example 4

AAV-Sftpb Gene Therapy Rescues Respiratory Distress and Improves Survival in a Mouse Model of Surfactant Protein B Deficiency The AAV6.2FF platform described herein is a useful platform for delivering a "payload" such as a protein for treating genetic diseases, for example, genetic diseases in which the lung tissue is the target site of treatment modality. Pulmonary surfactant is a mixture of phospholipids and proteins (surfactant protein A (SPA), surfactant protein B (SPB), surfactant protein C (SPC) and surfactant protein D (SPD)) that reduces surface tension in the lung and allows normal breathing to occur. Without surfactant, alveoli collapse following exhalation. Surfactant is produced by alveolar type 2 (AT2) cells in the lung. A number of genetic disorders affects surfactant production. Currently, a lack of treatment options exists to treat the most severe genetic causes of surfactant deficiency, i.e. SPB Deficiency (Surfactant metabolism dysfunction, pulmonary, 1; MIM 265120), an autosomal recessive disease. Mutations to the SFTPB gene leads to production of mutated SPB protein that causes respiratory insufficiency resulting in death within months of birth. Treatment with exogenous surfactant is short-lived and the only available cure is lung transplantation. Most common mutation of SFTPB (121 ins2) occurs in 1:1000 individuals. ~10% of full term infants with unexplained respiratory failure have mutations in their SFTPB gene. The present inventors show AAV6.2FF-SPB rescues respiratory distress and increases survival in inducible SPB deficient (Sftpb−/−) mice.

Materials and Methods

AAV Plasmid Generation

All AAV genome plasmids were generated using a CASI promoter with a woodchuck hepatitis virus posttranscriptional regulatory element (WPRE) and SV40 polyA sequence downstream of the transgene with flanking AAV2 inverted terminal repeats (ITRs) [39] The murine SPB sequence was synthesized (GeneArt) after codon optimization for murine expression.

A second murine SPB construct was generated to express an additional HA epitope tag at the C-terminus of the mature peptide using the following primers to complete site-directed mutagenesis:

```
Forward:
                                   (SEQ ID NO: 39)
TACCCATACGATGTTCCAGATTACGCTAGATGCTCTACCGAGGA
CGC, Reverse:
                                   (SEQ ID NO: 40)
AGCGTAATCTGGAACATCGTATGGGTACAGCACCAGGCCACAC
ACGAGC.
```

AAV Vectors Generation

AAV6.2FF vectors were generated by the methods described herein. The AAV6.2FF-SPB vector used for the high dose survival experiments was manufactured at the Muscular Dystrophy Cooperative Research Center vector core and the AAV8-luciferase vector was generated by the University of Pennsylvania vector core. Vector genomes were quantified by taqman qPCR assay as previously described [45].

Transient Transfection of Expression Plasmids

Human embryonic kidney 293 cells (HEK293) (ATCC® CRL-1573) and murine lung epithelial 12 cells (MLE12) (ATCC® CRL-2110) were maintained in high glucose DMEM (HyClone SH30022.01) with 10% cosmic calf serum (HyClone SH30087), 2 mM L-glutamine (HyClone SH3003401), and 1% pen-strep (HyClone SV30010) and DMEM/F12 1:1 media including HEPES (HyClone SH30261) with the addition of 2% fetal bovine serum (HyClone SH30088), insulin (0.005 mg/mL)-transferrin (0.01 mg/mL)-selenium 30 nM (Gibco 41400045), 10 nM hydrocortisone (Sigma H6909), 10 nM Beta-estradiol (Sigma E2758), 2 mM L-glutamine (HyClone SH3003401), and 1% pen-strep (HyClone SV30010), respectively.

At 75% confluency, HEK293 cells were transfected with linear polyethylenimine MW 25,000, while lipofectamine was used for MLE12 cells. Cell lysates were harvested using RIPA buffer (50 mM Tris pH 7.5, 150 mM NaCl, 1% Triton X-100, 0.1% SDS, 10 mM EDTA, 1% sodium deoxycholate) containing Na3VO4 (1 mmol/L), NaF (50 mM) and protease inhibitors (Sigma), 48 hours post transfection and prepared for immunoblotting using a 4×SDS-PAGE reducing buffer. AAV-SPB was incubated with HEK293 cells at a multiplicity of infection (MOI) of 20,000 and cell lysates were harvested 72 hours later and similarly prepared for immunoblotting.

Immunoblotting

Cell lysates were separated on a 10% tris-glycine polyacrylamide gel and transferred to a PDVF membrane at 100V for 1 hour. The membrane was blocked in 5% bovine serum albumin with PBS plus 1% tween 20 (PBS-T) for 1 hour with rotation and washed three times with PBS-T. Primary antibodies were incubated overnight 4° C. at a 1:2,000 dilution (Cell Signaling D84C12 and C29F4) and washed three times with PBS-T before addition of anti-rabbit HRP at a 1:4,000 dilution (Life Sciences 1571722). Membranes were washed twice with PBS-T, once with PBS and imaged using HRP substrate (Luminata WBLUF0100) in a BioRad Chemidock.

Animals

All procedures involving animals were approved by the Animal Care and Veterinary Service Committee (ACVS) at the University of Ottawa. The SPB-deficiency model has been described previously [67]. In this model, SPB expression was sustained by doxycycline, for instance, in animal feed, whereas SPB-deficiency (i.e. SPB knockout) was induced by the removal of doxycycline, i.e. when doxycycline supplemented feed was replaced with regular chow diet (see below under "Doxycycline Feed").

Intratracheal (IT) Injections

One hour before surgery, animals were injected subcutaneously (sc) with 0.05 mg/kg buprenorphine. For IT injections, animals were individually anesthetized with isofluorane and injected sc with 1 mL of sterile saline solution and the fur in the tracheal region was shaved to the skin. A tracheotomy was performed under constant isofluorane anesthesia, and mice received a single IT injection of AAV vector. Different titers of AAV vector ($10^{10}$ viral genomes (vg); $10^{11}$ vg; or $5*10^{11}$ vg) was diluted to a total volume of 50-75 µL with 1×PBS. Injections were carried out using a 3/10 mL insulin syringe 29 gauge×½" (Covidien). Openings were sutured and topical bupivacaine was applied at the surgical site. Mice recovered in a 37° C. incubator for 1 hr.

In Vivo Imaging System (IVIS) and Diffuse Tomography (DLIT)

Mice were intratracheally injected with $10^{11}$ vg of AAV6.2FF-Luciferase. One week post injection In Vivo Imaging System (IVIS) and/or Diffuse Tomography (DLIT) was carried out. D-luciferin was sterilely prepared within 24 hr of injection at a concentration of 15 mg/mL in 1×PBS. Uninjected and AAV6.2FF-Luciferase mice were injected with 150 mg/kg of D-Luciferin 15-20 min before IVIS imaging. Up to 4 mice at a time were IVIS imaged, while DLIT was performed on individual mice. For DLIT imaging briefly, surface topography was generated, followed by 3D reconstruction of bioluminescence as per the manufacturer's instructions (PerkinElmer). All DLIT images were performed within 30-45 min of D-Luciferin injection.

Doxycycline Feed

Mice were maintained on doxycycline supplemented feed (0.625 g/kg doxycycline hyclate; Teklad). For structure/function and survival studies doxycycline feed was replaced with regular chow diet. The removal of doxycycline induces Sftpb knockout. Typically, mice were maintained on doxycycline feed for 4 weeks post-AAV administration. Mice were weighed before and after doxycycline removal. For survival studies mice were monitored at least 2 times/day following doxycycline removal. If mice displayed signs of respiratory distress and weight loss occurred, monitoring took place every 2-3 hours. Withdrawal of doxycycline may lead to death within 3 days.

Lung Function Analysis

Mice were euthanized with an intraperitoneal (IP) injection of euthanyl. Immediately following euthanasia (within 10-15 min) pressure-volume curves were obtained using a small animal mechanical ventilator (flexiVent, Scireq). Briefly, euthanized animals had an 18-gauge cannula attached to the flexiVent secured to their trachea. The lungs were inflated with regular increasing intervals of pressure to a maximum of 30 cm $H_2O$. Lungs were subsequently deflated with lung volumes recorded at each decreasing interval of pressure to obtain pressure-volume curves. All data was obtained using FlexiWare software. Pressure-volume curves were normalized to the body weight of each animal. %V10, total lung volume, residual volume and lung compliance were extracted from the pressure-volume curves.

Lung Histology

Macroscopic lung images were obtained with an iPhone 6S camera (Apple). The left lungs were perfused with 4% paraformaldehyde (4% PFA) and fixed for 2 days. On day 3, the 4% PFA was removed and replaced with 70% ethanol. The left lungs were embedded in paraffin and cut coronally to obtain longitudinal 4 µm sections of the lung. Serial sections were stained with hematoxylin and eosin (H&E) or Wright-Giemsa Jenner (WGJ) stains. Scanned images were obtained at 20× with the Aperio CS2 digital brightfield scanner (Leica), and at 20× and 40× with the Leica DM4000 upright brightfield microscope.

Immunofluorescence

All immunofluorescence images were obtained from OCT-frozen right lung sections. All sections were cut into 6-8 µm sections using the Leica CM1860 cryostat. Sections were air-dried for 3 h at room temperature (RT) and stored at −20° C. Prior to fixing and staining, frozen sections were thawed at 37° C. for 2-3 h. Briefly, sections were fixed in −20° C. acetone for 15 min and washed with 0.1% Tween-20/1×PBS two times (5 min/wash) and 1×PBS once (5 min). Antigen retrieval using 10 mM sodium citrate pH6.0 solution with 0.05% Tween-20 heated to boiling was carried out three times (10 min/incubation). Slides were cooled to RT in 1×PBS. The sections were permeabilized in 0.1% Triton X-100/1×PBS for 10 min at RT and blocked in 10% FBS/1×PBS for 1 hr at RT. Sections were stained for Pro-SPC (rabbit Pro-SPC; Millipore) or SPB (rabbit anti-SPB; Seven Hills) for 2-3 days at 4° C. in a light-resistant slide box. Washing was with 1×PBS three times (5 min/wash) and coverslips were mounted on sections with Fluoroshield with DAPI (Sigma). 20× images were obtained with an epifluorescence microscope (Zeiss Axio Imager.M2).

Transmission Electron Microscopy

Sections of the right lung lobe (2 mm×2 mm×2 mm) were immersed in 2.5% glutaraldehyde (pH 7.3) in 0.05% sodium cacodylate. Tissue sections were fixed in 2% osmium tetroxide and dehydrated in ethanol. Tissue sections were incubated in acetone before embedding in resin. Sections were stained with the double contrast method of uranyl acetate and lead citrate and digitally imaged with the Hitachi H7100 transmission electron microscope.

Intubation Injections

Mice were anesthetized with ketamine and xylazine and placed on a stand (Harvard Apparatus) with the upper incisors hooked onto a thread. A flexible optic fiber attached to a light source at one end was placed into a 22-gauge cannula. The mice were intubated using the light from the optic fiber cable as a guide to insert the cannula into the trachea. Mice received a single injection of AAV vector at $10^{11}$ vg/mouse diluted to a total volume of 50 µL with 1×PBS. Injections were with a 1 mL Tuberculin Slip Tip syringe (BD). Mice recovered in a 37° C. incubator for 1 hr.

Pulmonary Surfactant to Improve Distribution of AAV Vector

Bovine Lipid Extract Surfactant (BLES; BLES Biochemicals Inc) was administered by intratracheal injection at a concentration of 0.54 mg phospholipids in a volume of 65 µL. BLES was given by intubation at a concentration of 1.21 mg phospholipids in a volume of 50 µL.

Results and Discussion

Figure 28A:
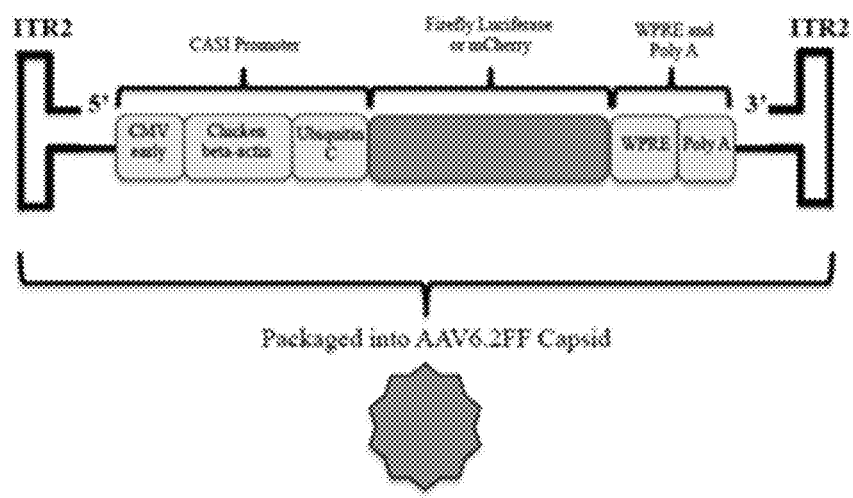
FIGS. 28A-28I show AAV6.2FF capsid coat targets alveolar epithelial type 2 (AT2) cells in the lung tissue and expresses SPB protein in vitro.
Figure 28B:
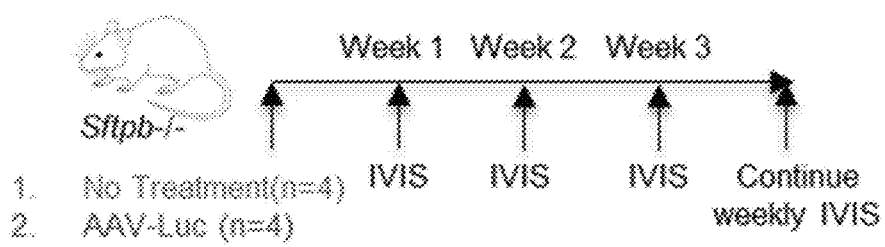
Figure 28C:
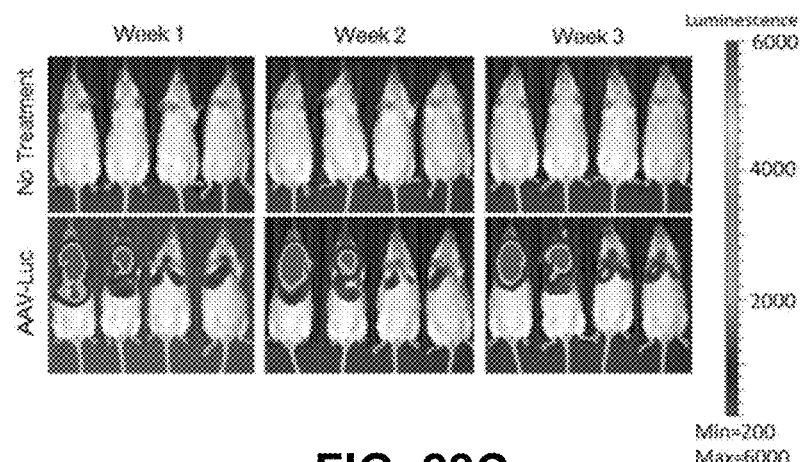
Figure 28D:
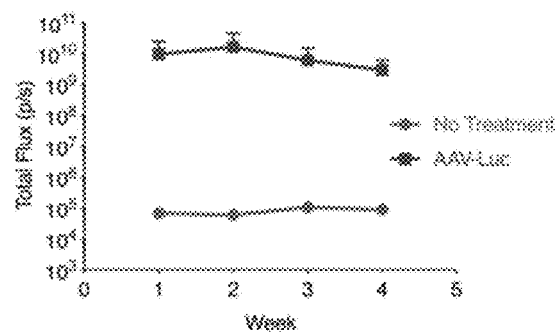
Figure 28E:
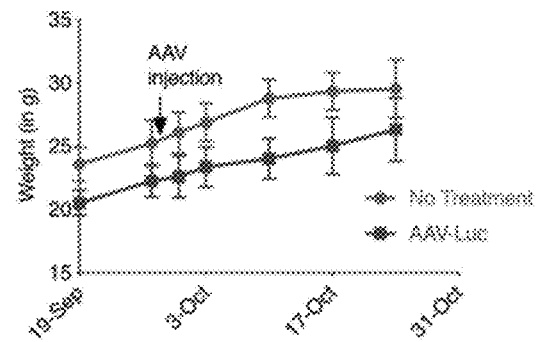
Figure 28F:
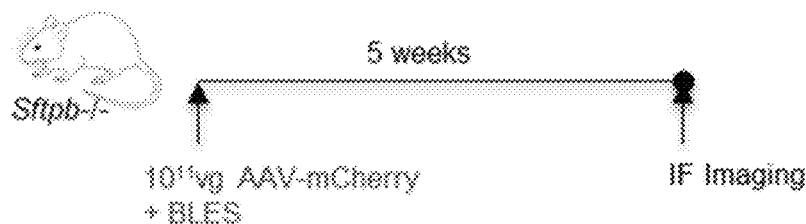
Figure 28G:
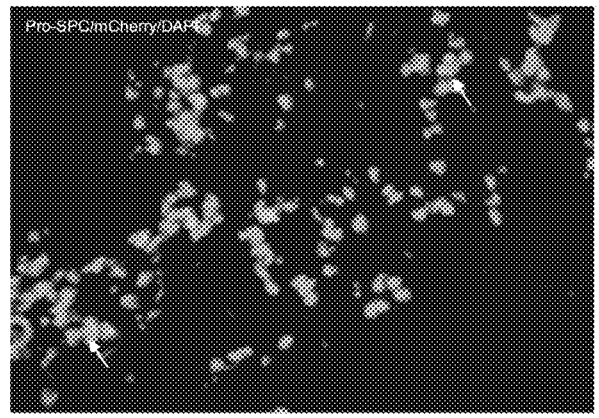

The schematic of AAV6.2FF vectors expressing Luciferase or -mCherry reporter genes is shown in FIG. 28A. These AAV vectors were injected intratracheally into Stpb−/− mice (i.e. SPB deficient mice) and they are shown to target the lung (Luciferase; FIGS. 28B-28D), and particularly alveolar epithelial type 2 (AT2) cells in lung tissue (mCherry; FIGS. 28F-28G). As shown in FIG. 28E, both AAV-Luciferase treated mice and untreated mice gained weight consistently.

Figure 28H:
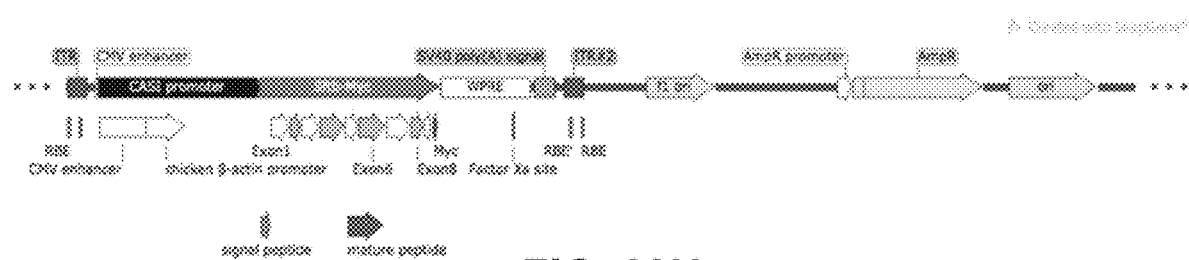
Figure 28I:
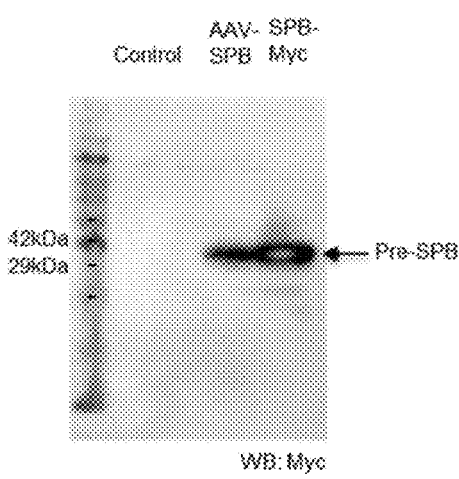

Inventors then generated AAV6.2FF-SPB by inserting codon optimized murine SPB cDNA (encoding a C-terminal myc-tag SPB protein) into expression vector of the present invention (FIG. 28H). Western blotting of HEK293 cells transduced with AAV6.2FF-SPB confirms expression of SPB protein (FIG. 28I).

Figure 29A:
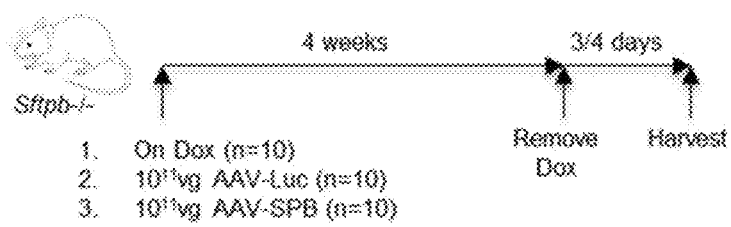
FIGS. 29A-29L show AAV6.2FF-SPB treatment increases SPB expression, maintains normal alveolar epithelial type 2 (AT2) cell structure, and improves lung function in a SPB deficient mouse model.
Figure 29B:
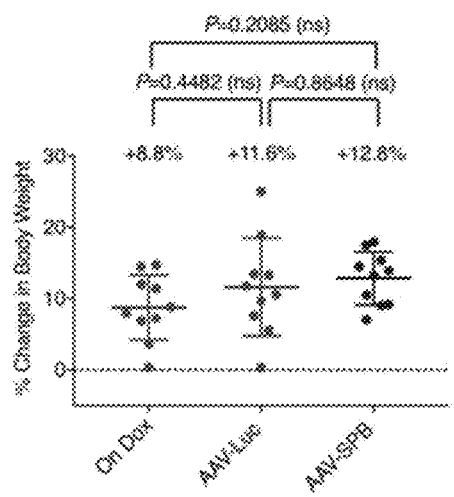
Figure 29C:
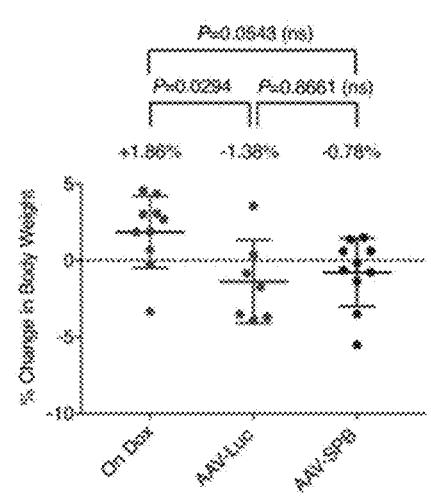
Figure 29D:
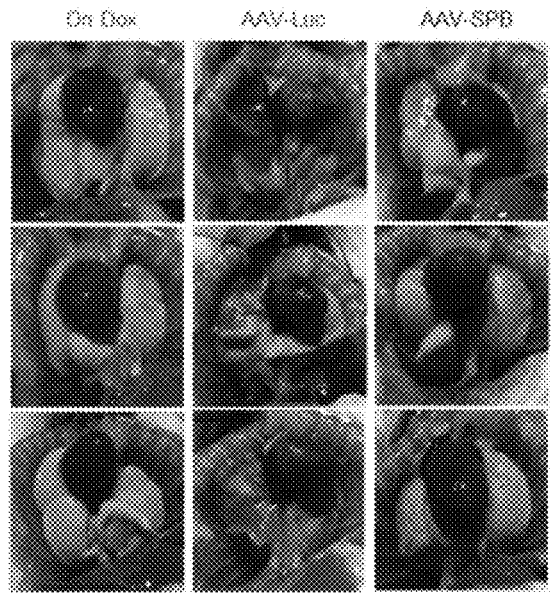
Figure 29E:
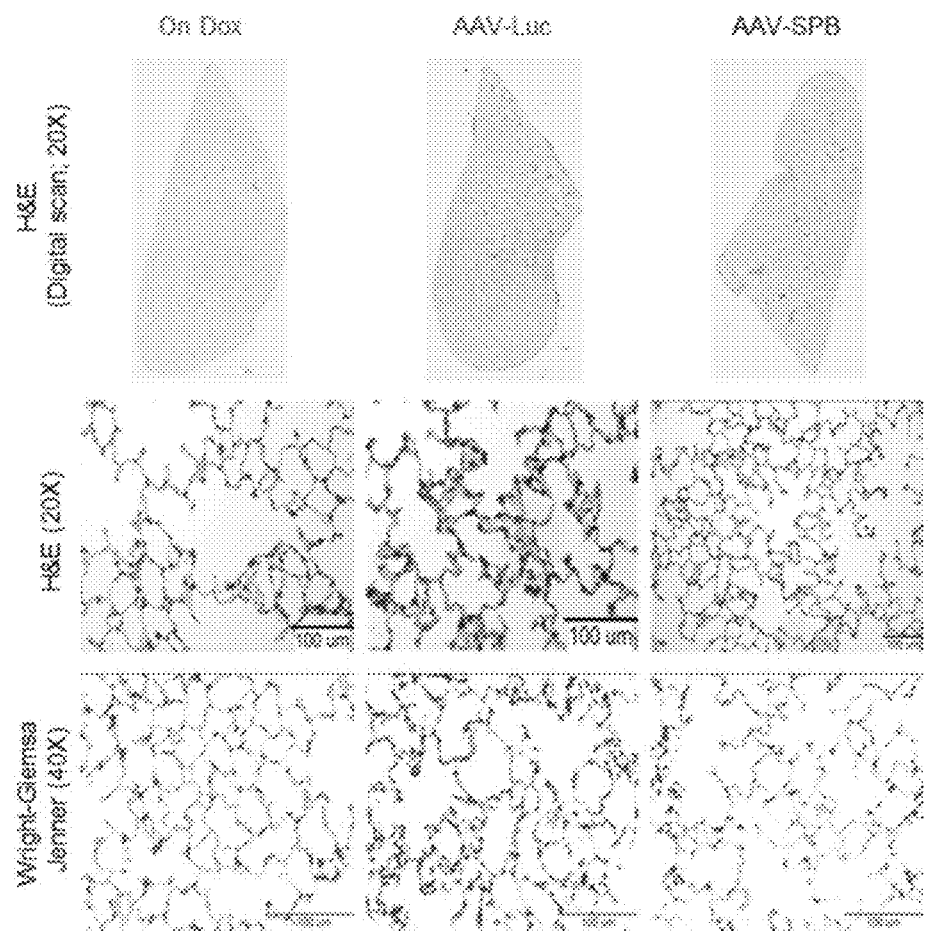
Figure 29F:
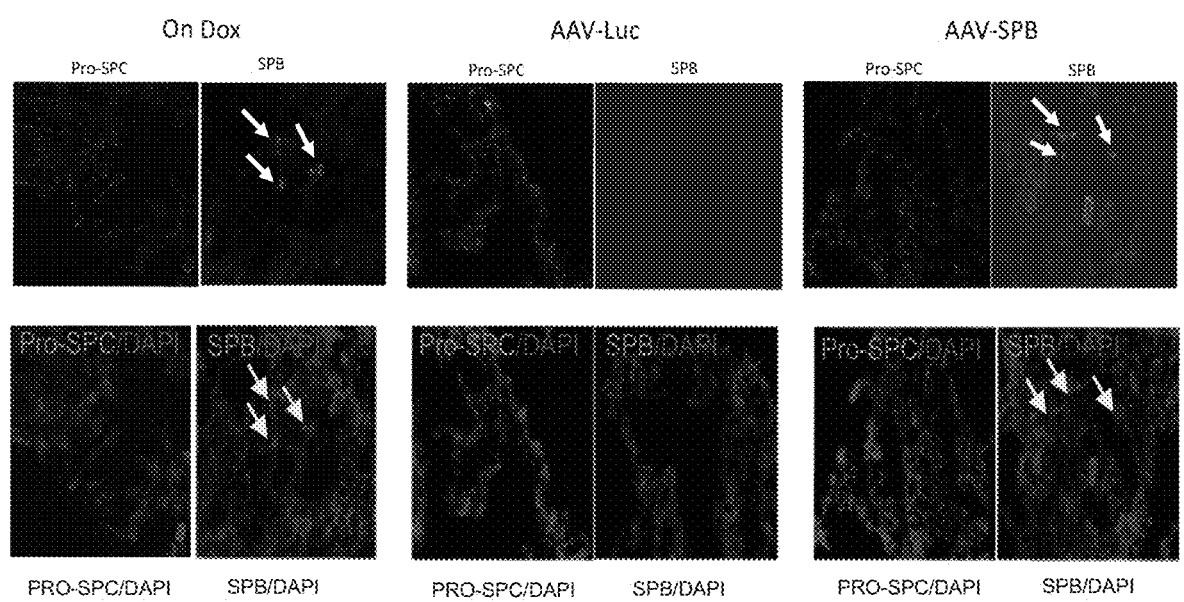
Figure 29G:
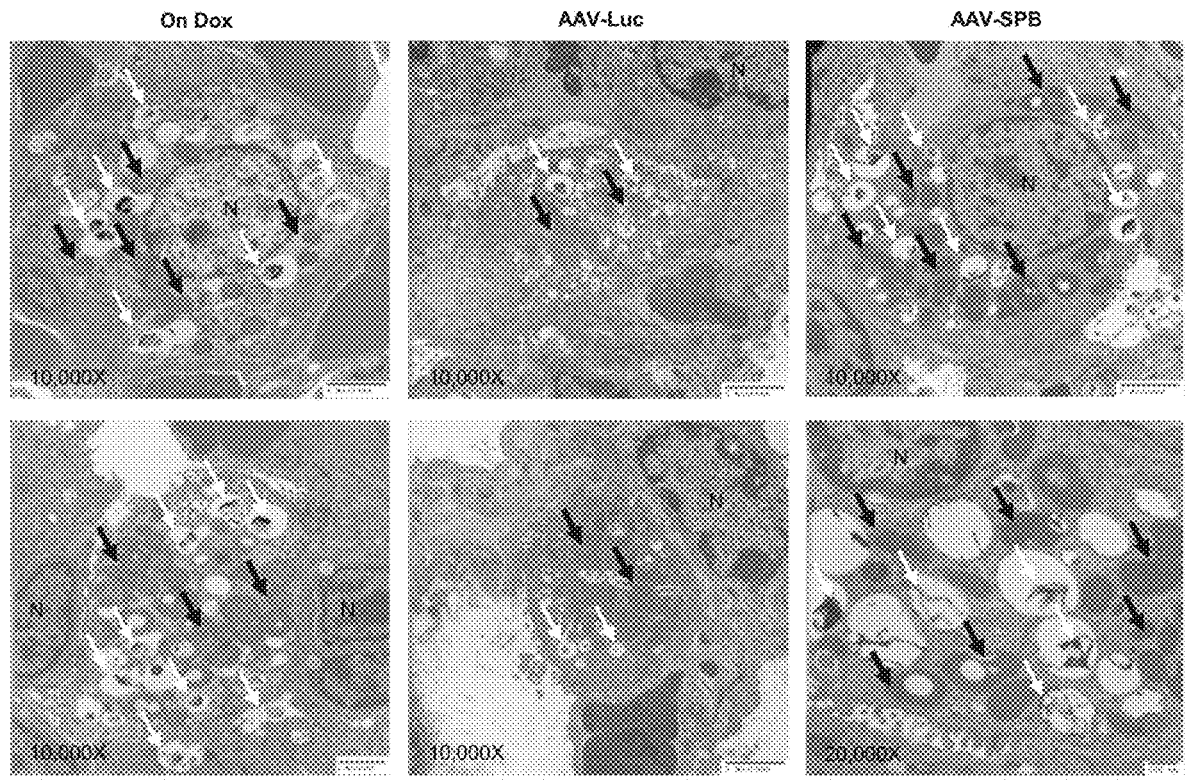
Figure 29H:
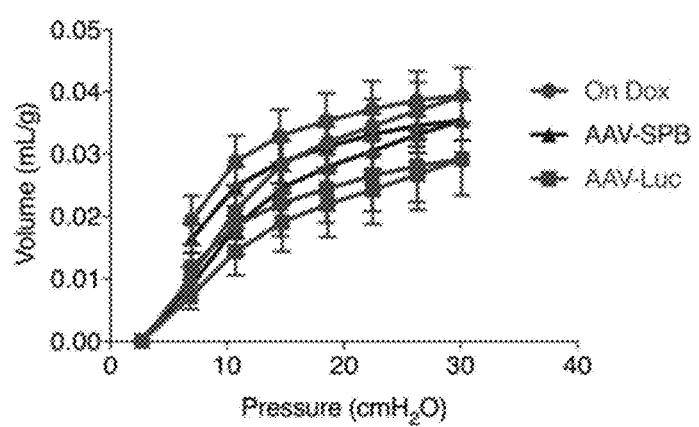
Figure 29I:
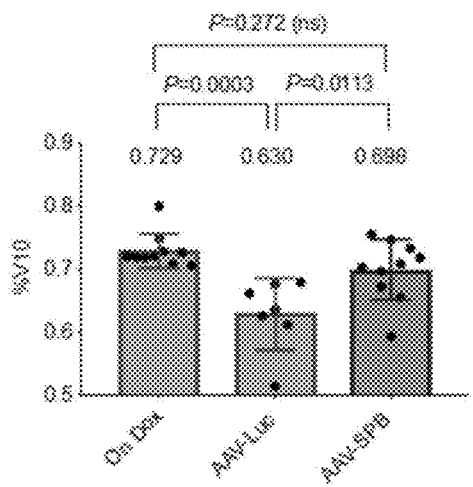
Figure 29J:
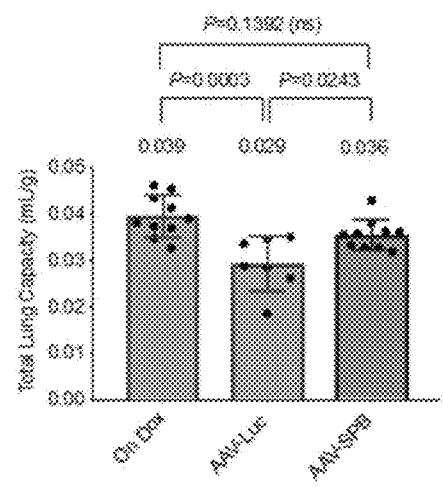
Figure 29K:
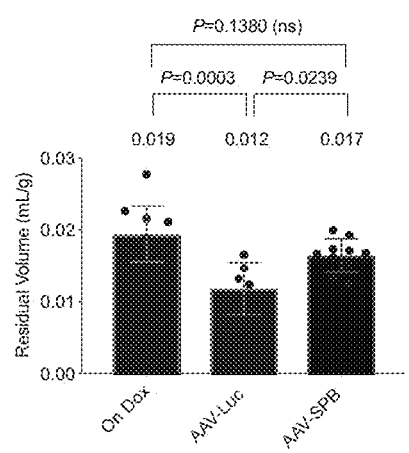
Figure 29L:
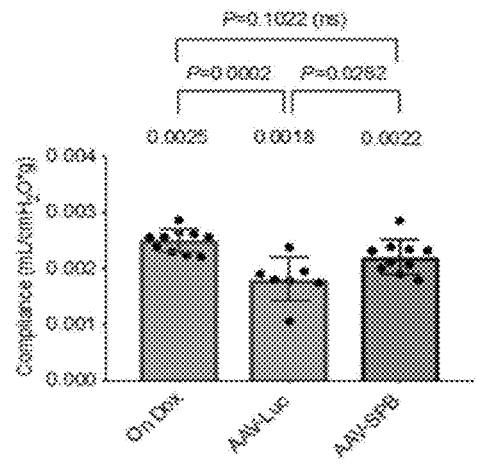

Inventors then showed that AAV6.2FF-SPB treatment in SPB deficient mice increased SPB expression in lung tissue, maintained normal AT2 cell structure, and improved lung function, as compared to negative control (AAV6.2FF-Luciferase; FIGS. 29A-29L). Study design schematic is shown in FIG. 29A. There was no significant changes in body weight following AAV injection or following doxycycline removal (FIGS. 29B and 29C). Macroscopic lung images 3 to 4 days following doxycycline removal (i.e. induction of SPB deficiency) is shown in FIG. 29D. H&E staining of whole left lungs after doxycycline removal is shown in FIG. 29E. Epifluorescence images of Pro-SPC, DAPI and SPB from OCT frozen right lung sections following doxycycline removal is shown in FIG. 29F, where arrows indicate SPB staining. TEM images of two different fields of view of AT2 cells following doxycycline removal are shown in FIG. 29G, where white arrows indicate lamellar bodies and black arrows indicate mitochondria. Pressure Volume Curve following doxycycline removal corrected for body weight in shown in FIG. 29H. % V10, total lung volume, residual volume and lung compliance were extracted from the pressure-volume curves (FIGS. 29I-29L). These parameters all showed that AAV6.2FF-SPB treatment maintains lung functions in SPB deficient mice similar to mice that were kept on doxycycline feed (i.e. non-SPB deficient mice).

Figure 30:
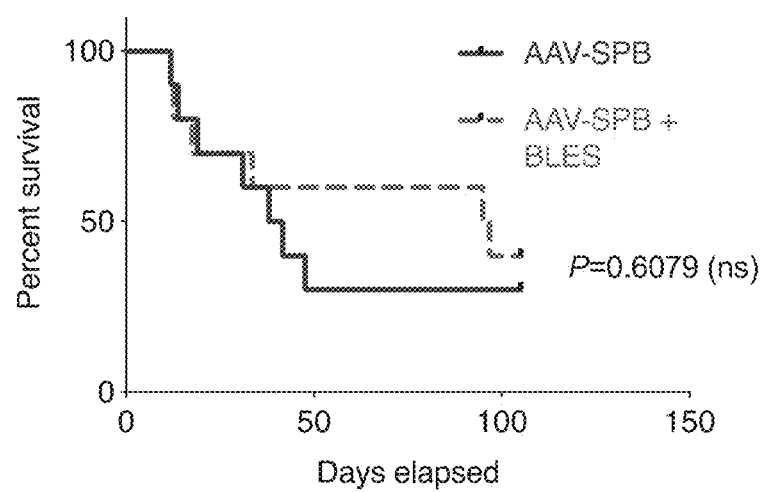
FIG. 30 shows improved median survival with Bovine Lipid Extract Surfactant (BLES) and endotracheal tube (intubation) delivery of 10$^{11}$ vg/mouse (intermediate dose) AAV6.2FF-SPB into SPB deficient mice. Kaplan-Meier survival curve of 10$^{11}$ vg/mouse (intermediate dose)±BLES treatment delivered into intubated mice. Survival curve P values=Log-rank, Mantel-Cox test; ns=not significant.

A comparison is made between the effects of intubated delivery of AAV-SPB alone and AAV-SPB with Bovine Lipid Extract Surfactant (BLES) in SPB deficient mice. FIG. 30 shows improved median survival with BLES and endotracheal tube (intubation) delivery of $10^{11}$ vg/mouse (intermediate dose) AAV6.2FF-SPB into SPB deficient mice, albeit the improvement is not significant.

Together, these results show that AAV6.2FF-SPB targets lung tissue and expresses SPB protein in the lung tissue, in particular AT2 cells in the lung tissue. As such, AAV6.2FF is a useful platform for treating genetic diseases, and specifically, AAV6.2FF-SPB gene therapy is a useful strategy in treating genetic disorders of SPB deficiency. Thus, AAV6.2FF may also be a platform for treating diseases involving lung tissues.

While the present disclosure has been described with reference to what are presently considered to be the preferred example, it is to be understood that the disclosure is not limited to the disclosed example. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Zincarelli, C., Soltys, S., Rengo, G., Rabinowitz, J. E. Analysis of AAV Serotypes 1-9 Mediated Gene Expression and Tropism in Mice After Systemic Injection. Mol Ther. 2008; 16(6):1073-1080.
2. Ellis, B. L., Hirsch, M. L., Barker, J. C., Connelly, J. P., Steininger, R. J., and Porteus, M. H. A survey of ex vivo/in vitro transduction efficiency of mammalian primary cells and cell lines with Nine natural adeno-associated virus (AAV1-9) and one engineered adeno-associated virus serotype. Virol J. 2013; 10(74):1-10.
3. Grimm, D., Lee, J. S., Wang, L., Desai, T., Akachem B., Storm, T. A. and Kay, M. A. In Vitro and In Vivo Gene Therapy Vector Evolution via Multispecies Interbreeding and Retargeting of Adeno-Associated Viruses. J Virol. 2008; 82(12):5887-5911.
4. Lerch, T. F., O'Donnell, J. K., Meyer, N. L., Xie, Q., Taylor, K. A., Stagg, S. M., and Chapman, M. S. Structure of AAV-D J, a Retargeted Gene Therapy Vector. Cryo-Electron Microscopy at 4.5 Å resolution. Structure. 2012; 20(8):1310-1320.
5. Limberis, M. P., Vandenberghe, L. H., Zhang, L., Pickles, R. J., and Wilson, J. M. Transduction Efficiencies of Novel AAV Vectors in Mouse Airway Epithelium In Vivo and Human Ciliated Airway Epithelium In Vitro. Mol Ther. 2009; 17(2):294-301.
6. Vandenberghe, L. H., Breous, E., Nam, H., Goa, G., Xiao, R., Sandhu, A., Johnston, J., Debyser, Z., Agbandje-McJenna, M., and Wilson, J. Naturally occurring singleton residues in AAV capsid impact vector performance and illustrate structural constraints. Gene Ther. 2009; 16(12):1416-1428.
7. Yan, Z., Zak, R., Luxton, G. W. G., Ritchie, T. C., Bantel-Schaal, U., and Engelhardt, J. F. Ubiquitination of both Adeno-Associated Virus Type 2 and 5 Capsid Proteins Affects the Transduction Efficiency of Recombinant Vectors. J Virol. 2002; 76(5):2043-2053.
8. Zhong, L., Li, B., Jayandharana, G., Mah, C. S., Govindasamy, L., Agbandje-McKenna, M., Herzog, R. W., Weigel-Van Aken, K. A., Hobbs, J. A., Zolotukhin, S., Muzyczka, N., and Srivastava, A. Tyrosine phosphorylation of AAV2 vectors and its consequences on viral intracellular trafficking and transgene expression. Virology. 2008; 381(2):194-202.
9. Zhong, L., Li, B., Mah, C. S., Govindasamy, L., Agbandje-McKenna, M., Cooper, M., Herzog, R. W., Zolotukhin, I., Warrington, K. H. Jr., Weigel-Van Aken, K. A., Hobbs, J. A., Zolotukhin, S., Muzyczka, N., and Srivastava, A. Next generation of adeno-associated virus 2 vectors: Point mutations in tyrosines lead to high-efficiency transduction at lower doses. PNAS. 2008; 105 (22): 7827-7832.
10. Markusic, D. M., Herzog, R. W., Aslanidi, G. V., Hoffman, B. E., Li, B., Li, M., Jayandharan, G. R., Ling, C., Zolotukhin, I., Ma, W., Zolotukhin, S., Srivastava, A., and Zhong, L. High-efficiency transduction and correction of murine hemophilia B using AAV2 vectors devoid of multiple surface-exposed tyrosines. Mol Ther. 2010; 18(12):2048-2056.
11. Qiao, C., Zhang, W., Yuan, Z., Shin, J. H., Li, J., Jayandharan, G. R., Zhong, L., Srivastava, A., Xiao, X., and Duan, D. Adeno-Associated Virus Serotype 6 Capsid Tyrosine-to-Phenylalanine Mutations Improve Gene Transfer to Skeletal Muscle. Hum Gene Ther. 2010; 21(10):1343-1348.
12. Wu, Z., Asokan, A., Grieger, J. C., Govindasamy, L., Agbandje-Mckenna, M., and Samulski, R. J. Single Amino Acid Changes Can Influence Titer, Heparin Binding, and Tissue Tropism in Different Adeno-Associated Virus Serotypes. J Virology. 2006; 80(22):11393-11397.
13. Mingozzi, F. and High, K. A. Immune responses to AAV vectors: overcoming barriers to successful gene therapy. Blood. 2013; 122(1):23-36.
14. Ng, R., Govindasamy, L., Gurda, B. L., McKenna, R., Kozyreva, O. G., Samulski, R. J., Parent, K. N., Baker, T. S., and Agbandje-McKenna, M. Structural Characterization of the Dual Glycan Binding Adeno-Associated Virus Serotype 6. J Virology. 2010; 84: 12945-12957.
14b. Neves, H. and Kowk, H. F. Recent advances in the field of anti-cancer immunotherapy. BBA clinical 2015; 3:280-288.
15. Yu, D. L., Linnerth-Petrik, N. M., Halbert, C. L., Walsh, S. R., Miller, A. D., and Wootton, S. K. Jaagsiekte Sheep Retrovirus and Enzootic Nasal Tumor Virus Promoters Drive Gene Expression in All Airway Epithelial Cells of Mice but Only Induce Tumors in the Alveolar Region of the Lungs. J Virol. 2011; 85(15):7535-7545.
16. Santry, L. A., Ingrao, J. C., Yu, D. L., de Jong, J. G., van Lieshout, L. P., Wood, G. A., and Wootton, S. K. AAV vector distribution in the mouse respiratory tract following four different methods of administration. BMC Biotech. 2017; 17(43):1-11.
17. Spengler, J. R., Ervin, E. D., Towner, J. S., Rollin, P. E., andNichol, S. T. Perspectives on West Africa Ebola Virus Disease Outbreak, 2013-2016. Emerg Infect Dis. 2016; 22, 956-963.
18. Sparrow, E., Friede, M., Sheikh, M., and Torvaldsen, S. Therapeutic antibodies for infectious diseases. Bull World Health Organ. 2017; 95(3), 235-237.
19. Qiu, X., and Kobinger, G. P. Antibody therapy for Ebola: Is the tide turning around? Hum Vaccin Immunother. 2014; 10, 964-967.
20. Mupapa, K., Massamba, M., Kibadi, K., Kuvula, K., Bwaka, A., Kipasa, M., Colebunders, R., and Muyembe-Tamfum, J. J. Treatment of Ebola hemorrhagic fever with blood transfusions from convalescent patients. International Scientific and Technical Committee. J Infect Dis. 1999; 179 Suppl 1, S18-23.
21. Qiu, X., Wong, G., Fernando, L., Audet, J., Bello, A., Strong, J., Alimonti, J. B., and Kobinger, G. P. mAbs and Ad-Vectored IFN-alpha therapy rescue ebola-infected nonhuman primates when administered after the detection of viremia and symptoms. Sci Transl Med. 2013; 5(207), 207ra143.
22. Dye, J. M., Herbert, A. S., Kuehne, A. I., Barth, J. F., Muhammad, M. A., Zak, S. E., Ortiz, R. A., Prugar, L. I., and Pratt, W. D. Postexposure antibody prophylaxis protects nonhuman primates from filovirus disease. Proc Natl Acad Sci USA. 2012; 109(13), 5034-5039.
23. Pettitt, J., Zeitlin, L., Kim, D. H., Working, C., Johnson, J. C., Bohorov, O., Bratcher, B., Hiatt, E., Hume, S. D., Johnson, A. K., Morton, J., Pauly, M. H., Whaley, K. J., Ingram, M. F., Zovanyi, A., Heinrich, M., Piper, A., Zelko, J., and Olinger, G. G. Therapeutic intervention of Ebola virus infection in rhesus macaques with the MB-003 monoclonal antibody cocktail. Sci Transl Med. 2013; 5(199), 199ra13.
24. Qiu, X., Audet, J., Wong, G., Pillet, S., Bello, A., Cabral, T., Strong, J. E., Plummer, F., Corbett, C. R., Alimonti, J. B., Kobinger, G. P. Successful treatment of ebola virus-infected cynomolgus macaques with monoclonal antibodies. Sci Transl Med. 2012; 4(138), 138ra81.
25. Marzi, A., Yoshida, R., Miyamoto, H., Ishijima, M., Suzuki, Y., Higuchi, M., Matsuyama, Y., Igarashi, M., Nakayama, E., Kuroda, M., Saijo, M., Feldmann, F., Brining, D., Feldmann, H., and Takada, A. Protective efficacy of neutralizing monoclonal antibodies in a non-human primate model of Ebola hemorrhagic fever. PLoS One. 2012; 7(4), e36192.
26. Olinger, G. G. Jr., Pettitt, J., Kim, D., Working, C., Bohorov, O., Bratcher, B., Hiatt, E., Hume, S. D., Johnson, A. K., Morton, J., Pauly, M., Whaley, K. J., Lear, C. M., Biggins, J. E., Scully, C., Hensley, L., and Zeitlin, L. Delayed treatment of Ebola virus infection with plant-derived monoclonal antibodies provides protection in rhesus macaques. Proc Natl Acad Sci USA. 2012; 109 (44), 18030-18035.
27. Qiu, X., Wong, G., Fernando, L., Ennis, J., Turner, J. D., Alimonti, J. B., Yao, X., and Kobinger, G. P. Monoclonal antibodies combined with adenovirus-vectored interferon significantly extend the treatment window in Ebola virus-infected guinea pigs. J Virol. 2013; 87(13), 7754-7757.
28. Marzi, A., Engelmann, F., Feldmann, F., Haberthur, K., Shupert, W. L., Brining, D., Scott, D. P., Geisbert, T. W., Kawaoka, Y., Katze, M. G., Feldmann, H., and Messaoudi, I. Antibodies are necessary for rVSV/ZEBOV-GP-mediated protection against lethal Ebola virus challenge in nonhuman primates. Proc Natl Acad Sci USA. 2013; 110(5), 1893-1898.
29. Wong, G., Richardson, J. S., Pillet, S., Patel, A., Qiu, X., Alimonti, J., Hogan, J., Zhang, Y., Takada, A., Feldmann, H., and Kobinger, G. P. Immune parameters correlate with protection against ebola virus infection in rodents and nonhuman primates. Sci Transl Med. 2012; 4(158), 158ra146.
30. Qiu, X., Alimonti, J. B., Melito, P. L., Fernando, L., Strbher, U., and Jones, S. M. Characterization of Zaire ebolavirus glycoprotein-specific monoclonal antibodies. Clin Immunol. 2011; 141(2), 218-227.
31. Audet, J., Wong, G., Wang, H., Lu, G., Gao, G. F., Kobinger, G., and Qiu, X. Molecular characterization of the monoclonal antibodies composing ZMAb: a protective cocktail against Ebola virus. Sci Rep. 2014; 4, 6881.
32. Fauci, A. S. Ebola-underscoring the global disparities in health care resources. N Engl J Med. 2014; 371, 1084-1086.
33. Tran, E. E., Nelson, E. A., Bonagiri, P., Simmons, J. A., Shoemaker, C. J., Schmaljohn, C. S., Kobinger, G. P., Zeitlin, L., Subramaniam, S., and White, J. M. Mapping of Ebolavirus Neutralization by Monoclonal Antibodies in the ZMapp Cocktail Using Cryo-Electron Tomography and Studies of Cellular Entry. J Virol. 2016; 90, 7618-7627.

34. Qiu, X., Fernando, L., Melito, P. L., Audet, J., Feldmann, H., Kobinger, G., Alimonti, J. B., and Jones, S. M. Ebola G P-specific monoclonal antibodies protect mice and guinea pigs from lethal Ebola virus infection. PLoS Negl Trop Dis. 2012; 6, e1575.

35. Hessell, A. J., Hangartner, L., Hunter, M., Havenith, C. E., Beurskens, F. J., Bakker, J. M., Lanigan, C. M., Landucci, G., Forthal, D. N., Parren, P. W., Marx, P. A., and Burton, D. R. Fc receptor but not complement binding is important in antibody protection against HIV. Nature. 2007; 449(7158), 101-104.

36. Cadogan, M. and Dalgleish, A. G. HIV immunopathogenesis and strategies for intervention. Lancet Infect Dis. 2008; 8(11), 675-684.

37. Naso, M. F., Tomkowicz, B., Perry, W. L. 3$^{rd}$., and Strohl, W. R. Adeno-Associated Virus (AAV) as a Vector for Gene Therapy. BioDrugs. 2017; 31(4): 317-334.

38. Mingozzi, F. and High, K. A. Therapeutic in vivo gene transfer for genetic disease using AAV: progress and challenges. Nat Rev Genet. 2011; 12(5), 341-355.

39. Balazs, A. B., Chen, J., Hong, C. M., Rao, D. S., Yang, L., and Baltimore, D. Antibody-based protection against HIV infection by vectored immunoprophylaxis. Nature. 2011; 481(7379), 81-84.

40. Balazs, A. B., Ouyang, Y., Hong, C. M., Chen, J., Nguyen, S. M., Rao, D. S., An, D. S. and Baltimore, D. Vectored immunoprophylaxis protects humanized mice from mucosal HIV transmission. Nat Med. 2014; 20(3), 296-300.

41. Balazs, A. B., Bloom, J. D., Hong, C. M., Rao, D. S., and Baltimore, D. Broad protection against influenza infection by vectored immunoprophylaxis in mice. Nat Biotechnol. 2013; 31(7), 647-652.

42. Limberis, M. P., Adam, V. S., Wong, G., Gren, J., Kobasa, D., Ross, T. M., Kobinger, G. P., Tretiakova, A., and Wilson, J. M. Intranasal antibody gene transfer in mice and ferrets elicits broad protection against pandemic influenza. Sci Transl Med. 2013; 5(187), 187ra72.

43. Limberis, M. P., Tretiakova, A., Nambiar, K., Wong, G., Racine, T., Crosariol, M., Xiangguo, Q., Kobinger, G., and Wilson, J. M. Adeno-Associated Virus Serotype 9-Expressed ZMapp in Mice Confers Protection Against Systemic and Airway-Acquired Ebola Virus Infection. J Infect Dis. 2016; 214(12), 1975-1979.

44. Halbert, C., Allen, J. M., and Miller, A. D. Efficient mouse airway transduction following recombination between AAV vectors carrying parts of a larger gene. Nat Biotechnol. 2002; 20(7), 697-701.

45. Aurnhammer, C., Haase, M., Muether, N., Hausl, M., Rauschhuber, C., IHuber, I., Nitschko, H., Busch, U., Sing, A., Ehrhardt, A., and Baiker, A. Universal real-time PCR for the detection and quantification of adeno-associated virus serotype 2-derived inverted terminal repeat sequences. Hum Gene Ther Methods. 2012; 23(1), 18-28.

46. Hevey, M., Negley, D., Geisbert, J., Jahrling, P., and Schmaljohn, A. Antigenicity and vaccine potential of Marburg virus glycoprotein expressed by baculovirus recombinants. Virology. 1997; 239(1), 206-216.

47. Bray, M., Davis, K., Geisbert, T., Schmaljohn, C., and Huggins, J. A mouse model for evaluation of prophylaxis and therapy of Ebola hemorrhagic fever. J Infect Dis. 1998; 178(3), 651-661.

48. Limberis, M. P., Racine, T., Kobasa, D., Li, Y., Gao, G. F., Kobinger, G., and Wilson, J. M. Vectored expression of the broadly neutralizing antibody F16 in mouse airway provides partial protection against a new avian influenza A virus, H7N9. Clin Vaccine Immunol. 2013; 20(12), 1836-1837.

49. Deal, C., Balazs, A. B., Espinosa, D. A., Zavala, F., Baltimore, D., and Ketner, G. Vectored antibody gene delivery protects against *Plasmodium falciparum* sporozoite challenge in mice. Proc Natl Acad Sci USA. 2014; 111(34), 12528-12532.

50. Prasad, K. M., Smith, R. S., Xu, Y., and French, B. A. A single direct injection into the left ventricular wall of an adeno-associated virus 9 (AAV9) vector expressing extracellular superoxide dismutase from the cardiac troponin-T promoter protects mice against myocardial infarction. J Gene Med. 2011; 13(6), 333-341.

51. Hu, C. and Lipshutz, G. S. AAV-based neonatal gene therapy for hemophilia A: long-term correction and avoidance of immune responses in mice. Gene Ther. 2012; 19(12), 1166-1176.

52. Kbrbelin, J., Dogbevia, G., Michelfelder, S., Ridder, D. A., Hunger, A., Wenzel, J., Seismann, H., Lampe, M., Bannach, J., Pasparakis, M., Kleinschmidt, J. A., Schwaninger, M., and Trepel, M. A brain microvasculature endothelial cell-specific viral vector with the potential to treat neurovascular and neurological diseases. EMBO Mol Med. 2016; 8(6), 609-625.

53. Michelfelder, S., Varadi, K., Raupp, C., Hunger, A., KOrbelin, J., Pahrmann, C., Schrepfer, S., Müller, O. J., Kleinschmidt, J. A., and Trepel, M. Peptide ligands incorporated into the threefold spike capsid domain to re-direct gene transduction of AAV8 and AAV9 in vivo. PLoS One. 2011; 6(8), e23101.

54. Greig, J. A., Peng, H., Ohlstein, J., Medina-Jaszek, C. A., Ahonkhai, O., Mentzinger, A., Grant, R. L., Roy, S., Chen, S. J., Bell, P., Tretiakova, A. P., and Wilson, J. M. Intramuscular injection of AAV8 in mice and macaques is associated with substantial hepatic targeting and transgene expression. PLoS One. 2014; 9(11), e112268.

55. Qiu, X., Wong, G., Audet, J., Bello, A., Fernando, L., Alimonti, J. B., Fausther-Bovendo, H., Wei, H., Aviles, J., Hiatt, E., Johnson, A., Morton, J., Swope, K., Bohorov, O., Bohorova, N., Goodman, C., Kim, D., Pauly, M. H., Velasco, J., Pettitt, J., Olinger, G. G., Whaley, K., Xu, B., Strong, J. E., Zeitlin, L., and Kobinger, G. P. Reversion of advanced Ebola virus disease in nonhuman primates with ZMapp. Nature. 2014; 514(7520), 47-53.

56. Davey, R. T., Dodd, L., Proschan, M. A., Neaton, J., Neuhaus Nordwall, J., Koopmeiners, J. S., Beigel, J., Tierney, J., Lane, H. C., Fauci, A. S., Massaquoi, M. B. F., Sahr, F., and Malvy, D. A Randomized, Controlled Trial of ZMapp for Ebola Virus Infection. N Engl J Med. 2016; 375, 1448-1456.

57. Croyle, M. A., Cheng, X., and Wilson, J. M. Development of formulations that enhance physical stability of viral vectors for gene therapy. Gene Ther. 2001; 8(17), 1281-1290.

58. Flyak, A. I., Shen, X., Murin, C. D., Turner, H. L., David, J. A., Fusco, M. L., Lampley, R., Kose, N., Ilinykh, P. A., Kuzmina, N., Branchizio, A., King, H., Brown, L., Bryan, C., Davidson, E., Doranz, B. J., Slaughter, J. C., Sapparapu, G., Klages, C., Ksiazek, T. G., Saphire, E. O., Ward, A. B., Bukreyev, A., and Crowe, J. E., Jr. Cross-Reactive and Potent Neutralizing Antibody Responses in Human Survivors of Natural Ebolavirus Infection. Cell. 2016; 164(3), 392-405.

59. Zhang, Q., Gui, M., Niu, X., He, S., Wang, R., Feng, Y., Kroeker, A., Zuo, Y., Wang, H., Wang, Y., Li, J., Li, C., Shi, Y., Shi, X., Gao, G. F., Xiang, Y., Qiu, X., Chen, L., and Zhang, L. Potent neutralizing monoclonal antibodies against Ebola virus infection. Sci Rep. 2016; 6, 25856.
60. Corti, D., Misasi, J., Mulangu, S., Stanley, D. A., Kanekiyo, M., Wollen, S., Ploquin, A., Doria-Rose, N. A., Staupe, R. P., Bailey, M., Shi, W., Choe, M., Marcus, H., Thompson, E. A., Cagigi, A., Silacci, C., Fernandez-Rodriguez, B., Perez, L., Sallusto, F., Vanzetta, F., Agatic, G., Cameroni, E., Kisalu, N., Gordon, I., Ledgerwood, J. E., Mascola, J. R., Graham, B. S., Muyembe-Tamfun, J. J., Trefry, J. C., Lanzavecchia, A., and Sullivan, N. J. Protective monotherapy against lethal Ebola virus infection by a potently neutralizing antibody. Science. 2016; 351(6279), 1339-1342.
61. Fang, Qian, Harding, Tu, VanRoey J. Stable antibody expression at therapeutic levels using the 2A peptide. Nat Biotech. 2005; 23(5):584-90.
62. Van Lieshout L P, Domm J M, Rindler T N, et al. A Novel Triple-Mutant AAV6 Capsid Induces Rapid and Potent Transgene Expression in the Muscle and Respiratory Tract of Mice. Mol Ther—Methods Clin Dev. 2018; 9:323-329.
63. Andersen J T, Daba M B, Michaelsen T E, Sandlie I. Cross-species Binding Analyses of Mouse and Human Neonatal Fc Receptor Show Dramatic Differences in Immunoglobulin G and Albumin Binding. J Biol Chem. 2010; 285(7):4826-4836.
64. Edwards K M. Maternal antibodies and infant immune responses to vaccines. Vaccine. 2015; 33(47):6469-6472.
65. Hashemi H, Mohebbi M, Mehravaran S, Mazloumi M, Ardakani H J, Abtahi S H. Hyperimmunoglobulin e syndrome: Genetics, immunopathogenesis, clinical findings, and treatment modalities. J Res Med Sci. 2017; 22(1).
66. Klein-Schneegans A S, Kuntz L, Fonteneau P, Loor F. Serum concentrations of IgM, IgG1, IgG2b, IgG3 and IgA in C57BL 6 mice and their congenics at the Ipr (lymphoproliferation) locus. J Autoimmun. 1989; 2(6): 869-875.
67. Melton K R, Nesslein L L, Ikegami M, Tichelaar J W, Clark J C, Whitsett J A, Weaver T E. SP-B deficiency causes respiratory failure in adult mice. American Journal of Physiology-Lung Cellular and Molecular Physiology. 2003. 285(3):L543-L549.

U.S. Pat. No. 5,478,745

---

The invention claimed is:

1. A recombinant adeno-associated viral (rAAV) particle comprising a mutated capsid protein encapsidating a rAAV vector genome, wherein the mutated capsid protein comprises amino acid substitutions at amino acids 129, 445, and 731 of the AAV6 capsid protein sequence as set forth in SEQ ID NO:1, and wherein the rAAV vector genome comprises at least one heterologous nucleic acid segment flanked by AAV ITRs encoding a therapeutic agent operably linked to a promoter capable of expressing the segment in a host cell.

2. The rAAV particle of claim 1, wherein the mutated capsid protein has amino acid substitutions Phe129Leu, Tyr445Phe and Tyr731Phe, and wherein the mutated capsid protein is mutated AAV6 capsid protein having an amino acid sequence as shown in SEQ ID NO:2.

3. The rAAV particle of claim 1, wherein the therapeutic agent is a polypeptide, a therapeutic protein, an antigen, an antibody, or an antigen binding fragment, or a combination thereof.

4. A method of treating or preventing an infectious, acquired or genetic disease comprising administering at least one rAAV particle of claim 1 to a subject in need thereof.

5. The method of claim 4, wherein the infectious disease is selected from the group consisting of a viral disease, a bacterial disease, and a drug resistant parasitic disease, wherein the viral disease is selected from the group consisting of viral hemorrhagic fever, Ebola, Marburg virus disease, gastroenteritis, dengue fever, West Nile fever, yellow fever, influenza, respiratory syncytial virus disease, Lassa fever, rabies, smallpox, cowpox, horsepox, monkeypox, Hantavirus pulmonary syndrome, Hendra virus disease, human immunodeficiency virus disease and acquired immunodeficiency disease syndrome, Hepatitis, Zika fever, and wherein the bacterial disease is tuberculosis or methicillin-resistant *Staphylococcus aureus* infection, wherein the drug resistant parasitic disease is malaria, and wherein the acquired or genetic disease is selected from the group consisting of cancer, autoimmune disorders, vascular degeneration, neurodegenerative diseases such as Huntington's disease, cystic fibrosis, inflammatory bowel diseases such as Crohn's Disease, and surfactant protein B deficiency.

6. The method of claim 5, wherein the infectious disease is Ebola or Marburg virus disease, and wherein the therapeutic agent comprises an antibody, or a fragment thereof, or an antigen binding fragment, or a combination thereof, against Ebola or Marburg virus.

7. The method of claim 4, wherein the subject is human.

8. The method of claim 7, wherein the at least one rAAV particle is administered intravenously, intranasally, intratracheally, intramuscularly, intraperitoneally, or via aerosol.

9. The method of claim 4, wherein the at least one rAAV particle is delivered to lung cells or tissues.

10. The method of claim 6, wherein the antibody is a monoclonal antibody, wherein the monoclonal antibody is 1H3 which comprises a light chain comprising the amino acid sequence set forth in SEQ ID NO:3 and a heavy chain comprising the amino acid sequence set forth in SEQ ID NO:4, 2G4 which comprises a light chain comprising the amino acid sequence set forth in SEQ ID NO:5 and a heavy chain comprising the amino acid sequence set forth in SEQ ID NO:6, 4G7 which comprises a light chain comprising the amino acid sequence set forth in SEQ ID NO:7 and a heavy chain comprising the amino acid sequence set forth in SEQ ID NO:8, 5D2 which comprises a light chain comprising the amino acid sequence set forth in SEQ ID NO:9 and a heavy chain comprising the amino acid sequence set forth in SEQ ID NO:10, 7C9 which comprises a light chain comprising the amino acid sequence set forth in SEQ ID NO:11 and a heavy chain comprising the amino acid sequence set forth in SEQ ID NO:12, 100 which comprises a light chain comprising the amino acid sequence set forth in SEQ ID NO:13 and a heavy chain comprising the amino acid sequence set forth in SEQ ID NO:14, 114 which comprises a light chain comprising the amino acid sequence set forth in SEQ ID NO:15 and a heavy chain comprising the amino acid sequence set forth in SEQ ID NO:16, CA45 which comprises a light chain comprising the amino acid sequence set forth in SEQ ID NO:17 and a heavy chain comprising the amino acid sequence set forth in SEQ ID NO:18, ADI-15878 which comprises a light chain comprising the amino acid sequence set forth in SEQ ID NO:19 and a heavy chain comprising the amino acid sequence set forth in SEQ ID NO:20, FVM02p which comprises a light chain comprising the amino acid sequence set forth in SEQ ID NO:21 and a heavy chain comprising the amino acid sequence set forth in SEQ ID NO:22, FVM04 which comprises a light chain comprising the amino acid sequence set forth in SEQ ID NO:23 and a heavy chain comprising the amino acid sequence set forth in SEQ ID NO:24, BDBV223 which comprises a light chain comprising the amino acid sequence set forth in SEQ ID NO:25 and a heavy chain comprising the amino acid sequence set forth in SEQ ID NO:26, or a fragment thereof, or a combination cocktail thereof, against Ebola virus, or MR72 which comprises a light chain comprising the amino acid sequence set forth in SEQ ID NO:27 and a heavy chain comprising the amino acid sequence set forth in SEQ ID NO:28, MR82 which comprises a light chain comprising the amino acid sequence set forth in SEQ ID NO:29 and a heavy chain comprising the amino acid sequence set forth in SEQ ID NO:30, MR78 which comprises a light chain comprising the amino acid sequence set forth in SEQ ID NO:31 and a heavy chain comprising the amino acid sequence set forth in SEQ ID NO:32, MR191 which comprises a light chain comprising the amino acid sequence set forth in SEQ ID NO:33 and a heavy chain comprising the amino acid sequence set forth in SEQ ID NO:34, or a fragment thereof, or a combination thereof, against Marburg virus.

11. The method of claim 6, wherein the therapeutic agent remains in the serum of the subject for at least 2, 4, 8, 10, 12, 14, 16 or 18 weeks, and/or up to 26, 28, 30, 32, or 34 weeks.

12. The method of claim 6, wherein the subject is protected from Ebola from 3, 7 or 14 days post administration to at least 3 weeks, or 1, 2, 3, 4, or 5 months.

13. A mutated AAV capsid protein comprising (a) amino acid substitutions at amino acids 129, 445, and 731 of the AAV6 capsid protein sequence as set forth in SEQ ID NO:1, or (b) amino acid substitutions Phe129Leu, Tyr445Phe and Tyr731Phe, wherein the mutated capsid protein is mutated AAV6 capsid protein having an amino acid sequence as shown in SEQ ID NO:2.

14. A method of producing at least one protein in vivo in a subject, comprising introducing into the subject at least one rAAV particle of claim 1.

15. The method of claim 14, wherein the mutated capsid protein has amino acid substitutions Phe129Leu, Tyr445Phe and Tyr731Phe, and wherein the mutated capsid protein is mutated AAV6 capsid protein having an amino acid sequence as shown in SEQ ID NO:2.

16. The method of claim 14, wherein the at least one protein is a monoclonal antibody or a fragment thereof, and wherein the monoclonal antibody is 1H3 which comprises a light chain comprising the amino acid sequence set forth in SEQ ID NO:3 and a heavy chain comprising the amino acid sequence set forth in SEQ ID NO:4, 2G4 which comprises a light chain comprising the amino acid sequence set forth in SEQ ID NO:5 and a heavy chain comprising the amino acid sequence set forth in SEQ ID NO:6, 4G7 which comprises a light chain comprising the amino acid sequence set forth in SEQ ID NO:7 and a heavy chain comprising the amino acid sequence set forth in SEQ ID NO:8, 5D2 which comprises a light chain comprising the amino acid sequence set forth in SEQ ID NO:9 and a heavy chain comprising the amino acid sequence set forth in SEQ ID NO:10, 7C9 which comprises a light chain comprising the amino acid sequence set forth in SEQ ID NO:11 and a heavy chain comprising the amino acid sequence set forth in SEQ ID NO:12, 100 which comprises a light chain comprising the amino acid sequence set forth in SEQ ID NO:13 and a heavy chain comprising the amino acid sequence set forth in SEQ ID NO:14, 114 which comprises a light chain comprising the amino acid sequence set forth in SEQ ID NO:15 and a heavy chain comprising the amino acid sequence set forth in SEQ ID NO:16, CA45 which comprises a light chain comprising the amino acid sequence set forth in SEQ ID NO:17 and a heavy chain comprising the amino acid sequence set forth in SEQ ID NO:18, ADI-15878 which comprises a light chain comprising the amino acid sequence set forth in SEQ ID NO:19 and a heavy chain comprising the amino acid sequence set forth in SEQ ID NO:20, FVM02p which comprises a light chain comprising the amino acid sequence set forth in SEQ ID NO:21 and a heavy chain comprising the amino acid sequence set forth in SEQ ID NO:22, FVM04 which comprises a light chain comprising the amino acid sequence set forth in SEQ ID NO:23 and a heavy chain comprising the amino acid sequence set forth in SEQ ID NO:24, BDBV223 which comprises a light chain comprising the amino acid sequence set forth in SEQ ID NO:25 and a heavy chain comprising the amino acid sequence set forth in SEQ ID NO:26, or a fragment thereof, or a combination cocktail thereof, against Ebola virus, or MR72 which comprises a light chain comprising the amino acid sequence set forth in SEQ ID NO:27 and a heavy chain comprising the amino acid sequence set forth in SEQ ID NO:28, MR82 which comprises a light chain comprising the amino acid sequence set forth in SEQ ID NO:29 and a heavy chain comprising the amino acid sequence set forth in SEQ ID NO:30, MR78 which comprises a light chain comprising the amino acid sequence set forth in SEQ ID NO:31 and a heavy chain comprising the amino acid sequence set forth in SEQ ID NO:32, MR191 which comprises a light chain comprising the amino acid sequence set forth in SEQ ID NO:33 and a heavy chain comprising the amino acid sequence set forth in SEQ ID NO:34, or a fragment thereof, or a combination thereof, against Marburg virus.

17. The method of claim 16, wherein the at least one protein remains in the serum of the subject for at least 2, 4, 8, 10, 12, 14, 16 or 18 weeks, and/or up to 26, 28, 30, 32, or 34 weeks.

18. The method of claim 14, wherein the subject is human.

19. The method of claim 14, wherein the at least one rAAV particle is administered intravenously, intranasally, intratracheally, intramuscularly, or via aerosol.

20. The rAAV particle of claim 3, wherein the therapeutic protein is surfactant protein B (SPB).

21. The method of claim 4, wherein the genetic disease is surfactant protein B deficiency, and wherein the therapeutic agent is surfactant protein B (SPB).

22. The method of claim 9, wherein the at least one rAAV particle targets alveolar epithelial type 2 (AT2) cells.

23. The method of claim 22, wherein the infectious disease is influenza or respiratory syncytial virus disease, or wherein the genetic disease is cystic fibrosis.

* * * * *

SEQUENCE LISTING

<160> NUMBER OF SEQ ID NOS: 40

<210> SEQ ID NO 1
<211> LENGTH: 736
<212> TYPE: PRT
<213> ORGANISM: Adeno-associated dependo parvovirus A

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205
```

```
Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620
```

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 2
<211> LENGTH: 736
<212> TYPE: PRT
<213> ORGANISM: Artificial Sequence
<220> FEATURE:
<223> OTHER INFORMATION: Synthetic construct

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

```
Tyr Lys Gln Ile Ser Ser Ala Ser Thr Gly Ala Ser Asn Asp Asn His
                260             265             270

Tyr Phe Gly Tyr Ser Thr Pro Trp Gly Tyr Phe Asp Phe Asn Arg Phe
            275             280             285

His Cys His Phe Ser Pro Arg Asp Trp Gln Arg Leu Ile Asn Asn Asn
        290             295             300

Trp Gly Phe Arg Pro Lys Arg Leu Asn Phe Lys Leu Phe Asn Ile Gln
305             310             315             320

Val Lys Glu Val Thr Thr Asn Asp Gly Val Thr Thr Ile Ala Asn Asn
                325             330             335

Leu Thr Ser Thr Val Gln Val Phe Ser Asp Ser Glu Tyr Gln Leu Pro
            340             345             350

Tyr Val Leu Gly Ser Ala His Gln Gly Cys Leu Pro Pro Phe Pro Ala
        355             360             365

Asp Val Phe Met Ile Pro Gln Tyr Gly Tyr Leu Thr Leu Asn Asn Gly
        370             375             380

Ser Gln Ala Val Gly Arg Ser Ser Phe Tyr Cys Leu Glu Tyr Phe Pro
385             390             395             400

Ser Gln Met Leu Arg Thr Gly Asn Asn Phe Thr Phe Ser Tyr Thr Phe
                405             410             415

Glu Asp Val Pro Phe His Ser Ser Tyr Ala His Ser Gln Ser Leu Asp
            420             425             430

Arg Leu Met Asn Pro Leu Ile Asp Gln Tyr Leu Tyr Phe Leu Asn Arg
        435             440             445

Thr Gln Asn Gln Ser Gly Ser Ala Gln Asn Lys Asp Leu Leu Phe Ser
    450             455             460

Arg Gly Ser Pro Ala Gly Met Ser Val Gln Pro Lys Asn Trp Leu Pro
465             470             475             480

Gly Pro Cys Tyr Arg Gln Gln Arg Val Ser Lys Thr Lys Thr Asp Asn
                485             490             495

Asn Asn Ser Asn Phe Thr Trp Thr Gly Ala Ser Lys Tyr Asn Leu Asn
            500             505             510

Gly Arg Glu Ser Ile Ile Asn Pro Gly Thr Ala Met Ala Ser His Lys
        515             520             525

Asp Asp Lys Asp Lys Phe Phe Pro Met Ser Gly Val Met Ile Phe Gly
        530             535             540

Lys Glu Ser Ala Gly Ala Ser Asn Thr Ala Leu Asp Asn Val Met Ile
545             550             555             560

Thr Asp Glu Glu Glu Ile Lys Ala Thr Asn Pro Val Ala Thr Glu Arg
                565             570             575

Phe Gly Thr Val Ala Val Asn Leu Gln Ser Ser Ser Thr Asp Pro Ala
            580             585             590

Thr Gly Asp Val His Val Met Gly Ala Leu Pro Gly Met Val Trp Gln
        595             600             605

Asp Arg Asp Val Tyr Leu Gln Gly Pro Ile Trp Ala Lys Ile Pro His
        610             615             620

Thr Asp Gly His Phe His Pro Ser Pro Leu Met Gly Gly Phe Gly Leu
625             630             635             640

Lys His Pro Pro Pro Gln Ile Leu Ile Lys Asn Thr Pro Val Pro Ala
                645             650             655

Asn Pro Pro Ala Glu Phe Ser Ala Thr Lys Phe Ala Ser Phe Ile Thr
            660             665             670
```

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Phe Leu Thr Arg Pro Leu
                725                 730                 735

<210> SEQ ID NO 3
<211> LENGTH: 373
<212> TYPE: DNA
<213> ORGANISM: Mus Musculus

<400> SEQUENCE: 3
tggggcagag cttgtgaagc caggggcctc agtcaagttg tcctgcacag cttctggctt      60
caacattaaa gacacctata cattgggt gaaacagggg cctgaacagg cctggagtg      120 gattggaagg attgatcctg cgaatggtaa tactaaatat gacccgaagt tccagggcaa      180
ggccactatc acagcagaca catcctccaa tacagcctac ctgcagctca gcggcctgac      240
atctgaggac actgccgtct attactgtgc tagggagtcg aggatatcta ctatgcttac      300 gacgggtac tttgactact ggggccaagg caccactctc acagtctcct cagccaaaac      360 aacagccccca tcg                                                         373

<210> SEQ ID NO 4
<211> LENGTH: 303
<212> TYPE: DNA
<213> ORGANISM: Mus Musculus

<400> SEQUENCE: 4
gcaatcatgt ctgcatctcc aggggagaag gtcaccatga cctgcagtgc cagctcaagt      60
gtaagttaca tgtactggta ccagcagaag ccaggatcct cccccagact cctgattat      120 gacacatcca acctggcttc tggagtccct gttcgcttca gtggcagtgg gtctgggacc      180
tcttactctc tcacaatcag ccgaatggag gctgaagatg ctgccactta ttactgccag      240
cagtggagta gttacccgta cacgttcgga gggggacca agctggaaat aaaacgggct      300
gat                                                                    303

<210> SEQ ID NO 5
<211> LENGTH: 364
<212> TYPE: DNA
<213> ORGANISM: Mus Musculus

<400> SEQUENCE: 5
tggaggaggc ttgatgcaac ctggaggatc catgaaactc tcctgtgttg cctcaggatt      60
cactttcagt aactactgga tgaactgggt ccgccagtct ccagagaagg ggcttgagtg      120
ggttgctgaa attagattga aatctaataa ttatgcaaca cattatgcgg agtctgtgaa      180
agggaggttc accatttcaa gagatgattc caaaaggagt gtctacctgc aaatgaatac      240
cttaagagct gaagacactg gcatttatta ctgtacccgg gggaatggta actacagggc      300
tatggactac tggggtcaag gaacctcagt caccgtctcc tcagccaaaa caacacccc      360 atca                                                                    364

```
<210> SEQ ID NO 6
<211> LENGTH: 306
<212> TYPE: DNA
<213> ORGANISM: Mus Musculus

<400> SEQUENCE: 6
gcctccctat ctgtatctgt gggagaaact gtctccatca catgtcgagc aagtgagaat      60
atttacagta gtttagcatg gtatcagcag aaacagggaa atctcctca gctcctggtc      120 tattctgcaa caatcttagc agatggtgtg ccatcaaggt tcagtggcag tggatcaggc     180
actcagtatt ccctcaagat caacagcctg cagtctgaag attttgggac ttattactgt     240
caacattttt ggggtactcc gtacacgttc ggagggggga ccaagctgga aataaaacgg     300
gctgat                                                                306

<210> SEQ ID NO 7
<211> LENGTH: 358
<212> TYPE: DNA
<213> ORGANISM: Mus Musculus

<400> SEQUENCE: 7
tggacctgag ctggagatgc ctggcgcttc agtgaagata tcctgcaagg cttctggttc      60
ctcattcact ggcttcagta tgaactgggt gaagcagagc aatggaaaga ccttgagtg      120 gattggaaat attgatactt attatggtgg tactacctac aaccagaaat tcaagggcaa     180
ggccacattg actgtggaca atcctccag cacagcctac atgcagctca gagcctgac      240 atctgaggac tctgcagtct attactgtgc aagatcggcc tactacggta gtacttttgc     300
ttactggggc caagggactc tggtcactgt ctctgcagcc aaaacaacag ccccatcg      358

<210> SEQ ID NO 8
<211> LENGTH: 306
<212> TYPE: DNA
<213> ORGANISM: Mus Musculus

<400> SEQUENCE: 8
gcctccctat ctgcatctgt gggagaaact gtcaccatca catgtcgagc aagtgagaat      60
atttacagtt atttagcatg gtatcagcag aaacagggaa atctcctca gctcctggtc      120 tataatgcca aaaccttaat agagggtgtg ccatcaaggt tcagtggcag tggatcaggc     180
acacagtttt ctctgaagat caacagcctg cagcctgaag attttgggag ttatttctgt     240
caacatcatt ttggtactcc attcacattc ggctcgggga cagagttgga aataaaacgg     300
gctgat                                                                306

<210> SEQ ID NO 9
<211> LENGTH: 340
<212> TYPE: DNA
<213> ORGANISM: Mus Musculus

<400> SEQUENCE: 9
gggacctggc ctggtgagac cttctcagtc tctgtccctc acctgcactg tcactggcta      60
ctcaatcacc agtgattatg cctggaactg gatccgcag tttccaggaa acaaactgga      120
gtggctgggc tatataacca acactggtag cactggcttc aacccatctc tcaaaagtcg     180
aatctctatc actcgagaca catccaagaa ccagttcttc ctgcagttga tttctgtgac     240
tactgaggac acagccacat atcactgtgc aaggggcctt gcttactggg gccaagggac     300
tctggtcact gtctctgcag ccaaaacaac agccccatcg                            340
```

<210> SEQ ID NO 10
<211> LENGTH: 321
<212> TYPE: DNA
<213> ORGANISM: Mus Musculus

<400> SEQUENCE: 10

```
ctcactttgt cggttaccat tggacaacca gcctccatct cttgcaagtc aagtcagagc    60
ctcttagata gtgatggaaa gacatatctg aattggttgt tacagaggcc aggccagtct   120
ccaaagcgcc taatctatct ggtgtctaaa ctggactctg gagtcactga caggttcact   180
ggcagtggat cagggacaga tttcacactg aaaatcagca gagtggaggc tgaggatttg   240
ggagtttatt attgttggca aggtacacac tctccattca cgttcggctc ggggacaaag   300
ttggaaataa aacgggctga t                                             321
```

<210> SEQ ID NO 11
<211> LENGTH: 358
<212> TYPE: DNA
<213> ORGANISM: Mus Musculus

<400> SEQUENCE: 11

```
tggggcagag cttgtgaagc caggggcctc agtcaagttg tcctgcacag cttctggctt    60
caacattaaa gacacctata tgcactgggt gaaggagagg cctgacaagg gcctggagtg   120
gattggaagg attgatccag cgaatggtaa tactaaatgt gactcgaggt tcagggcaa   180 ggccactata acagcagaca catcctccaa cacagcctac ctgcagctca gcagcctgac   240
atctgaggac actgccgtct attactgtgc tagaaggatc tactttggta agggctttga   300
cttttggggc caaggcacca ctctcacagt ctcctcagcc aaaacaacag ccccatcg    358
```

<210> SEQ ID NO 12
<211> LENGTH: 324
<212> TYPE: DNA
<213> ORGANISM: Mus Musculus

<400> SEQUENCE: 12

```
tcctccctga gtgtgtcagc aggagagaag gtcactatga gctgcaagtc cagtcagagt    60
ctgtttaaca gtggagatca aaagaactac ttggcctggt accagcagaa accagggcag   120
cctcctaaac tgttgatcta cggggcatcc actagggaat ctggggtccc tgatcgcttc   180
acaggcagtg gatctggaac cgatttcact cttaccatca gcagtgtgca ggctgaagac   240
ctggcagttt attactgtca gaatgatcaa tttatcctc ccacgttcgg tgatgggacc   300
aagctggacc tgaaacgggc tgat                                          324
```

<210> SEQ ID NO 13
<211> LENGTH: 375
<212> TYPE: DNA
<213> ORGANISM: Homo Sapiens

<400> SEQUENCE: 13

```
caggtgcaac ttcaggagtc agggcctggc ctcgtcaaac caagcgatac actgagtttg    60
acttgcacag tgagtggggg tagtttgtct agtttctatt ggtcttggat tcggcaaccc   120
cccggcaaag gtcttgagtg gataggatac atctactact cagggtcccc caattactca   180
ccttccctgg aatctagggt tactatgtcc gtggacacaa cccgaaatca atatccttg   240 aagcttgact ccgtgacagc cgcagacacc gccgtttact actgcgtccg agcatcccgc   300
```

```
tcctattatt ggggtagcta tcgaccaact gcttttgatt cttggggaca ggggacactt      360
gtaactgtct caagc                                                      375

<210> SEQ ID NO 14
<211> LENGTH: 315
<212> TYPE: DNA
<213> ORGANISM: Homo Sapiens

<400> SEQUENCE: 14
tcttatgaac tcactcagcc actttctgtc agtgtcagcc caggtcagac cgccatattt       60
acctgcagtg gcgataactt gggcgacaaa tacgtgtgtt ggtttcagca acggcccggc      120
cagtcaccca tgctccttat ctatcaagac aacaagcgac cttcaggcat ccccgagcgg      180
tttagtgggt ctaactctgg gaacaccgct acattgacta ttagtggaac tcagtcaacc      240
gatgaagccg actattactg ccaaacttgg gattccaccg tagttttcgg cggcggaact      300
aagttgacag tgttg                                                      315

<210> SEQ ID NO 15
<211> LENGTH: 357
<212> TYPE: DNA
<213> ORGANISM: Homo Sapiens

<400> SEQUENCE: 15
gaggtgcaac tggtcgaatc tggtggagga cttatccagc ctggtggcag cctgagactt       60
tcttgcgcag ctagtggatt tgctttgagg atgtatgaca tgcattgggt acgacagaca      120
atagacaaac ggttggaatg ggtttctgct gtaggcccta gcggagacac ctactacgca      180
gacagcgtga agggtaggtt tgcagtttca cgggagaacg ctaagaacag cctctcactt      240
caaatgaata gcctcaccgc tggcgacaca gcaatctact actgtgtaag aagtgatagg      300
ggtgttgccg ggctgtttga cagttgggga cagggtattt tggtaaccgt gagcagt        357

<210> SEQ ID NO 16
<211> LENGTH: 321
<212> TYPE: DNA
<213> ORGANISM: Homo Sapiens

<400> SEQUENCE: 16
gacatacaga tgacccaaag cccttcatcc ctctctgctt ctgtaggtga caggattaca       60
atcacctgcc gcgcaagtca ggcttttgac aactatgtgg catggtatca gcaacgacca      120
gggaaggtcc caaaattgct gatctccgct gcctccgctc ttcacgcagg agtcccttct      180
aggttttctg gatcagggtc cggtactcac ttcaccctca ctatatcaag tctccaacct      240
gaagacgtgg ccacctacta ctgccagaat tataacagtg ctccacttac ttttggtgga      300
ggaacaaagg tagagataaa a                                               321

<210> SEQ ID NO 17
<211> LENGTH: 387
<212> TYPE: DNA
<213> ORGANISM: Homo Sapiens

<400> SEQUENCE: 17
caagttcaat tgcaagagtg gggggagggc ctggttaagc ccagcgaaac tttgagcttg       60
acatgtgctg tgtatggcgg ctctatcagt ggttactacc actggaattg gataaggctc      120 cccccccggca aagggctcga gtggatcggg aatatagatg gtaacagcgc aagtacaaat      180
tacaatccct tctctgaaga ccgagtgacc attagcaagg ataccagcaa aaatcaaatt      240
```
agtttgaaag tacgatccett gactgccgcc gacaccgccg tctactattg cgctagggac    300
cctggattca ctatatttgg agtagttatc acatcatggt ccggcctcga ctcttggggt    360 caggggggcag tggtgacagt ttcatct                                       387

<210> SEQ ID NO 18
<211> LENGTH: 321
<212> TYPE: DNA
<213> ORGANISM: Homo Sapiens

<400> SEQUENCE: 18
gatatacaga tgacacaaag tccctcatct ttgtcagctt ctgtggggga taccgttact     60
attacttgta gggcatccca atcaatttct aataatctgg catggtatca acagcgccct    120
agaagagccc cacaactgct gatctacgcc gcctctaacc ttgcttcagg tgtgccctcc    180
cgattttcag gatcaggttc agggacagat tttactctca caatttcctc tcttcaagca    240
gaggactttg ctgcttacta ctgccagcag cataatactc tccctctcac ctttggtggt    300
ggaacaaaag ttgagattaa g                                              321

<210> SEQ ID NO 19
<211> LENGTH: 279
<212> TYPE: DNA
<213> ORGANISM: Homo Sapiens

<400> SEQUENCE: 19
caagtccaac tggtccaatc aggagtgacc cttgttcaac ctggtgggag ccttagagtt     60
agttgtgcag ccagcggttt tacctttagt agctatgcta tgagctgggt acgccaagct    120
cctggcaagg gcctggagtg ggtaagcgct atctccggtt tggggggttc tacatactac    180
gcagattcag ttaagggaag gttcactatt tctcgggata actccaaaaa cacactttat    240
cttcagatga actctcttcg cgcagaagac actgctgtt                           279

<210> SEQ ID NO 20
<211> LENGTH: 318
<212> TYPE: DNA
<213> ORGANISM: Homo Sapiens

<400> SEQUENCE: 20
gacatagtgc tgactcagag tccttccact cttttcagcta gtgtagggga ccgcgtcaca    60
ataacatgca gagcttcaca atccataagc tcctggttgg cttggtacca acagaagcct   120
ggggaagctc ccaaactctt gattagcgac gcttcaagtt tggagtcagg ggtaccctca   180
aggttctctg gcagtgggtc cggtacagaa tttacccctca caataagcag cttgcaacct   240
gacgacttcg ctacatacta ttgtcagcag tattatagtt ctccaacctt cggagggggt   300
accaaagtgg aaattaaa                                                  318

<210> SEQ ID NO 21
<211> LENGTH: 279
<212> TYPE: DNA
<213> ORGANISM: Macaca fascicularis

<400> SEQUENCE: 21
gaagttcagt tggtagagtc aggcggcgga ttggtgcaac ctggtgggtc cctcagattg     60
agttgtgccg cttccgggtt tacaggattt acttttctg actacgcatt ctattgggtg    120
agacaggcac ctggaaaagg tttggaatgg gtaggattca ttaggggcaa ggcatacgga    180

```
ggtacagcag actacgccgc ttctgttaaa ggaaggttca ccatttctcg agataattcc    240
aaaaacactg cctatttgca gatgagctct ttgaagaca                          279

<210> SEQ ID NO 22
<211> LENGTH: 345
<212> TYPE: DNA
<213> ORGANISM: Macaca fascicularis

<400> SEQUENCE: 22
gacatcgttc tcacacaatc acccctcagc ttgcccgtca cacccggcga gccagctagt    60
atcagttgta ggtcctctca gagtttgctg cactctgggg gtaaaactta cctctattgg    120
tatcttcaaa agcctggtca gtcccccag cttcttattc atgaagtatc caacagagca     180
tctggagtgc ctgatagatt ttctggtagt ggttctggaa ctgatttcac cttgaagatc    240
agccgagtgg aggccgagga cgtgggagta tattactgca tgcagggaat acagttgcct    300
ctgacctttg ggggaggaac aaaagttgag ataaaacgaa ctgta                    345

<210> SEQ ID NO 23
<211> LENGTH: 354
<212> TYPE: DNA
<213> ORGANISM: Macaca fascicularis

<400> SEQUENCE: 23
gaagtgcaac ttgtccaatc tgggggcggc ctggtacaac caggcggatc tatgcggctc    60
tcatgcgagg catcaggact gtctctcagt gattatttta tgcattgggt ccggcaggcc    120
cagggaaaag gtttggagtg gatcggtttg atacagacaa aggctttcac ctataaaacc    180
gaataccctg ctgctgttaa gggtcgcttt accatctcac gggacgatag taagaacact    240
ctgtatttgc aaatgtcttc acttaagcca gaggatacag cattgtacta ctgcattgcc    300 gtgaccccg acttttatta ctggggtcag ggagtgttgg tcaccgtatc ttcc          354

<210> SEQ ID NO 24
<211> LENGTH: 330
<212> TYPE: DNA
<213> ORGANISM: Macaca fascicularis

<400> SEQUENCE: 24
gacgttgtta tgacccagtc cccaagtttc ctgtctgcta gtgttggcga tagagtaact    60
atcacctgta gggctagtca agacataacc ataaatctca attggtttca gcataagcct    120
ggaaaggccc caaagcggct gatctacgtt gcatcccgct tggaacgagg ggtgcccagt    180
cggttctcag gaagcggcag cgggacagaa tttactctta ctatttcaag ccttcagcct    240
gaagattttg ccacatatta ctgtcaacag tataataact atccctgac ctttggtcct     300 gggacaaaac tcgatataaa gcgaaccgta                                     330

<210> SEQ ID NO 25
<211> LENGTH: 321
<212> TYPE: DNA
<213> ORGANISM: Homo Sapiens

<400> SEQUENCE: 25
gaaattgtga tgacccagtc tccagccatc atgtctgtgt ctccagggaa aagagccacc    60
ctctcctgca gggccagtca gagtgtcagt agcaacttag cctggtacca gcggaaacct    120
ggccaggctc ccaggctcct catctatggt tcttccacca gggccactgg tatcccagcc    180
aggttcagtg gcagtgggtc tgggacagag ttcactctca ccatcagcag cctgcagtct    240
```

```
gaggattttg cagtttatta ctgtctgcaa tattataact ggcctcggac gttcggccaa    300
gggaccaagg tggaaatcaa a                                              321

<210> SEQ ID NO 26
<211> LENGTH: 366
<212> TYPE: DNA
<213> ORGANISM: Homo Sapiens

<400> SEQUENCE: 26
caggtgcagc tacagcagtg gggcgcagga ctgttgaagc cttcggagac cctgtccctc     60
acctgcgctg tctatggtgg gtccttcacg actacctact ggaattggat ccgccagccc    120
ccagggaagg ggctggaatg gatagggaa gtcaattata gtggaaacgc caactacaac    180
ccgtccctca gggtcgagt cgccatatca gtggacacat ccaagaacca gttctccctg    240
aggttgaact ctgtgaccgc cgcggacacg gctatatatt actgtacgag tcgcatacgt    300
tcgcacattg cctactcgtg gaaggggggac gtctggggca agggaccac ggtcaccgtc    360 tcctca                                                              366

<210> SEQ ID NO 27
<211> LENGTH: 384
<212> TYPE: DNA
<213> ORGANISM: Homo Sapiens

<400> SEQUENCE: 27
cagttgcaac ttcaagagtc tggtcctggc ttggtcaaac caagcgagac tctcagcctg     60
acttgtactg tatccggtga cagcataaac aacacaaatt attactgggc ttggatcagg    120
cagccaccag ggaagggcct tgagtatatt ggttcaatct attactctgg tagtacatac    180
tataacccta gcttgaagag tagggtaact atgtcagtgg atgctagtaa gaaccagttc    240
tcactgagac tgtcctctgt cactgctgct gacactgctg tgtactactg gctacccac    300 cccacactcg gcgcttttgt attgctgtgg tttggtgcca acttcgatca ctggggtcag    360
ggtactttgg tgacagtgtc tagc                                          384

<210> SEQ ID NO 28
<211> LENGTH: 330
<212> TYPE: DNA
<213> ORGANISM: Homo Sapiens

<400> SEQUENCE: 28
caagccgtcg tcacacaacc cccctcagtc agcggagcac ctggtcagcg ggtcactatt     60
agctgtaccg gcagcagttc caatataggc gctaactatg atgtgcattg gtatcaacag    120
ctccctggga ctgctcctaa attgctgatg tattccaata ccaacagacc atccggagtt    180
cccgataggt ttagtgggtc caagagcgga acctcagctt cactggcaat taccgggctg    240
caagcagaag acgaagctga ctattactgc caaagttacg acaatagtct taatagctgg    300 gttttttggag ggggaacaca actgaccgtt                                   330

<210> SEQ ID NO 29
<211> LENGTH: 372
<212> TYPE: DNA
<213> ORGANISM: Homo Sapiens

<400> SEQUENCE: 29
caggtgcaac ttgtccagtc cggagctgaa gttaagaagc ctggtgccag cgtcaaggtg     60
agttgcaaag catccggaca tacatttaca acatacgcca tacattgggt tcgccaagca    120
```

```
cctggacaag gtcttgagtg gatgggatgg ataaacccag ataatgacaa cactgaatac    180
tcccaaaaat ttcagggaag ggtaaccata acacgggaca catcagcctc tactgcctac    240
atggagctgt caagtctgat ctctgaagat acagcagtat tttactgtgc aagtgcatcc    300 tataccttt ggtccggata ttatagtggg ctcgattatt ggggacaggg gactctggta    360
accgtaagct cc                                                         372
```

<210> SEQ ID NO 30
<211> LENGTH: 327
<212> TYPE: DNA
<213> ORGANISM: Homo Sapiens

<400> SEQUENCE: 30

```
gagatagtat tgactcagtc tcccggtaca ttgtctctct ccccaggaga aagagctaca    60
ctctcatgtc gagcctctca aagcgtctcc atcaattatc tggcctggta tcaacagaag    120
cctggtcaag cacctaggct ccttatctac ggagcaagct cacgggctac tggtattccc    180
gataggttct ctggctcagg ttccggcacc gatttcactc tcacaattag ccgattggaa    240
ccagaagatt tcgccgtcta ttattgtcaa caatatggta gctctccacc ctggacattc    300
ggacctggga ccaaggtgga cataaaa                                         327
```

<210> SEQ ID NO 31
<211> LENGTH: 375
<212> TYPE: DNA
<213> ORGANISM: Homo Sapiens

<400> SEQUENCE: 31

```
cagctccagc tgcaagaatc tggtcccggt cttgttaaac ctagtgaaac acttagcctg    60
acttgcactg tctcaggcgg gtcaatatca tcttccagtt attactgggg ctggatcagg    120
caaccccctg ggaaaggtct cgaatggatt ggctctgttt attatagcgg aggtgccagt    180
tacaatccta gtctcaagtc acgagccact attagcgttg ataccagcaa aaaccaattc    240 agttttgaatc tggattcagt aagcgcagcc gacacagcca tttattactg tgcttccatt    300 tatgaagtg ggactttcta ttattacttt tacatggacg tgtgggggaa gggttcaaca    360
gttactgtaa gctcc                                                      375
```

<210> SEQ ID NO 32
<211> LENGTH: 321
<212> TYPE: DNA
<213> ORGANISM: Homo Sapiens

<400> SEQUENCE: 32

```
gacattcaga tgactcaatc tcccagttcc ctgtcagcta gtgttgggga ccgggtaacc    60
atcacctgtc aagcaagcca ggtcatcagt aactacctta attggtatca gcagaaacct    120
ggcaaggccc caaagctgct tatatatgat acaagtaacc tcaagacagg ggttcctagt    180
cggttctctg gtagcggtag cggaaccgat ttcaccttta caataagtag tctgcaacca    240
gaggatatag ccacatacta ttgtcaacag tacgaaaatc ttcaattcac tttcgggcct    300
ggcaccaaag tagatatcaa a                                               321
```

<210> SEQ ID NO 33
<211> LENGTH: 378
<212> TYPE: DNA
<213> ORGANISM: Homo Sapiens

```
<400> SEQUENCE: 33
caactccaac tgcaagagag cggaccaggg ctcgtaaaac catcagaaac actgtcactc        60
tcctgtaccg tatcaggtgt aagcatctcc gataattctt attactgggg ttggataaga       120
cagccacctg ggaagggttt ggagtggatt gggaccatct catactcagg caataccctat      180 tacaatcctt ctcttaaatc tagggtcagt atatctggag atacttccaa acaccaactt       240
agcttgaaag tttcatcagt tacagccgct gacaccgcag tgtattactg tgctcgccag       300
cggatcgtaa gtgggtttgt agagtggctt agcaaatttg actattgggg ccaggggacc       360
cttgtaaccg tatctagt                                                    378

<210> SEQ ID NO 34
<211> LENGTH: 336
<212> TYPE: DNA
<213> ORGANISM: Homo Sapiens

<400> SEQUENCE: 34
cagtcagttt tgactcagcc cccctcagtg agtggcgctc caggtcaacg agtcaccatc        60
agttgcactg gatcatcttc taatataggc gctgggtttg acgtacactg gtatcagcag       120
ttgcccggca ctgctcctaa attgctgatt tatgacaata taaccgacc ttccggggtg        180 cctgatcgct ttagtggtag taagtcaggt acatccgcta gcttggctat cactgggctt      240
caagcagaag acgaggccga ttattattgc caatcctacg ataccagctt gtccggcccc      300
gtcgtatttg gcggcggaac taaactcacc gttctc                                336

<210> SEQ ID NO 35
<211> LENGTH: 1134
<212> TYPE: DNA
<213> ORGANISM: Mus Musculus

<400> SEQUENCE: 35
atggccaagt cgcacctact gcagtggcta ctgctgcttc ctaccctctg ctgcccaggt        60
gcagctatca cgtcggcctc atccctggag tgtgcacaag ccctcaattc tggtgccaa       120 agcctggagc atgcagtgca gtgcagagcc ctggggcact gcctgcagga agtctggggg      180
catgcaggag ctaatgacct gtgccaagag tgtgaggata ttgtccacct cctcacaaag      240
atgaccaagg aagatgcttt ccaggaagca atccggaagt tcctggaaca agaatgtgat      300
atccttccct tgaagctgct tgtgccccgg tgtcgccaag tgcttgatgt ctacctgccc      360
ctggttattg actacttcca gagccagatt aaccccaaag ccatctgcaa tcatgtgggc      420
ctgtgcccac gtgggcaggc taagccagaa cagaatccag gatgccgga tgccgttcca       480 aaccctctgc tggacaagct ggtcctccct gtgctgccag gagccctctt ggcaaggcct      540
gggcctcaca ctcaggactt ctctgagcaa cagctcccca ttcccctgcc cttctgctgg      600 cttttgcagaa ctctgatcaa gcgggttcaa gccgtgatcc caagggtgt gctggctgtg      660 gctgtgtccc aggtgtgcca cgtggtaccc ctggtggtgg gtggcatctg ccagtgcctg      720
gctgagcgct acacagttct cctgctagac gcactgctgg gccgtgtggt gccccagcta      780
gtctgtggcc ttgtcctccg atgttccact gaggatgcca tgggccctgc cctccctgct      840
gtggagcctc tgatagaaga atggccacta caggacactg agtgccattt ctgcaagtct      900
gtgatcaacc aggcctggaa caccagtgaa caggctatgc acaggcaat gcaccaggcc       960 tgccttcgct tctggctaga caggcaaaag tgtgaacagt ttgtggaaca gcacatgccc      1020
```

```
cagctgctgg ccctggtgcc taggagccag gatgcccaca tcacctgcca ggcccttggc   1080
gtatgtgagg ccccggctag ccctctgcag tgcttccaaa ccccacacct ctga         1134
```

<210> SEQ ID NO 36
<211> LENGTH: 1170
<212> TYPE: DNA
<213> ORGANISM: Artificial Sequence
<220> FEATURE:
<223> OTHER INFORMATION: Synthetic Construct

<400> SEQUENCE: 36

```
atggccaaga gccatctgct gcagtggttg ctgctgctgc ccaccctgtg ttgtcctggc    60
gccgctatca caagcgccag cagcctggaa tgtgcccagg gccctcagtt ctggtgccag   120
tctctggaac acgccgtgca gtgtagagcc ctgggccact gtctgcagga agtgtgggga   180
cacgctggcg ccaacgacct gtgtcaggaa tgcgaggaca tcgtgcatct gctgaccaag   240
atgaccaaag aggacgcctt ccaggaagct atccgcaagt tcctggaaca ggaatgtgac   300
atcctgcccc tgaagctgct ggtgcctaga tgcagacagg tgctggacgt gtacctgcct   360
ctcgtgatcg actacttcca gagccagatc aaccctaagg ccatctgcaa ccacgtgggc   420
ctgtgcccta gaggccaggc taagcctgag cagaaccccg gcatgcctga cgccgtgcct   480
aaccctctgc tggacaagct ggtgctgcct gtgctgccag cgctctgct ggctagacct   540 ggacctcaca cccaggactt cagcgagcag cagctgccca tcccctgcc tttctgttgg   600 ctgtgcagaa ccctgatcaa gagggtgcag gccgtgatcc caagggtgt gctggctgtg   660 gctgtgtccc agtgtgcca cgtggtaccc tggtggtgg gtggcatctg ccagtgcctg   720
gccgagagat acaccgtgct gctgctggat gccctgctgg gcagagtggt gcctcagctc   780
gtgtgtggcc tggtgctgag atgctctacc gaggacgcta tgggccctgc cctgcctgct   840 gtggaaccc tgatcgagga atggcccctg caggataccg agtgccactt ctgcaagagc   900
gtgatcaacc aggcttggaa cacctccgag caggccatgc cccaggctat gcatcaggcc   960
tgcctgagat tctggctgga cagacagaaa tgcgagcagt ttgtggaaca gcacatgcca  1020
cagctgctgg ccctggtgcc aagatctcag gacgcccaca tcacctgtca ggctctggga  1080
gtgtgcgagg cccctgctag tcctctgcag tgcttccaga ccccccacct gctcgaggaa  1140
caaaaactca tctcagaaga ggatctgtga                                   1170
```

<210> SEQ ID NO 37
<211> LENGTH: 1197
<212> TYPE: DNA
<213> ORGANISM: Artificial Sequence
<220> FEATURE:
<223> OTHER INFORMATION: Synthetic Construct

<400> SEQUENCE: 37

```
atggccaaga gccatctgct gcagtggttg ctgctgctgc ccaccctgtg ttgtcctggc    60
gccgctatca caagcgccag cagcctggaa tgtgcccagg gccctcagtt ctggtgccag   120
tctctggaac acgccgtgca gtgtagagcc ctgggccact gtctgcagga agtgtgggga   180
cacgctggcg ccaacgacct gtgtcaggaa tgcgaggaca tcgtgcatct gctgaccaag   240
atgaccaaag aggacgcctt ccaggaagct atccgcaagt tcctggaaca ggaatgtgac   300
atcctgcccc tgaagctgct ggtgcctaga tgcagacagg tgctggacgt gtacctgcct   360
ctcgtgatcg actacttcca gagccagatc aaccctaagg ccatctgcaa ccacgtgggc   420
ctgtgcccta gaggccaggc taagcctgag cagaaccccg gcatgcctga cgccgtgcct   480
```

| | |
|---|---|
| aaccctctgc tggacaagct ggtgctgcct gtgctgccag gcgctctgct ggctagacct | 540 |
| ggacctcaca cccaggactt cagcgagcag cagctgccca tcccctgcc tttctgttgg | 600 |
| ctgtgcagaa ccctgatcaa gagggtgcag gccgtgatcc caagggtgt gctggctgtg | 660 |
| gctgtgtccc aggtgtgcca cgtggtaccc ctggtggtgg gtggcatctg ccagtgcctg | 720 |
| gccgagagat acaccgtgct gctgctggat gccctgctgg gcagagtggt gcctcagctc | 780 |
| gtgtgtggcc tggtgctgta cccatacgat gttccagatt acgctagatg ctctaccgag | 840 |
| gacgctatgg gccctgccct gctgctgtg gaaccctga tcgaggaatg gcccctgcag | 900 |
| gataccgagt gccacttctg caagagcgtg atcaaccagg cttggaacac ctccgagcag | 960 |
| gccatgcccc aggctatgca tcaggcctgc ctgagattct ggctggacag acagaaatgc | 1020 |
| gagcagtttg tggaacagca catgccacag ctgctggccc tggtgccaag atctcaggac | 1080 |
| gcccacatca cctgtcaggc tctgggagtg tgcgaggccc ctgctagtcc tctgcagtgc | 1140 |
| ttccagaccc cccacctgct cgaggaacaa aaactcatct cagaagagga tctgtga | 1197 |

<210> SEQ ID NO 38
<211> LENGTH: 1182
<212> TYPE: DNA
<213> ORGANISM: Homo Sapiens

<400> SEQUENCE: 38

| | |
|---|---|
| atgcaccaag cagggtaccc aggctgcaga ggtgccatgg ctgagtcaca cctgctgcag | 60 |
| tggctgctgc tgctgctgcc cacgctctgt ggcccaggca ctgctgcctg gaccacctca | 120 |
| tccttggcct gtgccaggg ccctgagttc tggtgccaaa gctggagca agcattgcag | 180 |
| tgcagagccc tagggcattg cctacaggaa gtctggggac atgtgggagc cgatgaccta | 240 |
| tgccaagagt gtgaggacat cgtccacatc cttaacaaga tggccaagga ggccatttc | 300 |
| caggacacga tgaggaagtt cctggagcag gagtgcaacg tcctccccctt gaagctgctc | 360 |
| atgccccagt gcaaccaagt gcttgacgac tacttccccc tggtcatcga ctacttccag | 420 |
| aaccagactg actcaaacgg catctgtatg cacctgggcc tgtgcaaatc ccggcagcca | 480 |
| gagccagagc aggagccagg gatgtcagac cccctgccca acctctgcg ggaccctctg | 540 |
| ccagaccctc tgctggacaa gctcgtcctc cctgtgctgc cggggcccct ccaggcgagg | 600 |
| cctgggcctc acacacagga tctctccgag cagcaattcc ccattcctct cccctattgc | 660 |
| tggctctgca gggctctgat caagcggatc caagccatga ttcccaaggg tgcgctagct | 720 |
| gtggcagtgg cccaggtgtg ccgcgtggta cctctggtgg cggcggcat ctgccagtgc | 780 |
| ctggctgagc gctactccgt catcctgctc gacacgctgc tgggccgcat gctgcccag | 840 |
| ctggtctgcc gctcgtcct ccggtgctcc atggatgaca cgctggccc aaggtcgccg | 900 |
| acaggagaat ggctgccgcg agactctgag tgccacctct gcatgtccgt gaccacccag | 960 |
| gccgggaaca gcagcgagca ggccataccá caggcaatgc tccaggcctg tgttggctcc | 1020 |
| tggctggaca gggaaaagtg caagcaattt gtggagcagc acacgcccca gctgctgacc | 1080 |
| ctggtgccca ggggctggga tgcccacacc acctgccagg ccctcggggt gtgtgggacc | 1140 |
| atgtccagcc ctctccagtg tatccacagc cccgaccttt ga | 1182 |

<210> SEQ ID NO 39
<211> LENGTH: 47
<212> TYPE: DNA
<213> ORGANISM: Artificial Sequence
<220> FEATURE:
<223> OTHER INFORMATION: Synthetic Construct

```
<400> SEQUENCE: 39
tacccatacg atgttccaga ttacgctaga tgctctaccg aggacgc                47

<210> SEQ ID NO 40
<211> LENGTH: 49
<212> TYPE: DNA
<213> ORGANISM: Artificial Sequence
<220> FEATURE:
<223> OTHER INFORMATION: Synthetic Construct

<400> SEQUENCE: 40
agcgtaatct ggaacatcgt atgggtacag caccaggcca cacacgagc              49
```